(12) United States Patent
Xiao

(10) Patent No.: US 7,060,810 B2
(45) Date of Patent: Jun. 13, 2006

(54) REGULATION OF HUMAN EOSINOPHIL SERINE PROTEASE 1-LIKE ENZYME

(75) Inventor: Yonghong Xiao, Cambridge, MA (US)

(73) Assignee: Bayer Aktiengesellschaft (DE)

(*) Notice: Subject to any disclaimer, the term of this patent is extended or adjusted under 35 U.S.C. 154(b) by 248 days.

(21) Appl. No.: 10/424,836

(22) Filed: Apr. 29, 2003

(65) Prior Publication Data

US 2003/0224430 A1 Dec. 4, 2003

Related U.S. Application Data

(62) Division of application No. 09/885,441, filed on Jun. 21, 2001, now abandoned.

(60) Provisional application No. 60/212,844, filed on Jun. 21, 2000, provisional application No. 60/244,171, filed on Oct. 31, 2000, provisional application No. 60/279,766, filed on Mar. 30, 2001.

(30) Foreign Application Priority Data

Jun. 20, 2001 (EP) .................. PCT/EP01/06936

(51) Int. Cl.
*C12N 15/57* (2006.01)
*C12N 15/79* (2006.01)
*C12N 15/81* (2006.01)
*C12Q 1/68* (2006.01)

(52) U.S. Cl. .................. 536/23.2; 435/6; 435/69.1; 435/252.3; 435/254.23; 435/320.1

(58) Field of Classification Search .................. 435/6, 435/69.1, 252.3, 320.1; 536/24.31, 23.2
See application file for complete search history.

(56) References Cited

U.S. PATENT DOCUMENTS

| 6,479,274 B1* | 11/2002 | Antalis et al. ............ 435/252.3 |
| 2002/0064856 A1* | 5/2002 | Plowman et al. ............ 435/226 |
| 2003/0139572 A1* | 7/2003 | Agarwal et al. ............ 530/350 |
| 2004/0077048 A1* | 4/2004 | Warren et al. ............ 435/69.1 |

FOREIGN PATENT DOCUMENTS

| WO | WO 98/36054 | 8/1998 |
| WO | WO 00/29448 | 5/2000 |
| WO | WO 01/72961 A2 | 10/2001 |
| WO | WO 02/00860 A2 | 1/2002 |

OTHER PUBLICATIONS

Hoopen J. D. et al., "Testisin, A New Human Serine Proteinase Expressed by Premeiotic Testicular Germ Cells And Lost in Testicular Germ Cell Tumors", Cancer Research, Baltimore MD., vol. 59, Jul. 1, 1999; pp. 3199-3205.; Abstract XP002924343.

(Continued)

*Primary Examiner*—Nashaat T. Nashed
*Assistant Examiner*—William W. Moore
(74) *Attorney, Agent, or Firm*—Banner & Witcoff, Ltd.

(57) ABSTRACT

A human eosinophil serine protease 1-like enzyme, cDNA, and reagents that regulate the enzyme can play a role in preventing, ameliorating, or correcting dysfunctions or diseases including, but not limited to, asthma, COPD, airway allergy, and osteoporosis.

17 Claims, 29 Drawing Sheets

OTHER PUBLICATIONS

Masahiro Inoue, et al.; "Cloning and Tissue Distribution of a Novel Serine Protease esp-l from Human Eosinophils" Biochemical And Biophysical Research Communications vol. 252, 307-312 (1998) Article No. RC989645.

Masahiro Inoue, et al.; Structural Analysis of esp-1 Gene (PRSS 21): Biochemical and Biophysical Research Communications vol. 266, pp. 564-568 (1999); Article ID bbrc. 1999.1870.

* cited by examiner

FIG. 1

BLASTP - Query = 139_TR1; Hit = trembl|AB031329|AB031329_1

This hit is scoring at : 1e-83 (expectation value)

Alignment length (overlap) : 308

Identities : 51 %

Scoring matrix : BLOSUM62 (used to infer consensus pattern)

Database searched : nrdb

```
Q:    1 MGARGALLLALLLARAGLGKPEA---------CGHREIHALVAGGVESARGRWPWQASLR
        MGARGALLLALLLARAGL KPE:         CG.R I : :.GG ::. GRWPWQ.SLR
H:    1 MGARGALLLALLLARAGLRKPESQEAAPLSGPCGRRVITSRIVGGEDAELGRWPWQGSLR

LRRRHRCGGSLLSRRWVLSAAHCFQN---------------QLLG-----TCGAYSSRYK
        L .H CG SLLS.RW.L:AAHCF:.               QL..    :. AY :RY
        LWDSHVCGVSLLSHRWALTAAHCFETYSDLSDPSGWMVQFGQLTSMPSFWSLQAYYTRYF
                                TRYPSIN_HIS

VQDIIVNPDALGVLRNDIALLRLASSVTYNAYIQPICIESSTFNFVHRPDCWVTGWGLIS
        V.:I.::P LG   DIAL::L::.VTY...:IQPIC:::STF.F :R.DCWVTGWG.I.
        VSNIYLSPRYLGNSPYDIALVKLSAPVTYTKHIQPICLQASTFEFENRTDCWVTGWGYIK

PSGTPLPPPYNLREAQVTILNNTRCNYLFEQPSSRSMIWDSMFCAGAEDGSVDTCKGDSG
        .. . LP.P:.L:E.QV.I:NN:..CN:LF : S R. I:..M.CAG ..G. D.C GDSG
        EDEA-LPSPHTLQEVQVAIINNSMCNHLFLKYSFRKDIFGDMVCAGNAQGGKDACFGDSG
                                                        TRYPSIN_SER

GPLVCDKDGLWYQVGIVSWGMDCGQPNRPGVYTNISVYFHWIRRVMSHS-TPRPNPSQLL
        GPL.C:K:GLWYQ:G:VSWG:.CG:PNRPGVYTNIS :F.WI:::M:.S ...:P:PS L
        GPLACNKNGLWYQIGVVSWGVGCGRPNRPGVYTNISHHFEWIQKLMAQSGMSQPDPSWPL

LLLALLWA    278 (SEQ.ID. NO: 2)
        L...LLWA
        LFFPLLWA    307 (SEQ.ID. NO: 15)
```

FIG. 2

Prosite search results:

| Access# | From->To | Name | Doc# |
|---------|----------|------|------|
| PS00134 | 69->75 | TRYPSIN_HIS | PDOC00124 |
| PS00135 | 204->216 | TRYPSIN_SER | PDOC00124 |

FIG. 3

BLOCKS search results:

| AC# | Description | Strength | Score |
|---|---|---|---|
| BL00495N | Apple domain proteins. | 1945 | 1554 |

AA# 195 AgaedGsvDtCKGDSGGPLVCdkdGlWyqVGIvSW (SEQ.ID. NO: 3)
BL00134A    Serine proteases, trypsin family, histidine p    1500    1519

AA# 57 CGGSLLSRRWVLSAAHC (SEQ.ID. NO: 4)
BL00021B    Kringle domain proteins.    1547    1489

AA# 57 CGGSLlSrRWVLSAAHCF (SEQ.ID. NO: 5)
BL01253G    Type I fibronectin domain proteins.    1641    1451

AA# 202 vDtCkGDSGGPLVC (SEQ.ID. NO: 6)
BL00021D    Kringle domain proteins.    1556    1446

AA# 211 GPLVCdKDGlWYQVGIVSWGmDCGQPNRPGVYTniSVYfhWI (SEQ.ID. NO: 7)
BL01253H    Type I fibronectin domain proteins.    1765    1417

AA# 221 wYqVGIvSWGmdCGQpNrPGVYTnisvYfhWIRrv (SEQ.ID. NO: 8)
BL00134B    Serine proteases, trypsin family, histidine p    1289    1292

AA# 203 DTCKGDSGGPLVCDKDGLWYQVGI (SEQ.ID. NO: 9)
BL00495M    Apple domain proteins.    1943    1264

AA# 117 VtYnayiqPICieSstfnfVhrpDCWVTGWGlisp (SEQ.ID. NO: 10)
BL01253D    Type I fibronectin domain proteins.    1398    1240

AA# 57 CGGSLlSrrWVLSA (SEQ.ID. NO: 11)
BL004950    Apple domain proteins.    1756    1225

AA# 230 GmdCGQpnRPGVYTNiSvYfhWIrrvmsh (SEQ.ID. NO: 12)
BL00134C    Serine proteases, trypsin family, histidine p    1245    1217

AA# 239 PGVYTNISVYFHWI (SEQ.ID. NO: 13)

FIG. 4A

BLASTN - alignment of 139_2 against embl|AC005570|AC005570
Homo sapiens chromosome 16, cosmid clone 407D8 (LANL), complete
sequence.//:genbank|AC005570|AC005570 Homo sapiens chromosome 16, cosmid
clone 407D8 (LANL), complete sequence.
This hit is scoring at : 5e-127 (expectation value)
Alignment length (overlap) : 233
Identities : 100 %
Scoring matrix : blastn (used to infer consensus pattern)
Query reading frame : +1
Hit reading frame : -1
Database searched : nrnee_1_;

```
Q:    231 ccaactccttggaacctgcgggccctacagcagtcgttacaaagtgcaggacatcattgt
          CCAACTCCTTGGAACCTGCGGGCCCTACAGCAGTCGTTACAAAGTGCAGGACATCATTGT
H:  12591 ccaactccttggaacctgcgggccctacagcagtcgttacaaagtgcaggacatcattgt gaaccctgacgcacttggggttttacgcaatgacattgccctgctgagactggcctcttc
          GAACCCTGACGCACTTGGGGTTTTACGCAATGACATTGCCCTGCTGAGACTGGCCTCTTC
          gaaccctgacgcacttggggttttacgcaatgacattgccctgctgagactggcctcttc tgtcacctacaatgcgtacatccagccatttgcatcgagtcttccaccttcaacttcgt
          TGTCACCTACAATGCGTACATCCAGCCATTTGCATCGAGTCTTCCACCTTCAACTTCGT
          tgtcacctacaatgcgtacatccagccatttgcatcgagtcttccaccttcaacttcgt gcaccggccgactgctgggtgaccggctgggggttaatcagcccagtggca          463
          GCACCGGCCGACTGCTGGGTGACCGGCTGGGGGTTAATCAGCCCCAGTGGCA
          gcaccggccgactgctgggtgaccggctgggggttaatcagcccagtggca          12359
```

FIG. 4B

BLASTN - alignment of 139_2 against embl|AC005570|AC005570
Homo sapiens chromosome 16, cosmid clone 407D8 (LANL), complete
sequence.//:genbank|AC005570|AC005570 Homo sapiens chromosome 16, cosmid
clone 407D8 (LANL), complete sequence.
This hit is scoring at : 5e-117 (expectation value)
Alignment length (overlap) : 216
Identities : 100 %
Scoring matrix : blastn (used to infer consensus pattern)
Query reading frame : +1
Hit reading frame : -1
Database searched : nrmee_1_;

```
Q:    622 ggtgactcaggtggaccctggtctgtgacaaggatgactgtggtatcaggttggaatc
          GGTGACTCAGGTGGACCCTGGTCTGTGACAAGGATGACTGTGGTATCAGGTTGGAATC
H:   7015 ggtgactcaggtggaccctggtctgtgacaaggatgactgtggtatcaggttggaatc gtgagctggggaatggactgcggtcaacccaatcggcctggtctacaccaacatcagt
          GTGAGCTGGGAATGGACTGACTGCGGTCAACCCAATCGGCCTGGTCTGTCTACACCAACATCAGT
          gtgagctggggaatggactgcggtcaacccaatcggcctgtgtctacaccaacatcagt gtgtacttccactgatccgagggtgatgtcccacagtacacccaggccaaaccctcc
          GTGTACTTCCACTGATCCGGAGGGTGATGTCCCACAGTACACCCAGGCCAAACCCTCC
          gtgtacttccactgatccgagggtgatgtcccacagtacacccaggccaaaccctcc cagctgttgctgctccttgccctgctgggctccc          837
          CAGCTGTTGCTGCTCCTTGCCCTGCTGGGCTCCC
          cagctgttgctgctccttgccctgctgggctccc         6800
```

FIG. 4C

BLASTN - alignment of 139_2 against embl|AC005570|AC005570
Homo sapiens chromosome 16, cosmid clone 407D8 (LANL), complete
sequence.//:genbank|AC005570|AC005570 Homo sapiens chromosome 16, cosmid
clone 407D8 (LANL), complete sequence.
This hit is scoring at : 1e-87 (expectation value)
Alignment length (overlap) : 167
Identities : 100 %
Scoring matrix : blastn (used to infer consensus pattern)
Query reading frame : +1
Hit reading frame : -1
Database searched : nrnee_1_;

```
Q:     64 gaggcctgcggccaccggaaattcacgcgctgtgtgcgggcggagtggagtccgcgcgc
          GAGGCCTGCGGCCACCGGAAATTCACGCGCTGTGTGCGGGCGGAGTGGAGTCCGCGCGC
H:  12971 gaggcctgcggccaccggaaattcacgcgctgtgtgcgggcggagtggagtccgcgcgc gggcgctggcaggccagccagcctgcgcctgaggagacgccaccgatgtggagggagc
           GGGCGCTGGCCATGGCCAGGCAGGCCAGCCTGCGCCTGAGGAGACGCCACCGATGTGGAGGGAGC
           gggcgctggccatggccaggcaggccagcctgcgcctgaggagacgccaccgatgtggagggagc ctgctcagccgccgctgggtgtctcggctgcgcactgcttccaaaa       230
           CTGCTCAGCCGCCGCTGGGTGTCTCGGCTGCGCACTGCTTCCAAAA
           ctgctcagccgccgctgggtgtctcggctgcgcactgcttccaaaa     12805
```

FIG. 4D

BLASTN - alignment of 139_2 against embl|AC005570|AC005570
Homo sapiens chromosome 16, cosmid clone 407D8 (LANL), complete
sequence.//:genbank|AC005570|AC005570 Homo sapiens chromosome 16, cosmid
clone 407D8 (LANL), complete sequence.
This hit is scoring at : 6e-83 (expectation value)
Alignment length (overlap) : 159
Identities : 100 %
Scoring matrix : blastn (used to infer consensus pattern)
Query reading frame : +1
Hit reading frame : -1
Database searched : nrmee_1_;

```
Q:    464  cacctctgccacctccttacaacctccgggaagcacagtkcaccatcttaaacaacacca
           CACCTCTGCCACCTCCTTACAACCTCCGGGAAGCACAGTCACCATCTTAAACAACACCA
H:   7540  cacctctgccacctccttacaacctccgggaagcacagtcaccatcttaaacaacacca ggtgtaattacctgtttgaacagccctctagccgtagtatgatctggattccatgtttt
           GGTGTAATTACCTGTTTGAACAGCCCTCTAGCCGTAGTATGATCTGGATTCCATGTTTT
           ggtgtaattacctgtttgaacagccctctagccgtagtatgatctggattccatgtttt gtgctggtgctgaggatggcagtgtagacacctgcaaag                       622
           GTGCTGGTGCTGAGGATGGCAGTGTAGACACCTGCAAAG
           gtgctggtgctgaggatggcagtgtagacacctgcaaag                      7382
```

FIG. 5A

```
Esp-1-like  ..........  ........AT  GGGCGCGCGC  GGGGCGCTGC  TGCTGGCGCT
AB031329    ........G   AGGAGGCCAT  GGGCGCGCGC  GGGGCGCTGC  TGCTGGCGCT
NM006799    GCCGCGGGAG  AGGAGGCCAT  GGGCGCGCGC  GGGGCGCTGC  TGCTGGCGCT Esp-1-like  GCTGCTGGCT  GGGGCTGGAC  TCGGGAAGCC  GGAG......  ........GC
AB031329    GCTGCTGGCT  CGGGCTGGAC  TCAGGAAGCC  GGAGTCGCAG  GAGGCGGCGC
NM006799    GCTGCTGGCT  CGGGCTGGAC  TCAGGAAGCC  GGAGTCGCAG  GAGGCGGCGC Esp-1-like  C..T......  .....GCGGC  CACCGGGAAA  TTCACG.CGC  TGGTGGCGGG
AB031329    CGTTATCAGG  ACCATGCGGC  CGACGGGTCA  T.CACGTCGC  GCATCGTGGG
NM006799    CGTTATCAGG  ACCATGCGGC  CGACGGGTCA  T.CACGTCGC  GCATCGTGGG Esp-1-like  CGGAGTGGAG  TCCGCGCGCG  GGCGCTGGCC  ATGGCAGGCC  AGCCTGCGCC
AB031329    TGGAGAGGAC  GCCGAACTCG  GGCGTTGGCC  GTGGCAGGGG  AGCCTGCGCC
NM006799    TGGAGAGGAC  GCCGAACTCG  GGCGTTGGCC  GTGGCAGGGG  AGCCTGCGCC Esp-1-like  TGAGGAGACG  CCACCGATGT  GGAGGGAGCC  TGCTCAGCCG  CCGCTGGGTG
AB031329    TGTGGGATTC  CCACGTATGC  GGAGTGAGCC  TGCTCAGCCA  CCGCTGGGCA
NM006799    TGTGGGATTC  CCACGTATGC  GGAGTGAGCC  TGCTCAGCCA  CCGCTGGGCA Esp-1-like  CTCTCGGCTG  CGCACTGCTT  CCAAA.....  .....ACC...  ...AAC....
AB031329    CTCACGGCGG  CGCACTGCTT  TGAAACCTAT  AGTGACCTTA  GTGATCCCTC
NM006799    CTCACGGCGG  CGCACTGCTT  TGAAACCTAT  AGTGACCTTA  GTGATCCCTC Esp-1-like  ..........  ..........  ..........  ..........  TCCTT..GGA
AB031329    CGGGTGGATG  GTCCAGTTTG  GCCAGCTGAC  TTCCATGCCA  TCCTTCTGGA
NM006799    CGGGTGGATG  GTCCAGTTTG  GCCAGCTGAC  TTCCATGCCA  TCCTTCTGGA Esp-1-like  ACCTGCGGGG  CCTACAGCAG  TCGTTACAAA  GTGCAGGACA  TCATTGTGAA
AB031329    GCCTGCAGG.  CCTACTACAC  CCGTTACTTC  GTATCGAATA  TCTATCTGAG
NM006799    GCCTGCAGG.  CCTACTACAC  CCGTTACTTC  GTATCGAATA  TCTATCTGAG Esp-1-like  CCCTGACGCA  CTTGGGGTTT  TACGCAATGA  CATTGCCCTG  CTGAGACTGG
AB031329    CCCTCGCTAC  CTGGGGAATT  CACCCTATGA  CATTGCCTTG  GTGAAGCTGT
NM006799    CCCTCGCTAC  CTGGGGAATT  CACCCTATGA  CATTGCCTTG  GTGAAGCTGT Esp-1-like  CCTCTTCTGT  CACCTACAAT  GCGTACATCC  AGCCCATTTG  CATCGAGTCT
AB031329    CTGCACCTGT  CACCTACACT  AAACACATCC  AGCCCATCTG  CCTCCAGGCC
NM006799    CTGCACCTGT  CACCTACACT  AAACACATCC  AGCCCATCTG  TCTCCAGGCC
```

FIG. 5B

```
Esp-1-like   TCCACCTTCA ACTTCGTGCA CCGGCCGGAC TGCTGGGTGA CCGGCTGGGG
AB031329     TCCACATTTG AGTTTGAGAA CCGGACAGAC TGCTGGGTGA CTGGCTGGGG
NM006799     TCCACATTTG AGTTTGAGAA CCGGACAGAC TGCTGGGTGA CTGGCTGGGG Esp-1-like   GTTAATCAGC CCCAGTGGCA CACCTCTGCC ACCTCCTTAC AACCTCCGGG
AB031329     GTACATCAAA GAGGATGAGG CAC...TGCC ATCTCCCCAC ACCCTCCAGG
NM006799     GTACATCAAA GAGGATGAGG CAC...TGCC ATCTCCCCAC ACCCTCCAGG Esp-1-like   AAGCACAGGT CACCATCTTA AACAACACCA GGTGTAATTA CCTGTTTGAA
AB031329     AAGTTCAGGT CGCCATCATA AACAACTCTA TGTGCAACCA CCTCTTCCTC
NM006799     AAGTTCAGGT CGCCATCATA AACAACTCTA TGTGCAACCA CCTCTTCCTC Esp-1-like   CAGCCCTCTA GCCGTAGTAT GATCTGGGAT TCCATGTTTT GTGCTGGTGC
AB031329     AAGTACAGTT TCCGCAAGGA CATCTTTGGA GACATGGTTT GTGCTGGCAA
NM006799     AAGTACAGTT TCCGCAAGGA CATCTTTGGA GACATGGTTT GTGCTGGCAA Esp-1-like   TGAGGATGGC AGTGTAGACA CCTGCAAAGG TGACTCAGGT GGACCCTTGG
AB031329     TGCCCAAGGC GGGAAGGATG CCTGCTTCGG TGACTCAGGT GGACCCTTGG
NM006799     TGCCCAAGGC GGGAAGGATG CCTGCTTCGG TGACTCAGGT GGACCCTTGG Esp-1-like   TCTGTGACAA GGATGGACTG TGGTATCAGG TTGGAATCGT GAGCTGGGGA
AB031329     CCTGTAACAA GAATGGACTG TGGTATCAGA TTGGAGTCGT GAGCTGGGGA
NM006799     CCTGTAACAA GAATGGACTG TGGTATCAGA TTGGAGTCGT GAGCTGGGGA Esp-1-like   ATGGACTGCG GTCAACCCAA TCGGCCTGGT GTCTACACCA ACATCAGTGT
AB031329     GTGGGCTGTG GTCGGCCCAA TCGGCCCGGT GTCTACACCA ATATCAGCCA
NM006799     GTGGGCTGTG GTCGGCCCAA TCGGCCCGGT GTCTACACCA ATATCAGCCA Esp-1-like   GTACTTCCAC TGGATCCGGA GGGTGATGTC CCACAGT... ACACCCAGGC
AB031329     CCACTTTGAG TGGATCCAGA AGCTGATGGC CCAGAGTGGC ATGTCCCAGC
NM006799     CCACTTTGAG TGGATCCAGA AGCTGATGGC CCAGAGTGGC ATGTCCCAGC Esp-1-like   CAAACCCCTC CCAGCTGTTG CTGCTCCTTG CCCTGCTGTG GGCTCCC...
AB031329     CAGACCCCTC CTGGCCACTA CTCTTTTTCC CTCTTCTCTG GCTCTCCCA
NM006799     CAGACCCCTC CTGGCCGCTA CTCTTTTTCC CTCTTCTCTG GCTCTCCCA Esp-1-like   .......... .......... .......... .......... ..........
AB031329     CTCCTGGGGC CGGTCTGAGC CTACCTGAGC CCATGCAGCC TGGGGCCACT
NM006799     CTCCTGGGGC CGGTCTGAGC CTACCTGAGC CCATGCAGCC TGGGGCCACT
```

FIG. 5C

```
Esp-1-like    ..........  ..........  ..........  ..........  ..........
AB031329      GCCAAGTCAG  GCCCTGGTTC  TCTTCTGTCT  TGTTTGGTAA  TAAACACATT
NM006799      GCCAAGTCAG  GCCCTGGTTC  TCTTCTGTCT  TGTTTGGTAA  TAAACACATT Esp-1-like    ..........  ..........  ..........  ..........  ......
AB031329      CCAGTTGATG  CCTTGCAGGG  CATTCTTCAA  AAAAAAAAAA  AAAAAA
NM006799      CCAGTTGATG  CCTTGCAGGG  CATTCTTCAA  AA........  ......
```

FIG. 6

HMMPFAM - alignment of SEQ ID NO:2 against pfam|hmm|trypsin

Trypsin

This hit is scoring at : 233.2

Scoring matrix : BLOSUM62 (used to infer consensus pattern)

```
Q:    71  VAGGVESARGRW--PWQASLRLRR-----RHRCGGSLLSRRWVLSAAHCFQK--HYYPSE
          :.GG E:. G.:  PWQ.SL::R.     :H CGGSL:S..WVL:AAHC..   . .S.
H:     1  IvGGreaqpgsfgsPwqvslqvrsggggsrkhfCGGsLisenwVLTAAHCvsgaasapass WTV----QLGE--LTSRPTPwnlraySSRYKVQD-IIVNPDALGVL------RNDIALLR
          .V     :LGE  L:. . .      ..::.V:. IIV:P:          NDIALL:
          vrVSlsvrlGehnlsltegt......eqkfdvkktiivHpnynpdtldngaYdnDiALlk LASS-VTYNAYIQPICIESsTFNFVhRPD--CWVTGWGL--ISPSGtplpPPYNLREAQV
          L.S. VT.. ::PIC:.S . : :   . C V:GWG  .. G    . .L:E. V
          Lkspgvtlgdtvrpiclps.assdl.pvGttctvsGwGrrptknlg....lsdtLqevvv TILNNTRCNYLFEqPSSR----SMIWDSMFCAGAEdGSVDTCKGDSGGPLVCDKD---GL
          .:::...C. .:E ...     ..: D:M.CAGA  G. D.C:GDSGGPLVC...   G
          pvvsretCrsaye.yggtdDkvefvtdnmiCagal.ggkdaCqGDSGGPLvcsdgnrdgr WYQVGIVSWG-MDCGQPNRPGVYTNISVYFHWI          308
          W  VGIVSWG ..C.: N:PGVYT.:S Y..WI
          welvGivSwGsygCargnkPGvytrVssyldWI          259
```

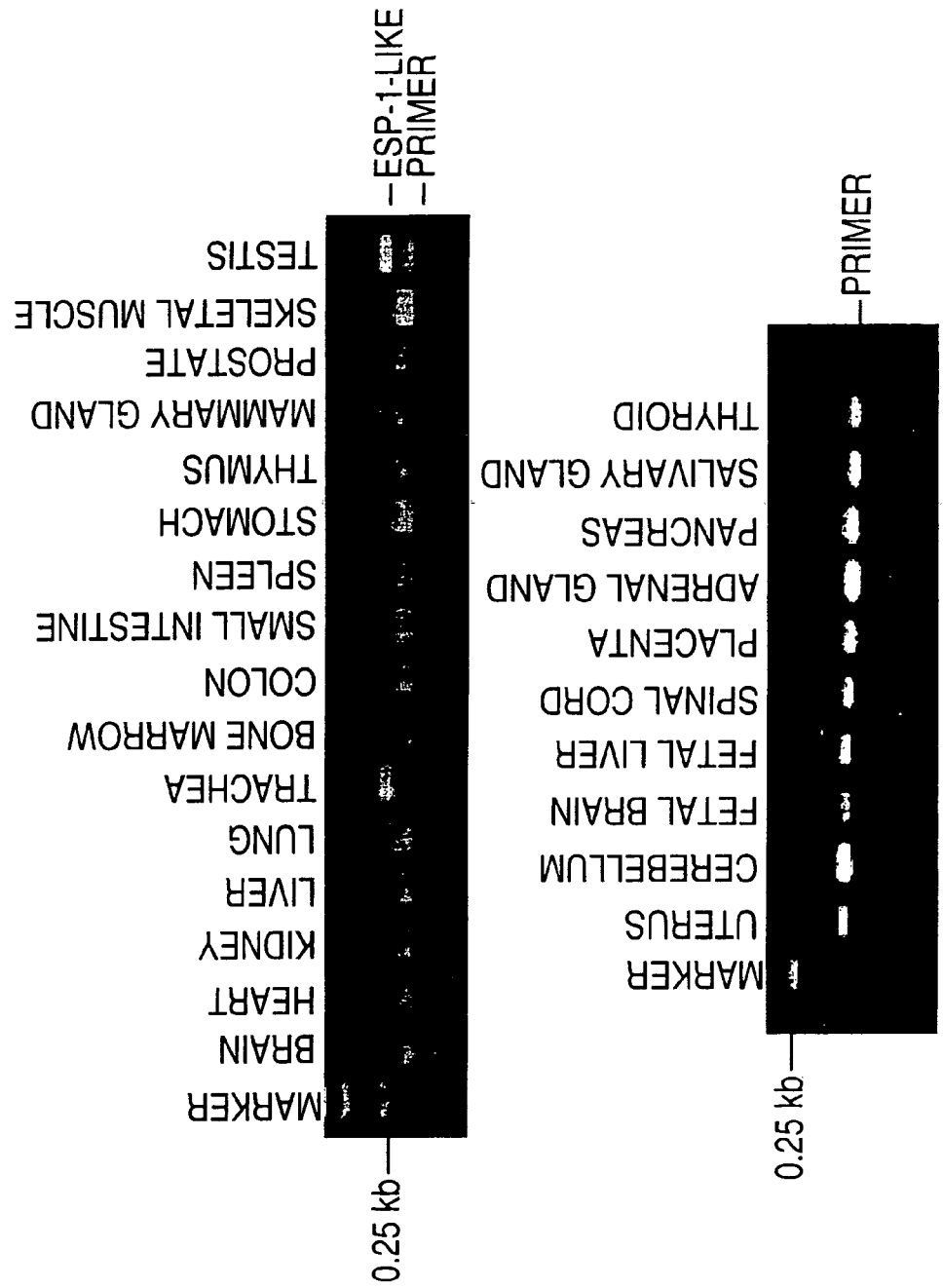

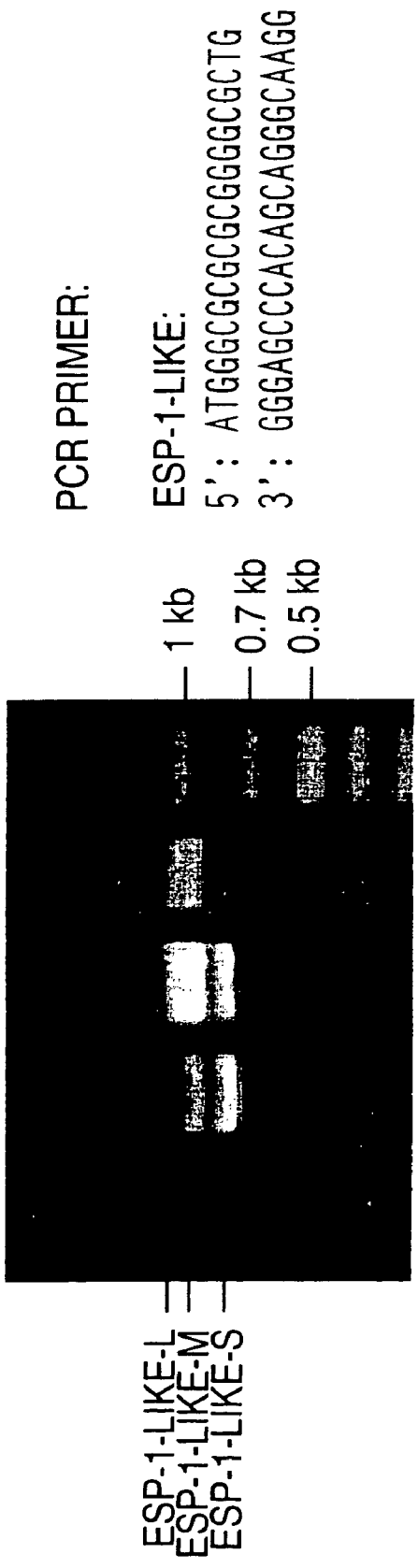

FIG. 9
Sequences of ESP-1-like gene

```
ESP-1-likeaa        MGARGALLLALLLARAGLGKFGELGALQAGPGAARRPGGGREGHFLCPAESQEEELISEACGHREIHALVAGGVESARGRWPWQASLRLRRBHRCGGS  98
ESP-1-like-LBRIaa   MGARGALLLALLLARAGLGKF                                     EACGHREIHALVAGGVESARGRWPWQASLRLRRBHRCGGS
ESP-1-like-LBRIaa   MGARGALLLALLLARAGLGKF-------------------------------------EACGHREIHALVAGGVESARGRWPWQASLRLRRBHRCGGS  61

ESP-1-likeaa        LLSRRWVLSAAHCFQRKHYYPSEWTVQLGELTSRPTPWNIAYSSRYKVQDIIVNPDALGVLRNDIALLRLASSVTYNAYIQPICIESSTFNFVHRPDCWV  199
ESP-1-like-LBRIaa   LLSRRWVLSAAHCFQ::                 L::           YSSRYKVQDIIVNPDALGVLRNDIALLRLASSVTYNAYIQPICIESSTFNFVHRPDCWV
ESP-1-like-LBRIaa   LLSRRWVLSAAHCFQNQ     LLGTCGA-----YSSRYKVQDIIVNPDALGVLRNDIALLRLASSVTYNAYIQPICIESSTFNFVHRPDCWV  144

ESP-1-likeaa        TGWGLISPSGTPLPPPYNLREAQVTILNNTRCNYLFEQPSSRSMIWDSMFCAGAEDGSVDTCKGDSGGPLVCDKDGLWYQVGIVSWGMDCGQPNRP  295
ESP-1-like-LBRIaa   TGWGLISPSGTPLPPPYNLREAQVTILNNTRCNYLFEQPSSRSMIWDSMFCAGAEDGSVDTCKGDSGGPLVCDKDGLWYQVGIVSWGMDCGQPNRP
ESP-1-like-LBRIaa   TGWGLISPSGTPLPPPYNLREAQVTILNNTRCNYLFEQPSSRSMIWDSMFCAGAEDGSVDTCKGDSGGPLVCDKDGLWYQVGIVSWGMDCGQPNRP  240

ESP-1-likeaa        GVYTNISVYFHWIRRVMSHSTPRPNPSQLLLLLALLWAP  334
ESP-1-like-LBRIaa   GVYTNISVYFHWIRRVMSHSTPRPNPSQLLLLLALLWAP
ESP-1-like-LBRIaa   GVYTNISVYFHWIRRVMSHSTPRPNPSQLLLLLALLWAP  279
```

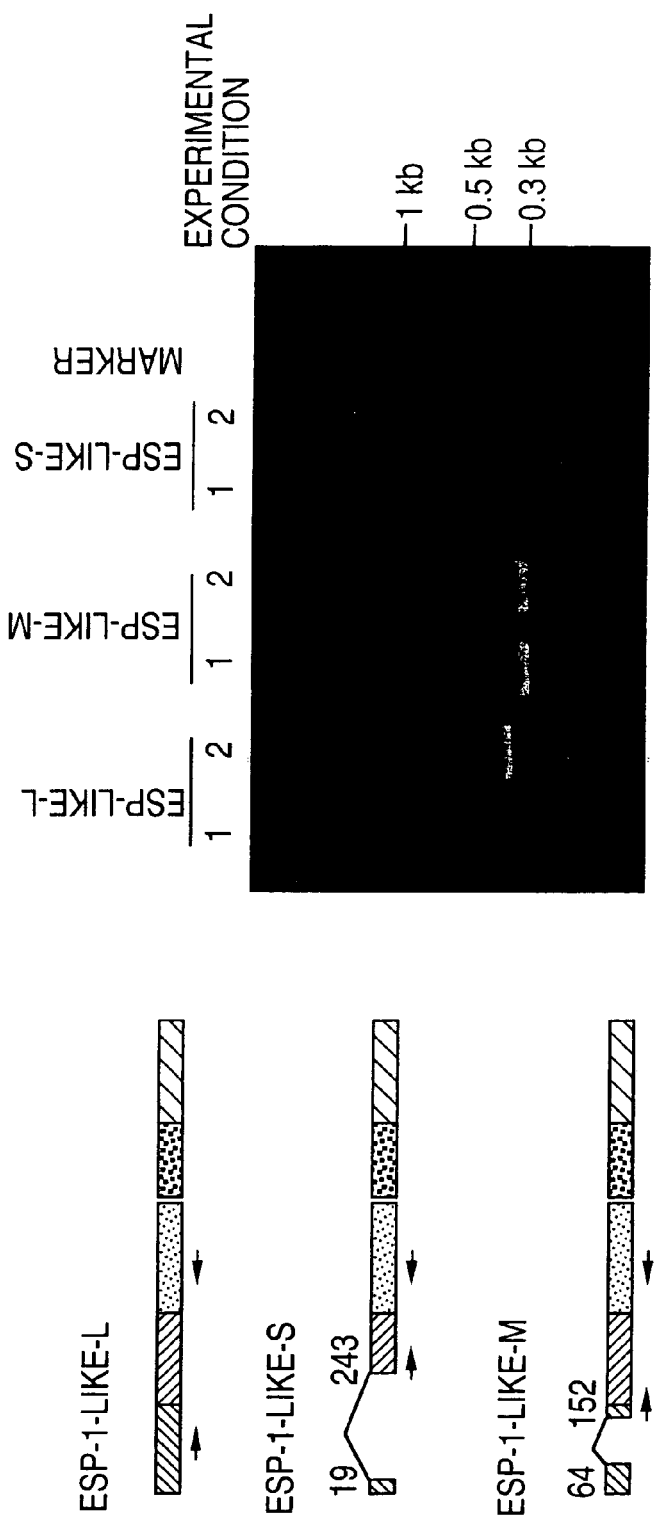

FIG. 11
Sequences of ESP-1-like and Its Variants

ESP-1-L-L
MGARGALLLALLLARAGLGKPGELGALQAGPGAARRPGGGGREGHFLCPAESQEEELLSEA
CGHREIHALVAGGVESARGRWPWQASLRLRRRHRCGGSLLSRRWVLSAAHCFQKHYYPSEW
TVQLGELTSRPTPWNLRAYSSRYKVQDIIVNPDALGVLRNDIALLRLASSVTYNAYIQPIC
IESSTFNFVHRPDCWVTGWGLISPSGTPLPPPYNLREAQVTILNNTRCNYLFEQPSSRSMI
WDSMFCAGAEDGSVDTCKGDSGGPLVCDKDGLWYQVGIVSWGMDCGQPNRPGVYTNISVYF
HWIRRVMSHSTPRPNPSQLLLLLALLWAP

ESP-1-L-M
MGARGALLLALLLARAGLGKPESQEEELLSEACGHREIHALVAGGVESARGRWPWQASLRL
RRRHRCGGSLLSRRWVLSAAHCFQKHYYPSEWTVQLGELTSRPTPWNLRAYSSRYKVQDII
VNPDALGVLRNDIALLRLASSVTYNAYIQPICIESSTFNFVHRPDCWVTGWGLISPSGTPL
PPPYNLREAQVTILNNTRCNYLFEQPSSRSMIWDSMFCAGAEDGSVDTCKGDSGGPLVCDK
DGLWYQVGIVSWGMDCGQPNRPGVYTNISVYFHWIRRVMSHSTPRPNPSQLLLLLALLWAP

ESP-1-L-S
MGARGAWPWQASLRLRRRHRCGGSLLSRRWVLSAAHCFQKHYYPSEWTVQLGELTSRPTPW
NLRAYSSRYKVQDIIVNPDALGVLRNDIALLRLASSVTYNAYIQPICIESSTFNFVHRPDC
WVTGWGLISPSGTPLPPPYNLREAQVTILNNTRCNYLFEQPSSRSMIWDSMFCAGAEDGSV
DTCKGDSGGPLVCDKDGLWYQVGIVSWGMDCGQPNRPGVYTNISVYFHWIRRVMSHSTPRP
NPSQLLLLLALLWAP

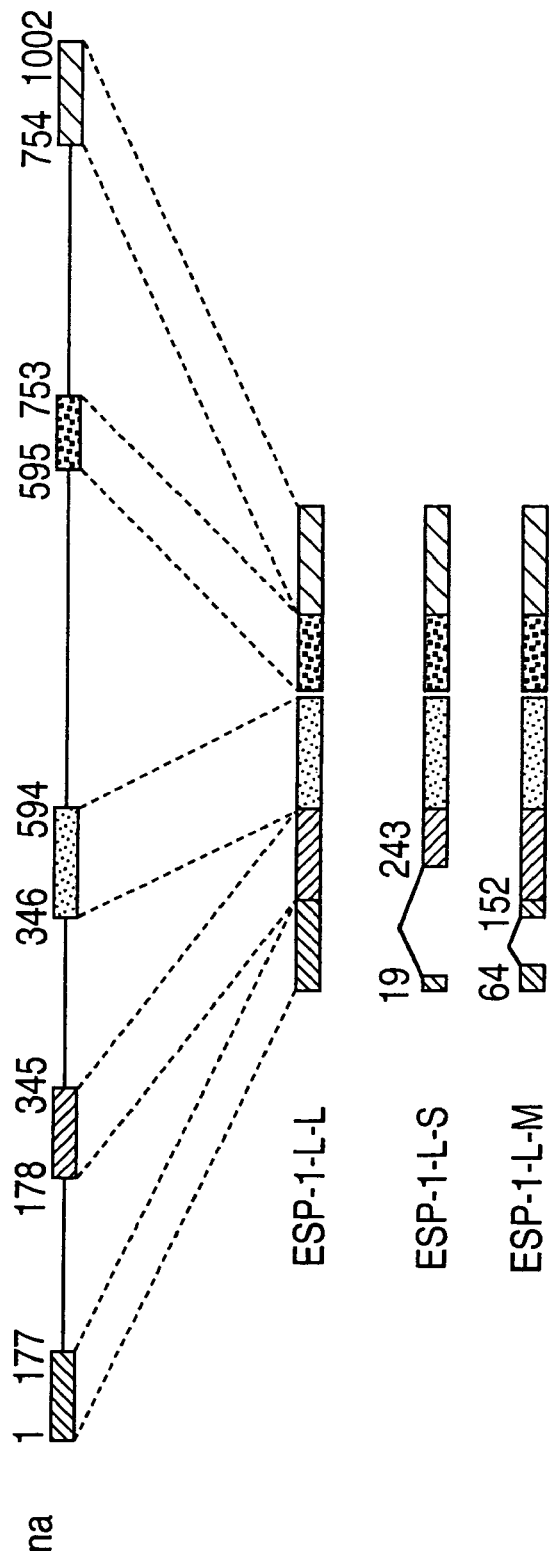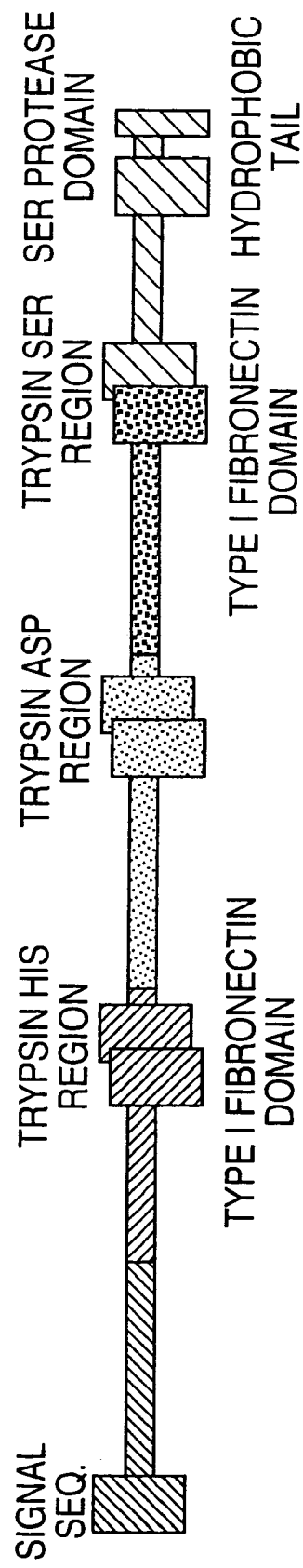
FIG. 12
STRUCTURE OF ESP-1-LIKE GENES

HOMOLOGY BETWEEN ESP-1/LIKE AND OTHER SERINE PROTEASE

MECHANISMS OF ACTIVATION OF TRYPTASE-LIKE SERINE PROTEASES

ESP-1-LIKE-M IS EXPRESSED AS A MEMBRANE PROTEIN

Protease Activity in the Membrane Fraction of ESP-1-L-M Expressing Cells

Positve Substrates:

Pro-Phe-Arg-MCA (Kallikrein)

Boc-Phe-Ser-Arg-MCA (Tryptase)

FIG. 16E

Negative Substrates:

- Cat B/E
- Chymotrypsin (Glt-Ala-Ala-Phe-MCA)

- MMP
- Trypsin (Bz-Arg-MCA)

(CBZ-L-Ile-L-Pro-L-Arg)

(CBZ-L-Arg)

- Collagenase-like peptidase
- Chymotrypsin ingensin (Suc-L-L-V-Y-MCA)

- Tripeptidyl Peptidase II
- Renin
- Elastase
- Leakocyte elastase

FIG. 17
EXPRESSION OF ESP-1-LIKE GENES IN LUNG PRIMARY CELLS
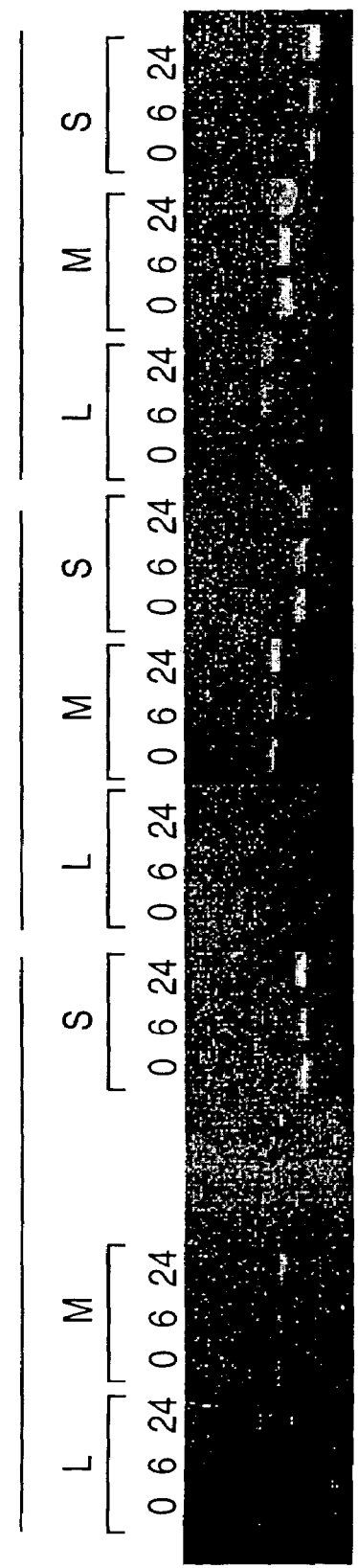
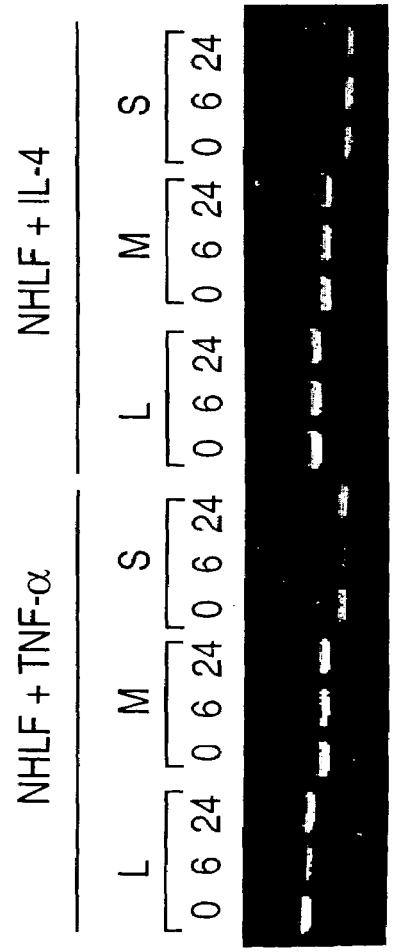

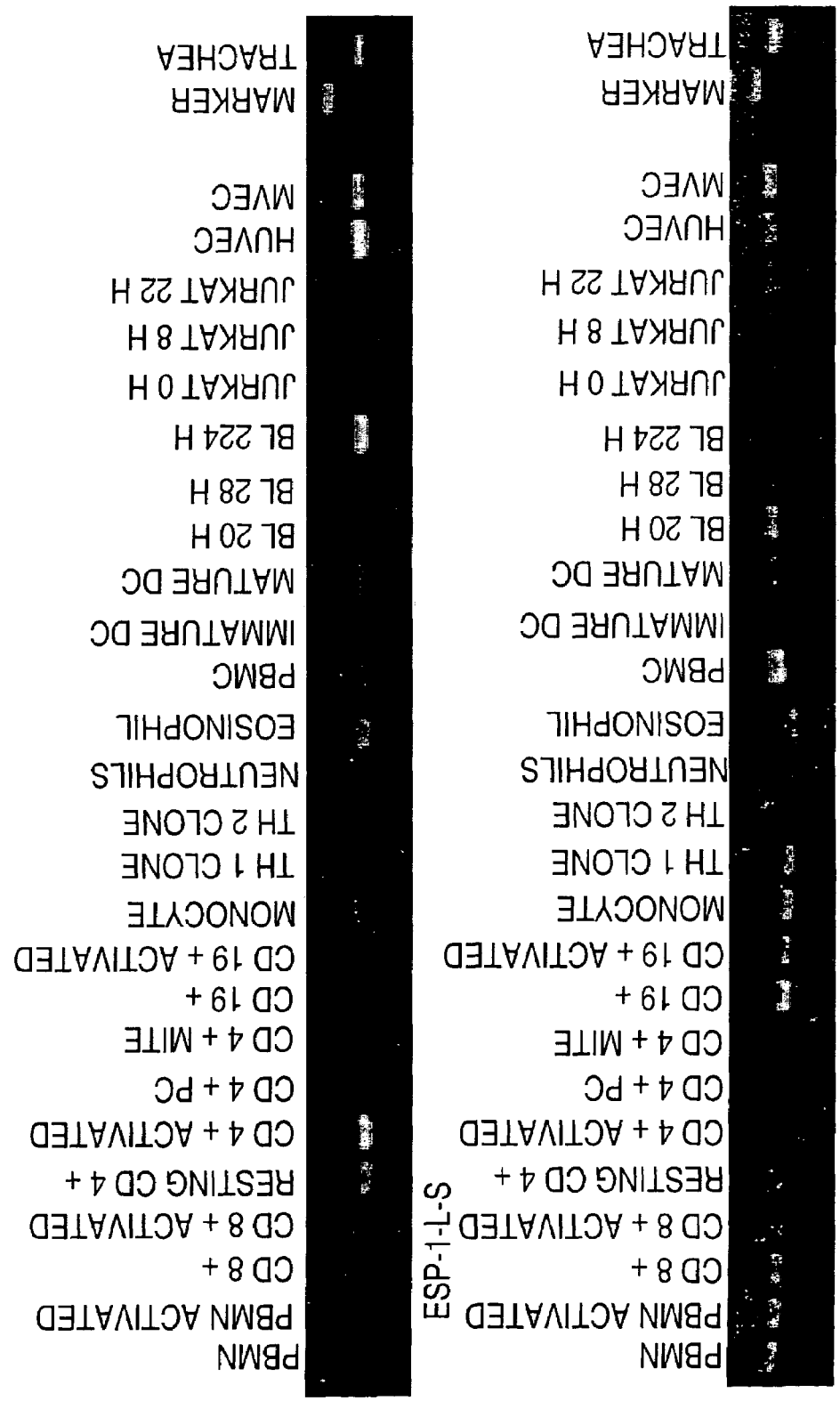
FIG. 18 EXPRESSION OF ESP-1-L GENES IN IMMUNE CELLS

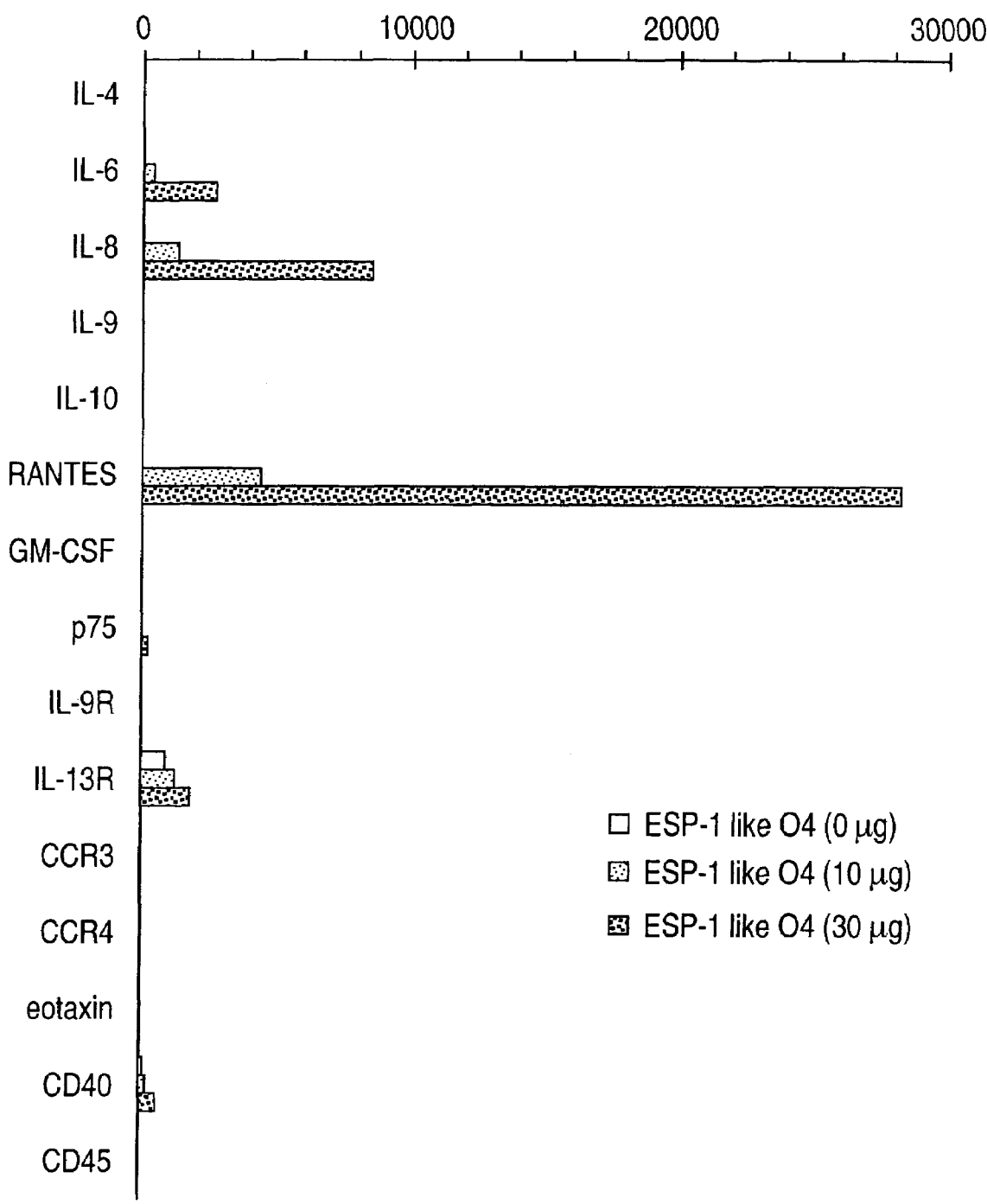

Overexpression of ESP-1 like O4 induces RANTES production on A549 cells

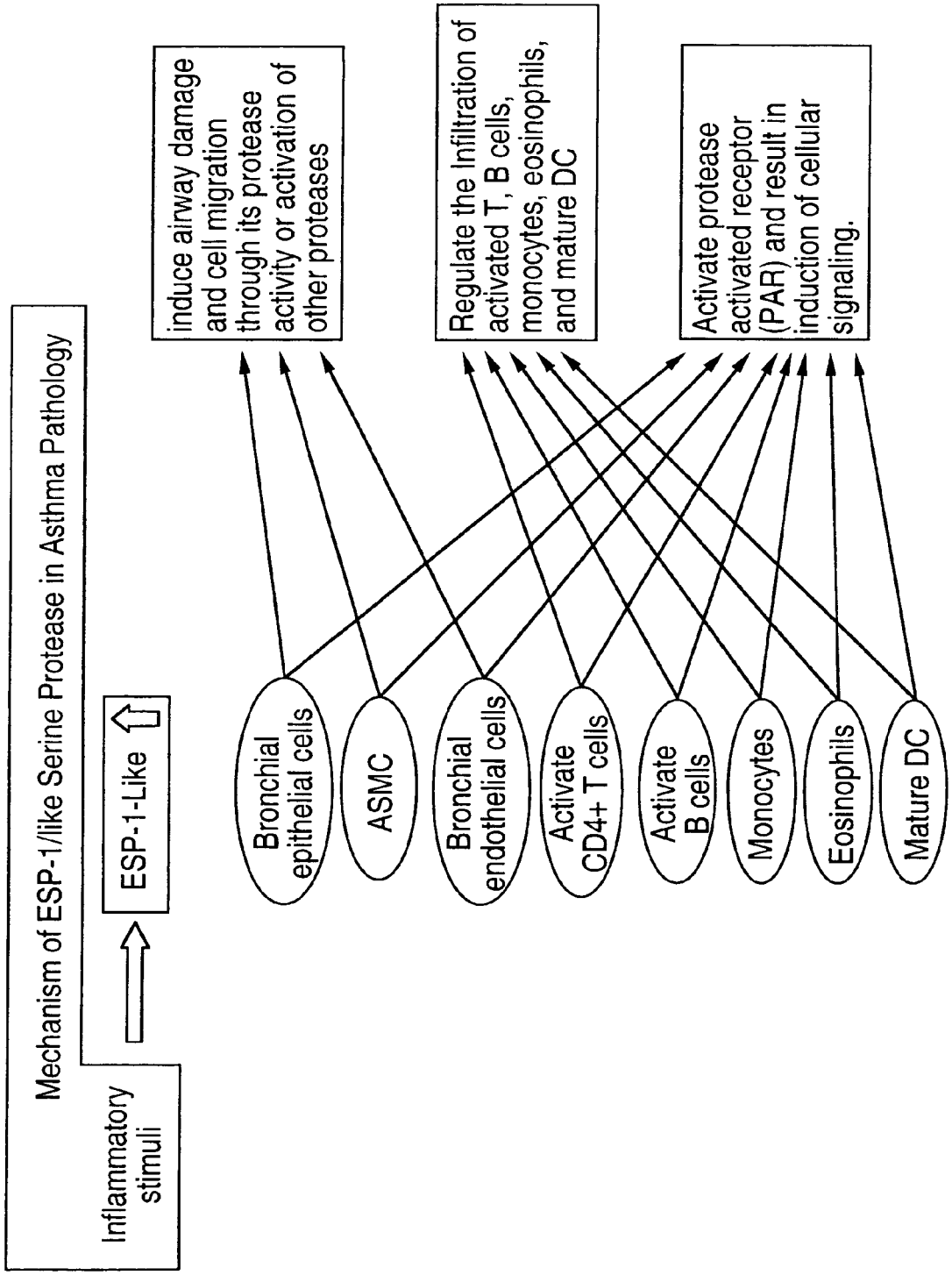

SEQUENCE LISTING

<160> NUMBER OF SEQ ID NOS: 58

<210> SEQ ID NO 1
<211> LENGTH: 837
<212> TYPE: DNA
<213> ORGANISM: Homo sapiens
<220> FEATURE:
<223> OTHER INFORMATION: BLOCKS domain

<400> SEQUENCE: 1

```
atgggcgcgc gcggggcgct gctgctggcg ctgctgctgg ctcgggctgg actcgggaag      60
ccggaggcct gcggccaccg ggaaattcac gcgctggtgg cgggcggagt ggagtccgcg     120
cgcgggcgct ggccatggca ggccagcctg cgcctgagga gacgccaccg atgtggaggg     180
agcctgctca gccgccgctg ggtgctctcg gctgcgcact gcttccaaaa ccaactcctt     240
ggaacctgcg gggcctacag cagtcgttac aaagtgcagg acatcattgt gaaccctgac     300
gcacttgggg ttttacgcaa tgacattgcc ctgctgagac tggcctcttc tgtcacctac     360
aatgcgtaca tccagcccat ttgcatcgag tcttccacct tcaacttcgt gcaccggccg     420
gactgctggg tgaccggctg ggggttaatc agcccagtg gcacacctct gccacctcct     480
tacaacctcc gggaagcaca ggtcaccatc ttaaacaaca ccaggtgtaa ttacctgttt     540
gaacagccct ctagccgtag tatgatctgg gattccatgt tttgtgctgg tgctgaggat     600
```

-continued

```
ggcagtgtag acacctgcaa aggtgactca ggtggaccct tggtctgtga caaggatgga    660
ctgtggtatc aggttggaat cgtgagctgg ggaatggact gcggtcaacc caatcggcct    720
ggtgtctaca ccaacatcag tgtgtacttc cactggatcc ggagggtgat gtcccacagt    780
acacccaggc caaacccctc ccagctgttg ctgctccttg ccctgctgtg ggctccc       837
```

<210> SEQ ID NO 2
<211> LENGTH: 279
<212> TYPE: PRT
<213> ORGANISM: Homo sapiens
<220> FEATURE:
<223> OTHER INFORMATION: BLOCKS domain

<400> SEQUENCE: 2

```
Met Gly Ala Arg Gly Ala Leu Leu Ala Leu Leu Leu Ala Arg Ala
 1               5                  10                  15

Gly Leu Gly Lys Pro Glu Ala Cys Gly His Arg Glu Ile His Ala Leu
                20                  25                  30

Val Ala Gly Val Glu Ser Ala Arg Gly Arg Trp Pro Trp Gln Ala
            35                  40                  45

Ser Leu Arg Leu Arg Arg Arg His Arg Cys Gly Gly Ser Leu Leu Ser
        50                  55                  60

Arg Arg Trp Val Leu Ser Ala Ala His Cys Phe Gln Asn Gln Leu Leu
 65                  70                  75                  80

Gly Thr Cys Gly Ala Tyr Ser Ser Arg Tyr Lys Val Gln Asp Ile Ile
                85                  90                  95

Val Asn Pro Asp Ala Leu Gly Val Leu Arg Asn Asp Ile Ala Leu Leu
            100                 105                 110

Arg Leu Ala Ser Ser Val Thr Tyr Asn Ala Tyr Ile Gln Pro Ile Cys
        115                 120                 125

Ile Glu Ser Ser Thr Phe Asn Phe Val His Arg Pro Asp Cys Trp Val
130                 135                 140

Thr Gly Trp Gly Leu Ile Ser Pro Ser Gly Thr Pro Leu Pro Pro Pro
145                 150                 155                 160

Tyr Asn Leu Arg Glu Ala Gln Val Thr Ile Leu Asn Asn Thr Arg Cys
                165                 170                 175

Asn Tyr Leu Phe Glu Gln Pro Ser Ser Arg Ser Met Ile Trp Asp Ser
            180                 185                 190

Met Phe Cys Ala Gly Ala Glu Asp Gly Ser Val Asp Thr Cys Lys Gly
        195                 200                 205

Asp Ser Gly Gly Pro Leu Val Cys Asp Lys Asp Gly Leu Trp Tyr Gln
    210                 215                 220

Val Gly Ile Val Ser Trp Gly Met Asp Cys Gly Gln Pro Asn Arg Pro
225                 230                 235                 240

Gly Val Tyr Thr Asn Ile Ser Val Tyr Phe His Trp Ile Arg Arg Val
                245                 250                 255

Met Ser His Ser Thr Pro Arg Pro Asn Pro Ser Gln Leu Leu Leu Leu
            260                 265                 270

Leu Ala Leu Leu Trp Ala Pro
        275
```

<210> SEQ ID NO 3
<211> LENGTH: 35
<212> TYPE: PRT
<213> ORGANISM: Artificial Sequence
<220> FEATURE:
<223> OTHER INFORMATION: BLOCKS domain -continued

```
<400> SEQUENCE: 3

Ala Gly Ala Glu Asp Gly Ser Val Asp Thr Cys Lys Gly Asp Ser Gly
 1               5                  10                  15

Gly Pro Leu Val Cys Asp Lys Asp Gly Leu Trp Tyr Gln Val Gly Ile
                20                  25                  30

Val Ser Trp
        35

<210> SEQ ID NO 4
<211> LENGTH: 17
<212> TYPE: PRT
<213> ORGANISM: Artificial Sequence
<220> FEATURE:
<223> OTHER INFORMATION: BLOCKS domain

<400> SEQUENCE: 4

Cys Gly Gly Ser Leu Leu Ser Arg Arg Trp Val Leu Ser Ala Ala His
 1               5                  10                  15

Cys

<210> SEQ ID NO 5
<211> LENGTH: 18
<212> TYPE: PRT
<213> ORGANISM: Artificial Sequence
<220> FEATURE:
<223> OTHER INFORMATION: BLOCKS domain

<400> SEQUENCE: 5

Cys Gly Gly Ser Leu Leu Ser Arg Arg Trp Val Leu Ser Ala Ala His
 1               5                  10                  15

Cys Phe

<210> SEQ ID NO 6
<211> LENGTH: 14
<212> TYPE: PRT
<213> ORGANISM: Artificial Sequence
<220> FEATURE:
<223> OTHER INFORMATION: BLOCKS domain

<400> SEQUENCE: 6

Val Asp Thr Cys Lys Gly Asp Ser Gly Gly Pro Leu Val Cys
 1               5                  10

<210> SEQ ID NO 7
<211> LENGTH: 42
<212> TYPE: PRT
<213> ORGANISM: Artificial Sequence
<220> FEATURE:
<223> OTHER INFORMATION: BLOCKS domain

<400> SEQUENCE: 7

Gly Pro Leu Val Cys Asp Lys Asp Gly Leu Trp Tyr Gln Val Gly Ile
 1               5                  10                  15

Val Ser Trp Gly Met Asp Cys Gly Gln Pro Asn Arg Pro Gly Val Tyr
                20                  25                  30

Thr Asn Ile Ser Val Tyr Phe His Trp Ile
        35                  40

<210> SEQ ID NO 8
<211> LENGTH: 35
<212> TYPE: PRT
<213> ORGANISM: Artificial Sequence
```

-continued

```
<220> FEATURE:
<223> OTHER INFORMATION: BLOCKS domain

<400> SEQUENCE: 8

Trp Tyr Gln Val Gly Ile Val Ser Trp Gly Met Asp Cys Gly Gln Pro
 1               5                  10                  15

Asn Arg Pro Gly Val Tyr Thr Asn Ile Ser Val Tyr Phe His Trp Ile
            20                  25                  30

Arg Arg Val
        35

<210> SEQ ID NO 9
<211> LENGTH: 24
<212> TYPE: PRT
<213> ORGANISM: Artificial Sequence
<220> FEATURE:
<223> OTHER INFORMATION: BLOCKS domain

<400> SEQUENCE: 9

Asp Thr Cys Lys Gly Asp Ser Gly Gly Pro Leu Val Cys Asp Lys Asp
 1               5                  10                  15

Gly Leu Trp Tyr Gln Val Gly Ile
            20

<210> SEQ ID NO 10
<211> LENGTH: 35
<212> TYPE: PRT
<213> ORGANISM: Artificial Sequence
<220> FEATURE:
<223> OTHER INFORMATION: BLOCKS domain

<400> SEQUENCE: 10

Val Thr Tyr Asn Ala Tyr Ile Gln Pro Ile Cys Ile Glu Ser Ser Thr
 1               5                  10                  15

Phe Asn Phe Val His Arg Pro Asp Cys Trp Val Thr Gly Trp Gly Leu
            20                  25                  30

Ile Ser Pro
        35

<210> SEQ ID NO 11
<211> LENGTH: 14
<212> TYPE: PRT
<213> ORGANISM: Artificial Sequence
<220> FEATURE:
<223> OTHER INFORMATION: BLOCKS domain

<400> SEQUENCE: 11

Cys Gly Gly Ser Leu Leu Ser Arg Arg Trp Val Leu Ser Ala
 1               5                  10

<210> SEQ ID NO 12
<211> LENGTH: 29
<212> TYPE: PRT
<213> ORGANISM: Artificial Sequence
<220> FEATURE:
<223> OTHER INFORMATION: BLOCKS domain

<400> SEQUENCE: 12

Gly Met Asp Cys Gly Gln Pro Asn Arg Pro Gly Val Tyr Thr Asn Ile
 1               5                  10                  15

Ser Val Tyr Phe His Trp Ile Arg Arg Val Met Ser His
            20                  25
```

<210> SEQ ID NO 13
<211> LENGTH: 14
<212> TYPE: PRT
<213> ORGANISM: Artificial Sequence
<220> FEATURE:
<223> OTHER INFORMATION: BLOCKS domain

<400> SEQUENCE: 13

Pro Gly Val Tyr Thr Asn Ile Ser Val Tyr Phe His Trp Ile
1               5                   10

<210> SEQ ID NO 14
<211> LENGTH: 314
<212> TYPE: PRT
<213> ORGANISM: Homo sapiens

<400> SEQUENCE: 14

Met Gly Ala Arg Gly Ala Leu Leu Ala Leu Leu Leu Ala Arg Ala
1               5                   10                  15

Gly Leu Arg Lys Pro Glu Ser Gln Glu Ala Ala Pro Leu Ser Gly Pro
                20                  25                  30

Cys Gly Arg Arg Val Ile Thr Ser Arg Ile Val Gly Gly Glu Asp Ala
            35                  40                  45

Glu Leu Gly Arg Trp Pro Trp Gln Gly Ser Leu Arg Leu Trp Asp Ser
50                  55                  60

His Val Cys Gly Val Ser Leu Leu Ser His Arg Trp Ala Leu Thr Ala
65                  70                  75                  80

Ala His Cys Phe Glu Thr Tyr Ser Asp Leu Ser Asp Pro Ser Gly Trp
                85                  90                  95

Met Val Gln Phe Gly Gln Leu Thr Ser Met Pro Ser Phe Trp Ser Leu
            100                 105                 110

Gln Ala Tyr Tyr Thr Arg Tyr Phe Val Ser Asn Ile Tyr Leu Ser Pro
        115                 120                 125

Arg Tyr Leu Gly Asn Ser Pro Tyr Asp Ile Ala Leu Val Lys Leu Ser
130                 135                 140

Ala Pro Val Thr Tyr Thr Lys His Ile Gln Pro Ile Cys Leu Gln Ala
145                 150                 155                 160

Ser Thr Phe Glu Phe Glu Asn Arg Thr Asp Cys Trp Val Thr Gly Trp
                165                 170                 175

Gly Tyr Ile Lys Glu Asp Glu Ala Leu Pro Ser Pro His Thr Leu Gln
            180                 185                 190

Glu Val Gln Val Ala Ile Ile Asn Asn Ser Met Cys Asn His Leu Phe
        195                 200                 205

Leu Lys Tyr Ser Phe Arg Lys Asp Ile Phe Gly Asp Met Val Cys Ala
210                 215                 220

Gly Asn Ala Gln Gly Gly Lys Asp Ala Cys Phe Gly Asp Ser Gly Gly
225                 230                 235                 240

Pro Leu Ala Cys Asn Lys Asn Gly Leu Trp Tyr Gln Ile Gly Val Val
                245                 250                 255

Ser Trp Gly Val Gly Cys Gly Arg Pro Asn Arg Pro Gly Val Tyr Thr
            260                 265                 270

Asn Ile Ser His His Phe Glu Trp Ile Gln Lys Leu Met Ala Gln Ser
        275                 280                 285

Gly Met Ser Gln Pro Asp Pro Ser Trp Pro Leu Leu Phe Phe Pro Leu
    290                 295                 300

Leu Trp Ala Leu Pro Leu Leu Gly Pro Val
305                 310

<210> SEQ ID NO 15
<211> LENGTH: 233
<212> TYPE: DNA
<213> ORGANISM: Homo sapiens

<400> SEQUENCE: 15

| | | | | |
|---|---|---|---|---|
| ccaactcctt ggaacctgcg gggcctacag cagtcgttac aaagtgcagg acatcattgt | 60 |
| gaaccctgac gcacttgggg ttttacgcaa tgacattgcc ctgctgagac tggcctcttc | 120 |
| tgtcacctac aatgcgtaca tccagcccat ttgcatcgag tcttccacct tcaacttcgt | 180 |
| gcaccggccg gactgctggg tgaccggctg ggggttaatc agccccagtg gca | 233 |

<210> SEQ ID NO 16
<211> LENGTH: 216
<212> TYPE: DNA
<213> ORGANISM: Homo sapiens

<400> SEQUENCE: 16

| | |
|---|---|
| ggtgactcag gtggacccctt ggtctgtgac aaggatggac tgtggtatca ggttggaatc | 60 |
| gtgagctggg gaatggactg cggtcaaccc aatcggcctg gtgtctacac caacatcagt | 120 |
| gtgtacttcc actggatccg gagggtgatg tcccacagta cacccaggcc aaaccccctcc | 180 |
| cagctgttgc tgctccttgc cctgctgtgg gctccc | 216 |

<210> SEQ ID NO 17
<211> LENGTH: 167
<212> TYPE: DNA
<213> ORGANISM: Homo sapiens

<400> SEQUENCE: 17

| | |
|---|---|
| gaggcctgcg gccaccggga aattcacgcg ctggtggcgg gcggagtgga gtccgcgcgc | 60 |
| gggcgctggc catggcaggc cagcctgcgc ctgaggagac gccaccgatg tggagggagc | 120 |
| ctgctcagcc gccgctgggt gctctcggct gcgcactgct tccaaaa | 167 |

<210> SEQ ID NO 18
<211> LENGTH: 159
<212> TYPE: DNA
<213> ORGANISM: Homo sapiens

<400> SEQUENCE: 18

| | |
|---|---|
| cacctctgcc acctccttac aacctccggg aagcacaggt caccatctta acaacacca | 60 |
| ggtgtaatta cctgtttgaa cagccctcta gccgtagtat gatctgggat tccatgtttt | 120 |
| gtgctggtgc tgaggatggc agtgtagaca cctgcaaag | 159 |

<210> SEQ ID NO 19
<211> LENGTH: 1082
<212> TYPE: DNA
<213> ORGANISM: Homo sapiens

<400> SEQUENCE: 19

| | |
|---|---|
| gaggaggcca tgggcgcgcg cggggcgctg ctgctggcgc tgctgctggc tcgggctgga | 60 |
| ctcaggaagc cggagtcgca ggaggcggcg ccgttatcag gaccatgcgg ccgacgggtc | 120 |
| atcacgtcgc gcatcgtggg tggagaggac gccgaactcg gcgttggcc gtggcagggg | 180 |
| agcctgcgcc tgtgggattc ccacgtatgc ggagtgagcc tgctcagcca ccgctgggca | 240 |
| ctcacgcgg cgcactgctt tgaaacctat agtgacctta gtgatccctc cgggtggatg | 300 |
| gtccagtttg ccagctgac ttccatgcca tccttctgga gcctgcaggc ctactacacc | 360 |

| | |
|---|---|
| cgttacttcg tatcgaatat ctatctgagc cctcgctacc tggggaattc accctatgac | 420 |
| attgccttgg tgaagctgtc tgcacctgtc acctacacta aacacatcca gcccatctgc | 480 |
| ctccaggcct ccacatttga gtttgagaac cggacagact gctgggtgac tggctggggg | 540 |
| tacatcaaag aggatgaggc actgccatct ccccacaccc tccaggaagt tcaggtcgcc | 600 |
| atcataaaca actctatgtg caaccacctc ttcctcaagt acagtttccg caaggacatc | 660 |
| tttggagaca tggtttgtgc tggcaatgcc aaggcggga aggatgcctg cttcggtgac | 720 |
| tcaggtggac ccttggcctg taacaagaat ggactgtggt atcagattgg agtcgtgagc | 780 |
| tggggagtgg gctgtggtcg cccaatcggc ccggtgtct acaccaatat cagccaccac | 840 |
| tttgagtgga tccagaagct gatggcccag agtggcatgt cccagccaga cccctcctgg | 900 |
| ccactactct ttttccctct tctctgggct ctcccactcc tggggccggt ctgagcctac | 960 |
| ctgagcccat gcagcctggg gccactgcca agtcaggccc tggttctctt ctgtcttgtt | 1020 |
| tggtaataaa cacattccag ttgatgcctt gcagggcatt cttcaaaaaa aaaaaaaaa | 1080 |
| aa | 1082 |

<210> SEQ ID NO 20
<211> LENGTH: 1077
<212> TYPE: DNA
<213> ORGANISM: Homo sapiens

<400> SEQUENCE: 20

| | |
|---|---|
| gccgcgggag aggaggccat gggcgcgcgc ggggcgctgc tgctggcgct gctgctggct | 60 |
| cgggctggac tcaggaagcc ggagtcgcag gaggcggcgc cgttatcagg accatgcggc | 120 |
| cgacgggtca tcacgtcgcg catcgtgggt ggagaggacg ccgaactcgg gcgttggccg | 180 |
| tggcagggga gcctgcgcct gtgggattcc cacgtatgcg gagtgagcct gctcagccac | 240 |
| cgctgggcac tcacggcggc gcactgcttt gaaacctata gtgaccttag tgatccctcc | 300 |
| gggtggatgg tccagtttgg ccagctgact tccatgccat ccttctggag cctgcaggcc | 360 |
| tactacaccc gttacttcgt atcgaatatc tatctgagcc ctcgctacct ggggaattca | 420 |
| ccctatgaca ttgccttggt gaagctgtct gcacctgtca cctacactaa acacatccag | 480 |
| cccatctgtc tccaggcctc cacatttgag tttgagaacc ggacagactg ctgggtgact | 540 |
| ggctggggt acatcaaaga ggatgaggca ctgccatctc cccacaccct ccaggaagtt | 600 |
| caggtcgcca tcataaacaa ctctatgtgc aaccacctct tcctcaagta cagtttccgc | 660 |
| aaggacatct ttggagacat ggtttgtgct ggcaatgccc aaggcgggaa ggatgcctgc | 720 |
| ttcggtgact caggtggacc cttggcctgt aacaagaatg gactgtggta tcagattgga | 780 |
| gtcgtgagct ggggagtggg ctgtggtcgc ccaatcggc ccggtgtcta caccaatatc | 840 |
| agccaccact ttgagtggat ccagaagctg atggcccaga gtggcatgtc ccagccagac | 900 |
| ccctcctggc cgctactctt tttccctctt ctctgggctc tcccactcct ggggccggtc | 960 |
| tgagcctacc tgagcccatg cagcctgggg ccactgccaa gtcaggccct ggttctcttc | 1020 |
| tgtcttgttt ggtaataaac acattccagt tgatgccttg cagggcattc ttcaaaa | 1077 |

<210> SEQ ID NO 21
<211> LENGTH: 393
<212> TYPE: DNA
<213> ORGANISM: Homo sapiens

```
<400> SEQUENCE: 21
gaacatgcac acgtatttat tagcaaacga gacaaaaggg gccggaatct gatccagcag    60
gcagtcccaa ccctgtccct gaagcgccca cagcccagag gaggtgagcc aatactgtgg   120
tccccactgc agcctcacag tttctggtgc actcagaatg gctgcaggag tcagggagcc   180
cacagcaggg caaggagcag caacagctgg ggagggtttt ggccttggtg tactgtggga   240
catcaccctc cggatccagt ggaagtacac actgatgttg gtgtagacac caggccgatt   300
gggttgaccg cagtccattc cccagctcac gattccaacc tgataccaca gtccatcctt   360
gtcacagacc aagggtccac ctgagtcacc ctg                                 393

<210> SEQ ID NO 22
<211> LENGTH: 24
<212> TYPE: DNA
<213> ORGANISM: Homo sapiens

<400> SEQUENCE: 22
attgcgtaaa accccaagtg cgtc                                            24

<210> SEQ ID NO 23
<211> LENGTH: 21
<212> TYPE: DNA
<213> ORGANISM: Homo sapiens

<400> SEQUENCE: 23
tgagctcggg gcgctacagg c                                               21

<210> SEQ ID NO 24
<211> LENGTH: 24
<212> TYPE: DNA
<213> ORGANISM: Homo sapiens

<400> SEQUENCE: 24
aagccggagt cgcaggagga ggag                                            24

<210> SEQ ID NO 25
<211> LENGTH: 20
<212> TYPE: DNA
<213> ORGANISM: Homo sapiens

<400> SEQUENCE: 25
gcggggcgct ggccatggca                                                 20

<210> SEQ ID NO 26
<211> LENGTH: 24
<212> TYPE: DNA
<213> ORGANISM: Homo sapiens

<400> SEQUENCE: 26
cccaactgct tccccctctg ttct                                            24

<210> SEQ ID NO 27
<211> LENGTH: 24
<212> TYPE: DNA
<213> ORGANISM: Homo sapiens

<400> SEQUENCE: 27
ggcagcgagt gtccttctca tggt                                            24
```

```
<210> SEQ ID NO 28
<211> LENGTH: 24
<212> TYPE: DNA
<213> ORGANISM: Homo sapiens

<400> SEQUENCE: 28
ccaccgggaa cgaaagagaa gctc                                          24

<210> SEQ ID NO 29
<211> LENGTH: 24
<212> TYPE: DNA
<213> ORGANISM: Homo sapiens

<400> SEQUENCE: 29
ggctgagatg ccgtcgagga tgta                                          24

<210> SEQ ID NO 30
<211> LENGTH: 24
<212> TYPE: DNA
<213> ORGANISM: Homo sapiens

<400> SEQUENCE: 30
aaattgaggc caagggccaa gaga                                          24

<210> SEQ ID NO 31
<211> LENGTH: 25
<212> TYPE: DNA
<213> ORGANISM: Homo sapiens

<400> SEQUENCE: 31
ggagaaacca aggcacagtg gaaca                                         25

<210> SEQ ID NO 32
<211> LENGTH: 24
<212> TYPE: DNA
<213> ORGANISM: Homo sapiens

<400> SEQUENCE: 32
gatccagctt ccaagtgcca ctgc                                          24

<210> SEQ ID NO 33
<211> LENGTH: 24
<212> TYPE: DNA
<213> ORGANISM: Homo sapiens

<400> SEQUENCE: 33
gtggtttggt tgcatggctg ttca                                          24

<210> SEQ ID NO 34
<211> LENGTH: 24
<212> TYPE: DNA
<213> ORGANISM: Homo sapiens

<400> SEQUENCE: 34
gaaaccaggg agccccttttg atga                                         24

<210> SEQ ID NO 35
<211> LENGTH: 24
<212> TYPE: DNA
<213> ORGANISM: Homo sapiens

<400> SEQUENCE: 35
acggggtttc accatgttga ccag                                          24
```

-continued

```
<210> SEQ ID NO 36
<211> LENGTH: 22
<212> TYPE: DNA
<213> ORGANISM: Homo sapiens

<400> SEQUENCE: 36
ccatattcct cggacaccac ac                                              22

<210> SEQ ID NO 37
<211> LENGTH: 24
<212> TYPE: DNA
<213> ORGANISM: Homo sapiens

<400> SEQUENCE: 37
aactcctgac ctcaagtgat ccac                                            24

<210> SEQ ID NO 38
<211> LENGTH: 24
<212> TYPE: DNA
<213> ORGANISM: Homo sapiens

<400> SEQUENCE: 38
acacagccct gggagcatgt gaat                                            24

<210> SEQ ID NO 39
<211> LENGTH: 24
<212> TYPE: DNA
<213> ORGANISM: Homo sapiens

<400> SEQUENCE: 39
cacaggaagt ttccggggtt ggag                                            24

<210> SEQ ID NO 40
<211> LENGTH: 24
<212> TYPE: DNA
<213> ORGANISM: Homo sapiens

<400> SEQUENCE: 40
gtttgtttct cccctgggc tctg                                             24

<210> SEQ ID NO 41
<211> LENGTH: 24
<212> TYPE: DNA
<213> ORGANISM: Homo sapiens

<400> SEQUENCE: 41
cacctggcct gaggtgatgc tttc                                            24

<210> SEQ ID NO 42
<211> LENGTH: 24
<212> TYPE: DNA
<213> ORGANISM: Homo sapiens

<400> SEQUENCE: 42
agcagcagca gcagcaacaa caac                                            24

<210> SEQ ID NO 43
<211> LENGTH: 24
<212> TYPE: DNA
<213> ORGANISM: Homo sapiens

<400> SEQUENCE: 43
ccttgctgag gacagaaggg agca                                            24
```

```
<210> SEQ ID NO 44
<211> LENGTH: 24
<212> TYPE: DNA
<213> ORGANISM: Homo sapiens

<400> SEQUENCE: 44
gattgaggct gggagacagc cgta                                          24

<210> SEQ ID NO 45
<211> LENGTH: 24
<212> TYPE: DNA
<213> ORGANISM: Homo sapiens

<400> SEQUENCE: 45
cacttcccca ctcccagact gcat                                          24

<210> SEQ ID NO 46
<211> LENGTH: 24
<212> TYPE: DNA
<213> ORGANISM: Homo sapiens

<400> SEQUENCE: 46
ttggaaatga ctgtgagcgg agca                                          24

<210> SEQ ID NO 47
<211> LENGTH: 24
<212> TYPE: DNA
<213> ORGANISM: Homo sapiens

<400> SEQUENCE: 47
agagttccgg ctctgctgtg gatg                                          24

<210> SEQ ID NO 48
<211> LENGTH: 24
<212> TYPE: DNA
<213> ORGANISM: Homo sapiens

<400> SEQUENCE: 48
tgatctttgc cgtggtggtc ctct                                          24

<210> SEQ ID NO 49
<211> LENGTH: 24
<212> TYPE: DNA
<213> ORGANISM: Homo sapiens

<400> SEQUENCE: 49
acaaaaaggc ccctgcaggt tttg                                          24

<210> SEQ ID NO 50
<211> LENGTH: 24
<212> TYPE: DNA
<213> ORGANISM: Homo sapiens

<400> SEQUENCE: 50
ccccatcatc ttcgggatcc tgtt                                          24

<210> SEQ ID NO 51
<211> LENGTH: 24
<212> TYPE: DNA
<213> ORGANISM: Homo sapiens

<400> SEQUENCE: 51
ggtgggtgca gcctcactgt ctct                                          24
```

```
<210> SEQ ID NO 52
<211> LENGTH: 24
<212> TYPE: DNA
<213> ORGANISM: Homo sapiens

<400> SEQUENCE: 52
ttgggagtcc aggagagcct caga                                            24

<210> SEQ ID NO 53
<211> LENGTH: 24
<212> TYPE: DNA
<213> ORGANISM: Homo sapiens

<400> SEQUENCE: 53
tgcagcactt ccattacgtt gcac                                            24

<210> SEQ ID NO 54
<211> LENGTH: 21
<212> TYPE: DNA
<213> ORGANISM: Homo sapiens

<400> SEQUENCE: 54
atgggcgcgc gcggggcgct g                                               21

<210> SEQ ID NO 55
<211> LENGTH: 22
<212> TYPE: DNA
<213> ORGANISM: Homo sapiens

<400> SEQUENCE: 55
gggagcccac agcagggcaa gg                                              22

<210> SEQ ID NO 56
<211> LENGTH: 334
<212> TYPE: PRT
<213> ORGANISM: Homo sapiens

<400> SEQUENCE: 56
```

Met Gly Ala Arg Gly Ala Leu Leu Leu Ala Leu Leu Leu Ala Arg Ala
 1               5                  10                  15

Gly Leu Gly Lys Pro Gly Glu Leu Gly Ala Leu Gln Ala Gly Pro Gly
                20                  25                  30

Ala Ala Arg Arg Pro Gly Gly Gly Arg Glu Gly His Phe Leu Cys
             35                  40                  45

Pro Ala Glu Ser Gln Glu Glu Leu Leu Ser Glu Ala Cys Gly His
     50                  55                  60

Arg Glu Ile His Ala Leu Val Ala Gly Val Glu Ser Ala Arg Gly
65                   70                  75                  80

Arg Trp Pro Trp Gln Ala Ser Leu Arg Leu Arg Arg His Arg Cys
                85                  90                  95

Gly Gly Ser Leu Leu Ser Arg Arg Trp Val Leu Ser Ala Ala His Cys
                100                 105                 110

Phe Gln Lys His Tyr Tyr Pro Ser Glu Trp Thr Val Gln Leu Gly Glu
            115                 120                 125

Leu Thr Ser Arg Pro Thr Pro Trp Asn Leu Arg Ala Tyr Ser Ser Arg
        130                 135                 140

Tyr Lys Val Gln Asp Ile Ile Val Asn Pro Asp Ala Leu Gly Val Leu
145                 150                 155                 160

Arg Asn Asp Ile Ala Leu Leu Arg Leu Ala Ser Ser Val Thr Tyr Asn
                165                 170                 175

```
Ala Tyr Ile Gln Pro Ile Cys Ile Glu Ser Ser Thr Phe Asn Phe Val
            180                 185                 190

His Arg Pro Asp Cys Trp Val Thr Gly Trp Gly Leu Ile Ser Pro Ser
        195                 200                 205

Gly Thr Pro Leu Pro Pro Tyr Asn Leu Arg Glu Ala Gln Val Thr
    210                 215                 220

Ile Leu Asn Asn Thr Arg Cys Asn Tyr Leu Phe Glu Gln Pro Ser Ser
225                 230                 235                 240

Arg Ser Met Ile Trp Asp Ser Met Phe Cys Ala Gly Ala Glu Asp Gly
                245                 250                 255

Ser Val Asp Thr Cys Lys Gly Asp Ser Gly Gly Pro Leu Val Cys Asp
            260                 265                 270

Lys Asp Gly Leu Trp Tyr Gln Val Gly Ile Val Ser Trp Gly Met Asp
        275                 280                 285

Cys Gly Gln Pro Asn Arg Pro Gly Val Tyr Thr Asn Ile Ser Val Tyr
    290                 295                 300

Phe His Trp Ile Arg Arg Val Met Ser His Ser Thr Pro Arg Pro Asn
305                 310                 315                 320

Pro Ser Gln Leu Leu Leu Leu Ala Leu Leu Trp Ala Pro
                325                 330

<210> SEQ ID NO 57
<211> LENGTH: 305
<212> TYPE: PRT
<213> ORGANISM: Homo sapiens

<400> SEQUENCE: 57

Met Gly Ala Arg Gly Ala Leu Leu Ala Leu Leu Leu Ala Arg Ala
1               5                   10                  15

Gly Leu Gly Lys Pro Glu Ser Gln Glu Glu Leu Leu Ser Glu Ala
        20                  25                  30

Cys Gly His Arg Glu Ile His Ala Leu Val Ala Gly Val Glu Ser
    35                  40                  45

Ala Arg Gly Arg Trp Pro Trp Gln Ala Ser Leu Arg Leu Arg Arg Arg
50                  55                  60

His Arg Cys Gly Gly Ser Leu Leu Ser Arg Arg Trp Val Leu Ser Ala
65                  70                  75                  80

Ala His Cys Phe Gln Lys His Tyr Tyr Pro Ser Glu Trp Thr Val Gln
                85                  90                  95

Leu Gly Glu Leu Thr Ser Arg Pro Thr Pro Trp Asn Leu Arg Ala Tyr
                100                 105                 110

Ser Ser Arg Tyr Lys Val Gln Asp Ile Ile Val Asn Pro Asp Ala Leu
        115                 120                 125

Gly Val Leu Arg Asn Asp Ile Ala Leu Leu Arg Leu Ala Ser Ser Val
    130                 135                 140

Thr Tyr Asn Ala Tyr Ile Gln Pro Ile Cys Ile Glu Ser Ser Thr Phe
145                 150                 155                 160

Asn Phe Val His Arg Pro Asp Cys Trp Val Thr Gly Trp Gly Leu Ile
                165                 170                 175

Ser Pro Ser Gly Thr Pro Leu Pro Pro Tyr Asn Leu Arg Glu Ala
                180                 185                 190

Gln Val Thr Ile Leu Asn Asn Thr Arg Cys Asn Tyr Leu Phe Glu Gln
        195                 200                 205

Pro Ser Ser Arg Ser Met Ile Trp Asp Ser Met Phe Cys Ala Gly Ala
    210                 215                 220
```

-continued

Glu Asp Gly Ser Val Asp Thr Cys Lys Gly Asp Ser Gly Pro Leu
225                 230                 235                 240

Val Cys Asp Lys Asp Gly Leu Trp Tyr Gln Val Gly Ile Val Ser Trp
            245                 250                 255

Gly Met Asp Cys Gly Gln Pro Asn Arg Pro Gly Val Tyr Thr Asn Ile
            260                 265                 270

Ser Val Tyr Phe His Trp Ile Arg Arg Val Met Ser His Ser Thr Pro
            275                 280                 285

Arg Pro Asn Pro Ser Gln Leu Leu Leu Leu Ala Leu Leu Trp Ala
        290                 295                 300

Pro
305

<210> SEQ ID NO 58
<211> LENGTH: 260
<212> TYPE: PRT
<213> ORGANISM: Homo sapiens

<400> SEQUENCE: 58

Met Gly Ala Arg Gly Ala Trp Pro Trp Gln Ala Ser Leu Arg Leu Arg
1               5                   10                  15

Arg Arg His Arg Cys Gly Gly Ser Leu Leu Ser Arg Arg Trp Val Leu
            20                  25                  30

Ser Ala Ala His Cys Phe Gln Lys His Tyr Tyr Pro Ser Glu Trp Thr
        35                  40                  45

Val Gln Leu Gly Glu Leu Thr Ser Arg Pro Thr Pro Trp Asn Asn Leu
    50                  55                  60

Arg Ala Tyr Ser Ser Arg Tyr Lys Val Gln Asp Ile Ile Val Asn Pro
65                  70                  75                  80

Asp Ala Leu Gly Val Leu Arg Asn Asp Ile Ala Leu Leu Arg Leu Ala
                85                  90                  95

Ser Ser Val Thr Tyr Asn Ala Tyr Ile Gln Pro Ile Cys Ile Glu Ser
            100                 105                 110

Ser Thr Phe Asn Phe Val His Arg Pro Asp Cys Trp Val Thr Gly Trp
        115                 120                 125

Gly Leu Ile Ser Pro Ser Gly Thr Pro Leu Pro Pro Pro Tyr Asn Leu
    130                 135                 140

Arg Glu Ala Gln Val Thr Ile Leu Asn Asn Thr Arg Cys Asn Tyr Leu
145                 150                 155                 160

Phe Glu Gln Pro Ser Ser Arg Ser Met Ile Trp Asp Ser Met Phe Cys
                165                 170                 175

Ala Gly Ala Glu Asp Gly Ser Val Asp Thr Cys Lys Gly Asp Ser Gly
            180                 185                 190

Gly Pro Leu Val Cys Asp Lys Asp Gly Leu Trp Tyr Gln Val Gly Ile
        195                 200                 205

Val Ser Trp Gly Met Asp Cys Gly Gln Pro Asn Arg Pro Gly Val Tyr
    210                 215                 220

Thr Asn Ile Ser Val Tyr Phe His Trp Ile Arg Arg Val Met Ser His
225                 230                 235                 240

Ser Thr Pro Arg Pro Asn Pro Ser Gln Leu Leu Leu Leu Ala Leu
                245                 250                 255

Leu Trp Ala Pro
            260

REGULATION OF HUMAN EOSINOPHIL SERINE PROTEASE 1-LIKE ENZYME

This application is a division of application Ser. No. 09/885,441 filed Jun. 21, 2001, now abandoned which claims the benefit of provisional applications Ser. No. 60/212,844 filed Jun. 21, 2000, 60/244,171 filed Oct. 31, 2000, and 60/279,766 filed Mar. 30, 2001, and PCT application PCT/EP01/06936 filed Jun. 20, 2001. Each of these applications is incorporated by reference herein in its entirety.

TECHNICAL FIELD OF THE INVENTION

The invention relates to the regulation of a human eosinophil serine protease 1-like enzyme.

BACKGROUND OF THE INVENTION

Serine proteases are members of a family of proteolytic enzymes characterized by the presence of a cardinal serine in the catalytic site. They play important metabolic and cellular functions. Blood cells in particular are known to express serine proteases, with each protease playing a specific role in acute and chronic inflammation and in tissue remodeling. Eosinophil blood cells are involved in the modulation of respiratory immune responses, hypersensitivity, and tissue remodeling.

A serine protease gene (esp-1) from a human eosinophil has recently been cloned and characterized from patients with eosinophilia. See Inoue et al., *Biochem. Biophys. Res. Commun.* 252: 307–312 (1998) and Inoue et al., *Biochem. Biophys. Res. Commun.* 266: 564–568 (1999). Eosinophils are widely distributed within the human body and are found in the respiratory system, in skeletal muscle, and in cartilage. The esp-1 enzyme was identified as a serine protease by its homology with known serine proteases. Id., Davis et al., *Adv. Enzymol.* 48: 277–318 (1979), and Kohno et al., *Biochem. Biophys. Res. Commun.* 245: 658–665. Esp-1 mRNA was detected in a number of tissues, but only weakly in peripheral blood leukocytes, and not on kidney nor skeletal muscle, but highly expressed in testis. Therefore, it was expected that this particular serine protease is involved in fertilization processes. See Inoue (1998), supra. The genomic sequence was identified on chromosome 16, at p13.3. An expressed but presumably non-functional splicing variant was also reported. See Inoue (1999), supra. An additional esp-1 protein designated testisin was reported and is expected to also relate to human fertility. See Hooper et al., *Cancer Res.* 59: 3199–3205 (1999). Because of the involvement of serine proteases in a variety of biological functions, there is a continuing need to identify additional eosinophil-derived serine proteases which can be regulated to provide therapeutic effects.

SUMMARY OF THE INVENTION

It is an object of the present invention to provide reagents and methods for regulating a human eosinophil-1-like enzyme. This and other objectives of the invention are provided by one of the embodiments described below.

One embodiment of the invention is a cDNA encoding a polypeptide comprising an amino acid sequence selected from the group consisting of (a) the amino acid sequences shown in SEQ ID NOS:2, 56, 57, and 58 and (b) biologically active variants thereof.

Another embodiment of the invention is an expression vector comprising a polynucleotide which encodes a polypeptide comprising an amino acid sequence selected from the group consisting of (a) the amino acid sequence shown in SEQ ID NO:2 and (b) biologically active variants thereof.

Still another embodiment of the invention is a host cell comprising an expression vector which encodes a polypeptide comprising an amino acid sequence selected from the group consisting of (a) the amino acid sequences shown in SEQ ID NOS:2, 56, 57, and 58 and (b) biologically active variants thereof.

Yet another embodiment of the invention is a purified polypeptide comprising an amino acid sequence selected from the group consisting of (a) the amino acid sequences shown in SEQ ID NOS:2, 56, 57, and 58 and (b) biologically active variants thereof.

A further embodiment of the invention is a fusion protein comprising a polypeptide consisting of an amino acid sequence selected from the group consisting of (a) the amino acid sequences shown in SEQ ID NOS:2, 56, 57, and 58 and (b) biologically active variants thereof.

Even another embodiment of the invention is a method of producing a polypeptide comprising an amino acid sequence selected from the group consisting of (a) the amino acid sequences shown in SEQ ID NOS:2, 56, 57, and 58 and (b) biologically active variants thereof. A host cell comprising an expression vector that encodes the polypeptide is cultured under conditions whereby the polypeptide is expressed. The polypeptide is isolated.

Still another embodiment of the invention is a method of detecting a coding sequence for a polypeptide comprising an amino acid sequence selected from the group consisting of (a) the amino acid sequences shown in SEQ ID NOS:2, 56, 57, and 58 and (b) biologically active variants thereof. A polynucleotide comprising 11 contiguous nucleotides is hybridized to nucleic acid material of a biological sample to form a hybridization complex. The hybridization complex is detected. The polynucleotide is selected from the group consisting of (a) the complement of the nucleotide sequence shown in SEQ ID NO: 1, (b) a polynucleotide that hybridizes under stringent. conditions to (a), (c) a polynucleotide having a nucleic acid sequence that deviates from the nucleic acid sequences specified in (a) and (c) due to the degeneration of the genetic code, and (d) a polynucleotide that represents a fragment, derivative, or allelic variation of a nucleic acid sequence specified in (a) to (c)

Another embodiment of the invention is a kit for detecting a coding sequence for a polypeptide comprising an amino acid sequence selected from the group consisting of (a) the amino acid sequences shown in SEQ ID NOS:2, 56, 57, and 58 and (b) biologically active variants thereof. The kit comprises a polynucleotide and instructions for detecting the coding sequence. The polynucleotide comprises 11 contiguous nucleotides selected from the group consisting of (a) the complement of the nucleotide sequence shown in SEQ ID NO:1, (b) a polynucleotide that hybridizes under stringent conditions to (a), (c) a polynucleotide having a nucleic acid sequence that deviates from the nucleic acid sequences specified in (a) and (c) due to the degeneration of the genetic code, and (d) a polynucleotide that represents a fragment, derivative, or allelic variation of a nucleic acid sequence specified in (a) to (c).

A further embodiment of the invention is a method of detecting a polypeptide comprising an amino acid sequence selected from the group consisting of (a) the amino acid sequences shown in SEQ ID NOS:2, 56, 57, and 58 and (b)

biologically active variants thereof. A biological sample is contacted with a reagent that specifically binds to the polypeptide to form a reagent-polypeptide complex. The reagent-polypeptide complex is detected.

Even another embodiment of the invention is a kit for detecting a polypeptide comprising an amino acid sequence selected from the group consisting of (a) the amino acid sequences shown in SEQ ID NOS:2, 56, 57, and 58 and (b) biologically active variants thereof. The kit comprises an antibody which specifically binds to the polypeptide and instructions for detecting the polypeptide.

Yet another embodiment of the invention is a method of screening for agents that can regulate an activity of a human eosinophil serine protease 1-like enzyme. A test compound is contacted with a polypeptide comprising an amino acid sequence selected from the group consisting of (a) the amino acid sequences shown in SEQ ID NOS:2, 56, 57, and 58 and (b) biologically active variants thereof. Binding of the test compound to the polypeptide is detected. A test compound that binds to the polypeptide is thereby identified as a potential agent for regulating the activity of the human eosinophil serine protease 1-like enzyme.

Yet another embodiment of the invention is a method of screening for therapeutic agents that can regulate an enzymatic activity of a human eosinophil serine protease 1-like enzyme. A test compound is contacted with a polypeptide comprising an amino acid sequence selected from the group consisting of (a) the amino acid sequences shown in SEQ ID NOS:2, 56, 57, and 58 and (b) biologically active variants thereof. The enzymatic activity of the polypeptide is detected. A test compound that increases the enzymatic activity of the polypeptide is thereby identified as a potential therapeutic agent for increasing the enzymatic activity of the human eosinophil serine protease 1-like enzyme. A test compound that decreases the enzymatic activity of the polypeptide is thereby identified as a potential therapeutic agent for decreasing the enzymatic activity of the human eosinophil serine protease 1-like enzyme.

Still another embodiment of the invention is a method of screening for therapeutic agents that can regulate an activity of a human eosinophil serine protease 1-like enzyme. A test compound is contacted with a product encoded by a polynucleotide comprising a nucleotide sequence selected from the group consisting of (a) the amino acid sequences shown in SEQ ID NOS:2, 56, 57, and 58 and (b) biologically active variants thereof. Binding of the test compound to the product is detected. A test compound that binds to the product is thereby identified as a potential therapeutic agent for regulating the activity of the human eosinophil serine protease 1-like enzyme.

Yet another embodiment of the invention is a method of reducing an activity of a human eosinophil serine protease 1-like enzyme. A cell comprising the human eosinophil serine protease 1-like enzyme is contacted with a reagent that specifically binds to a product encoded by a polynucleotide comprising a nucleotide sequence selected from the group consisting of (a) the amino acid sequences shown in SEQ ID NOS:2, 56, 57, and 58 and (b) biologically active variants thereof. The activity of the human eosinophil serine protease 1-like enzyme is thereby reduced.

Another embodiment of the invention is a pharmaceutical composition comprising a reagent that specifically binds to a polypeptide comprising an amino acid sequence selected from the group consisting of (a) the amino acid sequences shown in SEQ ID NOS:2, 56, 57, and 58 and (b) biologically active variants thereof and a pharmaceutically acceptable carrier.

A further embodiment of the invention is a pharmaceutical composition comprising a reagent that specifically binds to a product of a polynucleotide comprising a coding sequence selected from the group consisting of (a) the amino acid sequences shown in SEQ ID NOS:2, 56, 57, and 58 and (b) biologically active variants thereof and a pharmaceutically acceptable carrier.

Even another embodiment of the invention is a pharmaceutical composition comprising an expression vector encoding a polypeptide comprising an amino acid sequence selected from the group consisting of (a) the amino acid sequences shown in SEQ ID NOS:2, 56, 57, and 58 and (b) biologically active variants thereof and a pharmaceutically acceptable carrier.

Still another embodiment of the invention is a method of treating a disorder selected from the group consisting of asthma, COPD, airway allergy, and osteoporosis. A therapeutically effective dose of a reagent that inhibits a function of a human eosinophil serine protease 1-like enzyme is administered to a patient in need thereof. The human eosinophil serine protease 1-like enzyme comprises an amino acid sequence selected from the group consisting of (a) the amino acid sequences shown in SEQ ID NOS:2, 56, 57, and 58 and (b) biologically active variants thereof. Symptoms of the disorder are thereby ameliorated.

Yet another embodiment of the invention is an isolated polynucleotide selected from the group consisting of: (a) a polynucleotide encoding a protein that comprises the amino acid sequence of SEQ ID NO:2, 56, 57, or 58, (b) a polynucleotide comprising the sequence of SEQ ID NO:1, (c) a polynucleotide which hybridizes under stringent conditions to a polynucleotide specified in (a) or (b); (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

Another embodiment of the invention is an expression vector comprising a polynucleotide selected from the group consisting of: (a) a polynucleotide encoding a protein that comprises the amino acid sequence of SEQ ID NO:2, 56, 57, or 58, (b) a polynucleotide comprising the sequence of SEQ ID NO:1, (c) a polynucleotide which hybridizes under stringent conditions to a polynucleotide specified in (a) or (b); (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

Even another embodiment of the invention is a host cell comprising an expression vector comprising a polynucleotide selected from the group consisting of: (a) a polynucleotide encoding a protein that comprises the amino acid sequence of SEQ ID NO:2, 56, 57, or 58, (b) a polynucleotide comprising the sequence of SEQ ID NO: 1, (c) a polynucleotide which hybridizes under stringent conditions to a polynucleotide specified in (a) or (b); (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

Another embodiment of the invention is a preparation of antibodies that specifically bind to a polypeptide selected from the group consisting of (a) the amino acid sequence shown in SEQ ID NO:2, 56, 57, or 58and (b) biologically active variants thereof.

Still another embodiment of the invention is an antisense oligonucleotide that hybridizes to a polynucleotide selected from the group consisting of (a) a polynucleotide encoding a protein that comprises the amino acid sequence of SEQ ID NO:2, 56, 57, or 58, (b) a polynucleotide comprising the sequence of SEQ ID NO:1, (c) a polynucleotide which hybridizes under stringent conditions to a polynucleotide specified in (a) or (b), (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

Thus, the invention provides a human eosinophil-1-like enzyme, which can be regulated to provide therapeutic effects.

BRIEF DESCRIPTION OF THE DRAWINGS

FIG. 1. BLASTP alignment between a human eosinophil serine protease 1-like enzyme of the invention (SEQ ID NO:2) and designated as the query sequence "Q" and a homolog sequence (AB031329, SEQ ID NO: 14) designated "H." Portions of the sequence are shown in bold to represent sequences identified by a PROSITE data base search or underlined to represent sequences identified by a BLOCKS data base search.

FIG. 2. Results of a Prosite search on the amino acid sequence of SEQ ID NO: 2.

FIG. 3. Results of a BLOCKS search on the amino acid sequence of SEQ ID NO: 2.

FIGS. 4A–4D. BLASTN alignment of the esp-1-like cDNA of the invention (SEQ ID NO: 1) designated as "Q" to a sequence designated "H" of cosmid clone 407D8 (AC005570), which has been mapped on the human chromosome 16, at position 13.3. FIG. 4A shows the alignment between nucleotides 231 and 463 of SEQ ID NO: 1 (SEQ ID NO:15). FIG. 4B shows the alignment between nucleotides 622 and 837 of SEQ ID NO: 1 (SEQ ID NO:16). FIG. 4C shows the alignment between nucleotides 64 and 230 of SEQ ID NO: 1 (SEQ ID NO:17). FIG. 4D shows the alignment between nucleotides 464 and 622 of SEQ ID NO: 1 (SEQ ID NO: 18).

FIGS. 5A–5C. Clustal w 1.74 alignment of the esp-1-like cDNA of the invention (SEQ ID NO:1) to EMBL Accession No. AB031329 (SEQ ID NO:19) and EMBL Accession No. NM006799 (SEQ ID NO:20). FIG. 5A starts the alignment at the 5'-end of the known sequence; FIG. 5B continues the alignment from FIG. 5A; and FIG. 5C continues the alignment from FIG. 5B.

FIG. 6. HMMPFAM alignment of SEQ ID NO:2 against pfam|hmm|trypsin.

FIG. 7. Expression of ESP-1-like enzyme genes as analyzed by RT-PCR.

FIG. 8. Molecular cloning of ESP-1-like and ESP-1 genes. The 5' primer is shown in SEQ ID NO:54. The 3' primer is shown in SEQ ID NO:55.

FIG. 9. Alignment of sequences of ESP-1-like enzymes (SEQ ID NOS:56, 57, and 58).

FIG. 10. ESP-1-like enzyme splicing forms which are confirmed by RT-PCR.

FIG. 11. Sequences of ESP-1-like enzyme and variants (SEQ ID NOS:56, 57, and 58).

FIG. 12. Structure of ESP-1-like enzyme genes.

FIG. 17. Expression data of ESP-1-like enzyme genes in lung primary cells.

FIG. 18. Data demonstrating the expression of ESP-1-L genes in immune cells.

FIG. 21. Mechanisms of ESP-1-like enzyme in asthma pathology.

DETAILED DESCRIPTION OF THE INVENTION

Figure 13:
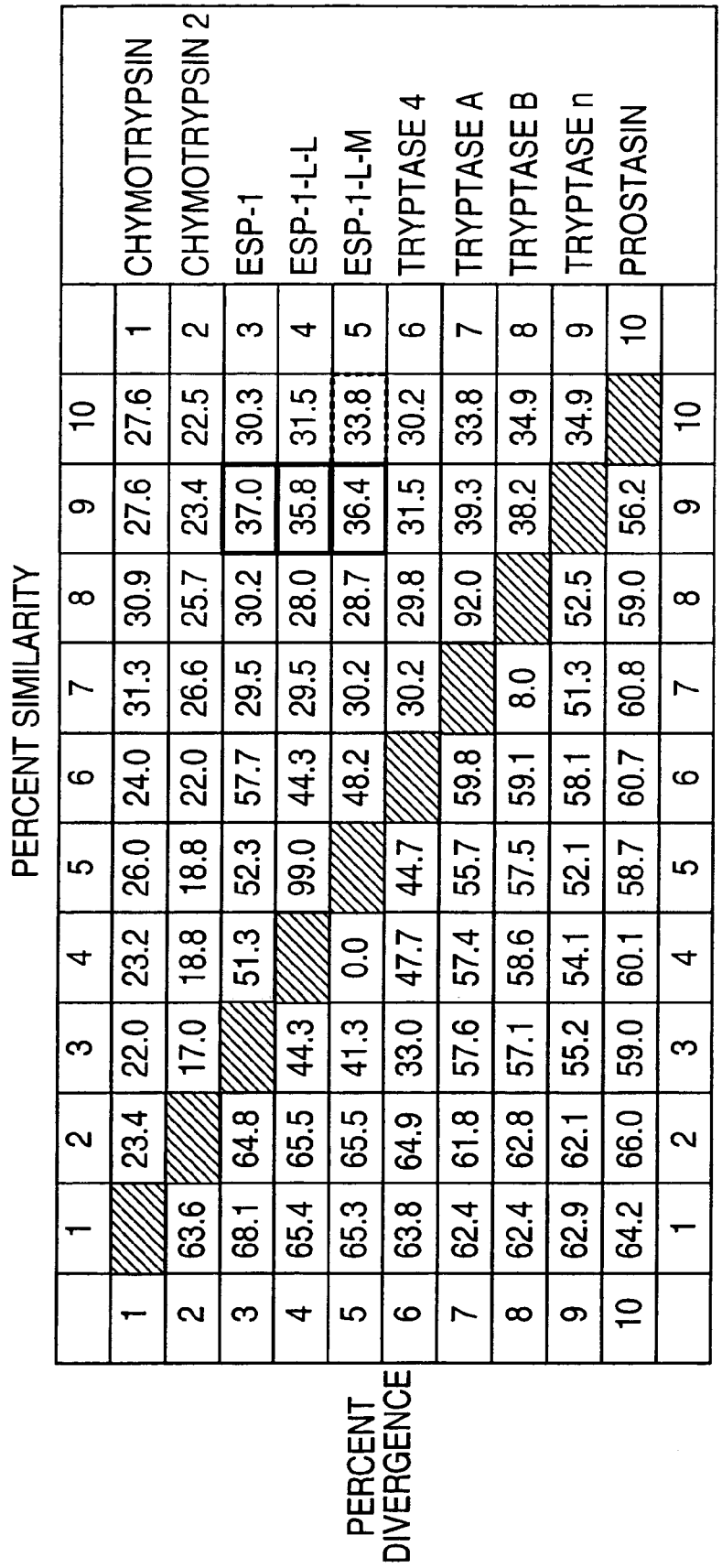
FIG. 13. Homology of ESP-1-like enzyme and other serine proteases.
Figure 14:
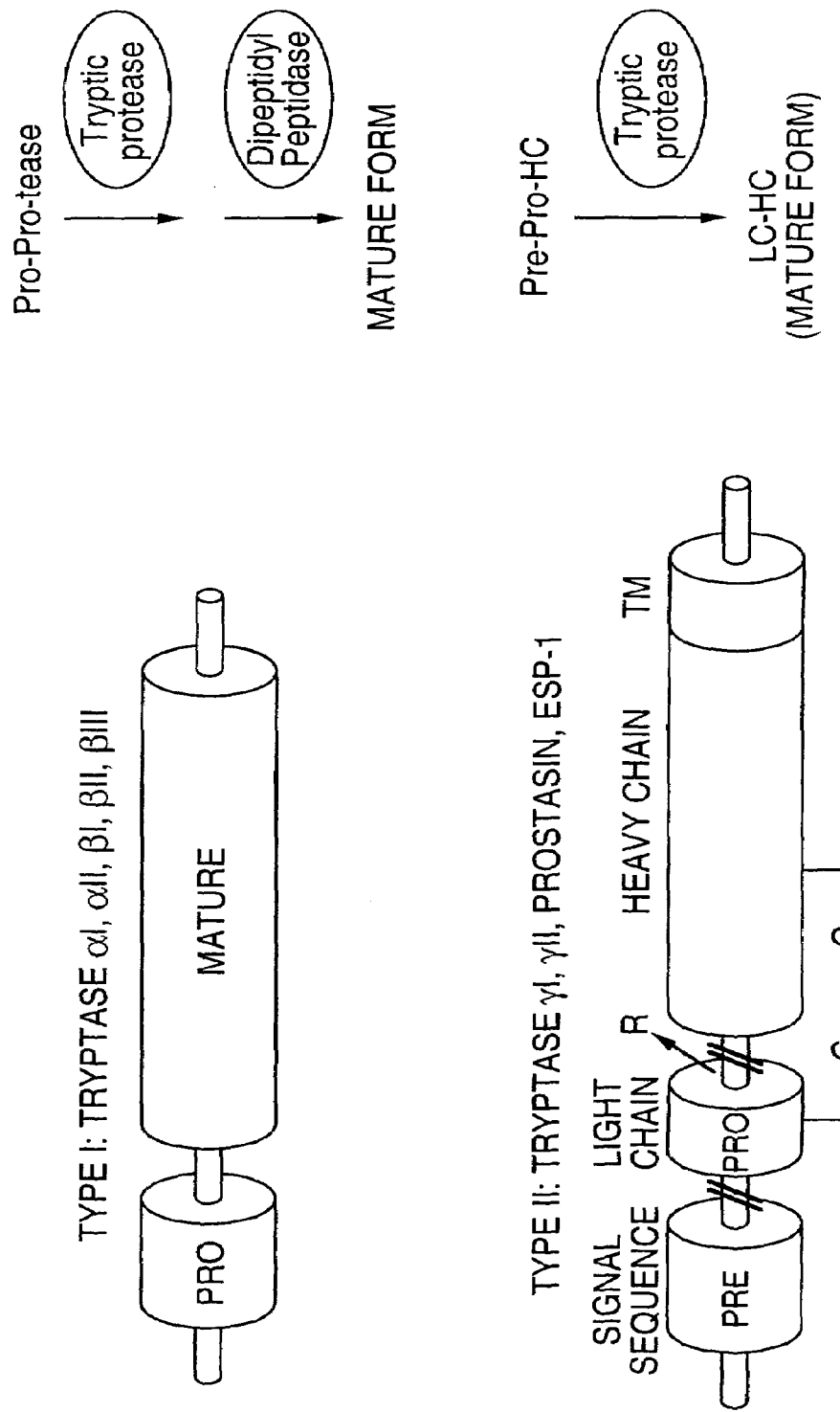
FIG. 14. Mechanisms of activation of tryptase-like serine proteases.

A novel human eosinophil serine protease-1-like enzyme (esp-1-like enzyme) is a discovery of the present invention. A human esp-1-like enzyme comprises an amino acid sequence shown in SEQ ID NO:2, 56, 57, or 58. Human eosinophil serine protease-1-like enzyme was identified by searching human genomic sequences with the AB031329 esp-1 gene product.

A nearly full-length coding sequence was identified on each of two human genomic clones with EMBL Accession Numbers AC005570 and AC005361. FIGS. 4 A-D show alignments of the coding sequence of human esp-1-like enzyme with human genomic sequences which indicates the esp-1-like enzyme gene is located on chromosome 16 at about p13.3. The human esp-1-like enzyme coding sequence is expressed, as indicated by a perfect alignment match between the 3'-end of the coding sequence and a 393 base pair EST sequence (EMBL Accession Number AW243584, SEQ ID NO:21). The BLASTP alignment shown in FIG. 1 shows a high degree of homology, 51% over 278 amino acids, between a known esp-1 (EMBL Accession No. AB031329, SEQ ID NO:14) and the esp-1-like enzyme of the invention. The AB031329 esp-1 enzyme is 100% identical in amino acid sequence to the testisin protein (EMBL Accession No. NP006790); testisin is therefore 51% identical to the esp-1-like enzyme of the invention.

The domains indicated in FIGS. 2 and 3 relate to the identification of the human esp-1-like enzyme as a serine protease of the trypsin family and to anticipated functional roles for the enzyme. For example, the fibronectin domain suggests that the esp-1-like enzyme is likely to be a cell surface protein useful in interaction with extracellular matrixes. See BLOCKS number BL01253 in FIG. 3 and also BIOCHEMISTRY, $3^{rd}$ edition, L. Stryer editor, at page 127, Freeman and Company Press (1988). Other blocks are identified as serine protease typical blocks (SEQ ID NOS: 3–13) and include the Kringle domain protein and the Apple domain protein blocks.

FIG. 5 shows the degree of identity of the eosinophil serine protease-1-like cDNA of the invention (SEQ ID NO:1) to the esp-1 cDNA (EMBL Accession No. AB031329, SEQ ID NO:17) and to the testisin cDNA (EMBL Accession No. NM006799, SEQ ID NO:18). Esp-1-like cDNA is 72.1% identical to esp-1 cDNA and also 72.1% to testisin cDNA. The esp-1 and testisin cDNA are about 90% identical.

Based on the observed features of esp-1-like enzyme, it can be expected that the enzyme will have a significant role in some of the traditional eosinophil modulated activities, including involvement in the immune response, chemotaxis, eosinophil peroxidase release, granulation, bronchial cartilage atrophy, mast cell activation, tissue sculpturing which requires protein degradation movement of cells across basement membranes, and activation of eosinophil cells and leukocytes in general. In particular, disease states such as asthma, COPD, airway allergy, and osteoporosis might be particularly addressed by therapy with esp-1 or agents that regulate the esp-1 activity. Further, the esp-1-like enzyme activity of the invention can be used in in vitro or in vivo assays to identify test compounds with potential therapeutic or diagnostic value.

Polypeptides

Eosinophil serine protease-1-like enzyme polypeptides according to the invention comprise at least 14, 15, 20, 25, 30, 35, 40, 45, 50, 75, 100, 125, 150, 175, 200, or 250 contiguous amino acids selected from the amino acid sequence shown in SEQ ID NO:2, at least 14, 15, 20, 25, 30, 35, 40, 45, 50, 75, 100, 125, 150, 175, 200, 250, or 260 contiguous amino acids selected form the amino acid sequence shown in SEQ ID NO:56, at least 14, 15, 20, 25, 30, 35, 40, 45, 50, 75, 100, 125, 150, 175, 200, 250, 275, 300, or 305 contiguous amino acids selected form the amino acid sequence shown in SEQ ID NO:57, at least 14, 15, 20, 25, 30, 35, 40, 45, 50, 75, 100, 125, 150, 175, 200, 250, 275, 300, 325, or 334 contiguous amino acids selected form the amino acid sequence shown in SEQ ID NO:56, or a biologically active variant thereof, as defined below. An esp-1-like polypeptide of the invention therefore can be a portion of an eosinophil serine protease-1-like enzyme protein, a full-length eosinophil serine protease-1-like enzyme protein, or a fusion protein comprising all or a portion of an eosinophil serine protease-1-like enzyme protein.

Biologically Active Variants

Eosinophil serine protease-1-like enzyme polypeptide variants which are biologically active, i.e., retain a serine protease activity and/or the ability to affect a biological function of an eosinophil. Eosinophils are known for a number of activities that can be monitored in vitro. For example, eosinophils can be monitored for increased levels of protein excretion, expression of peroxidase, extracellular protease activity, and the ability to transmigrate basement membranes and degrade Matrigel layers. Preferably, naturally or non-naturally occurring eosinophil serine protease-1-like enzyme polypeptide variants have amino acid sequences which are at least about 70, preferably about 75, 90, 96, or 98% identical to the amino acid sequence shown in SEQ ID NO:2, 56, 57, or 58 or a fragment thereof. Percent identity between a putative eosinophil serine protease-1-like enzyme polypeptide variant and an amino acid sequence of SEQ ID NO:2, 56, 57, or 58 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of an eosinophil serine protease-1-like enzyme polypeptide can be found using computer programs well known in the art, such as DNASTAR software. Whether an amino acid change results in a biologically active eosinophil serine protease-1-like enzyme polypeptide can readily be determined by assaying for eosinophil cell activity. Serine protease assays are discussed in U.S. Pat. Nos. 5,595,948 and 5,840,510. Esp-1-like enzyme activity can also be monitored by observation of its effects on eosinophil cellular activities. Eosinophil activities can be measured, for example, as described in Matsunaga et al., *Arch. Biochem. Biophys.*, 312:67–74 (1994), Schoonbrood et al., *Clin. Chim. Acta,* 15:163–178 (1995), Sayers et al., *J. Immunol.,* 152: 2289–2297 (1994), and Okada et al., *Am. J. Respir. Cell Mol. Biol.,* 17: 519–528 (1997). See also U.S. Pat. No. 6,051,265.

Fusion Proteins

Fusion proteins are useful for generating antibodies against eosinophil serine protease-1-like enzyme polypeptide amino acid sequences and for use in various assay systems. For example, fusion proteins can be used to identify proteins, which interact with portions of an eosinophil serine protease-1-like enzyme polypeptide. Protein affinity chromatography or library-based assays for protein-protein interactions, such as the yeast two-hybrid or phage display systems, can be used for this purpose. Such methods are well known in the art and also can be used as drug screens.

An eosinophil serine protease-1-like enzyme polypeptide fusion protein comprises two polypeptide segments fused together by means of a peptide bond. The first polypeptide segment comprises at least 14, 15, 20, 25, 30, 35, 40, 45, 50, 75, 100, 125, 150, 175, 200, or 250 contiguous amino acids selected from the amino acid sequence shown in SEQ ID NO:2, at least 14, 15, 20, 25, 30, 35, 40, 45, 50, 75, 100, 125, 150, 175, 200, 250, or 260 contiguous amino acids selected form the amino acid sequence shown in SEQ ID NO:56, at least 14, 15, 20, 25, 30, 35, 40, 45, 50, 75, 100, 125, 150, 175, 200, 250, 275, 300, or 305 contiguous amino acids selected form the amino acid sequence shown in SEQ ID NO:57, at least 14, 15, 20, 25, 30, 35, 40, 45, 50, 75, 100, 125, 150, 175, 200, 250, 275, 300, 325, or 334 contiguous amino acids selected form the amino acid sequence shown in SEQ ID NO:56 or of a biologically active variant, such as those described above. The first polypeptide segment also can comprise full-length eosinophil serine protease-1-like enzyme.

The second polypeptide segment can be a full-length protein or a protein fragment. Proteins commonly used in fusion protein construction. include beta-galactosidase, beta-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex A DNA binding domain (DBD) fusions, GAL4 DNA binding domain fusions, and herpes simplex virus (HSV) BP16 protein fusions. A fusion protein also can be engineered to contain a cleavage site located between the eosinophil serine protease-1-like enzyme polypeptide-encoding sequence, and the heterologous protein sequence so that the eosinophil serine protease-1-like enzyme polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NO: 1 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human eosinophil serine protease-1-like enzyme polypeptide can be obtained using eosinophil serine protease-1-like enzyme polynucleotides (described below) to make suitable probes or primers for screening cDNA expression libraries from other species, such as mice, monkeys, or yeast, identifying cDNAs which encode homologs of eosinophil serine protease-1-like enzyme polypeptide, and expressing the cDNAs as is known in the art.

Polynucleotides

An eosinophil serine protease-1-like enzyme-encoding polynucleotide can be single- or double-stranded and comprises a coding sequence or the complement of a coding sequence for an eosinophil serine protease-1-like enzyme polypeptide. A coding sequence for the human eosinophil serine protease-1-like enzyme shown in SEQ ID NO:2 is shown in SEQ ID NO: 1. Polynucleotides encoding the amino acid sequences shown in SEQ ID NOS:2, 56, 57, and 58 are eosinophil serine protease 1-like polynucleotides.

Degenerate nucleotide sequences encoding human eosinophil serine protease-1-like enzyme polypeptides, as well as homologous nucleotide sequences which are at least about 73, preferably about 75, 90, 96, or 98% identical to the nucleotide sequence shown in SEQ ID NO: 1 are eosinophil serine protease-1-like enzyme polynucleotides. Percent sequence identity between the sequences of two polynucleotides is determined using computer programs such as ALIGN which employ the FASTA algorithm, using an affinity gap search with a gap open penalty of −12 and a gap extension penalty of −2. Complementary DNA (cDNA) molecules, species homologs, and variants of eosinophil serine protease-1-like enzyme polynucleotides that encode biologically active eosinophil serine protease-1-like enzyme polypeptides also are eosinophil serine protease-1-like enzyme polynucleotides.

Identification of Polynucleotide Variants and Homologs

Variants and homologs of the eosinophil serine protease-1-like enzyme polynucleotides described above also are eosinophil serine protease-1-like enzyme polynucleotides. Typically, homologous eosinophil serine protease-1-like enzyme polynucleotide sequences can be identified by hybridization of candidate polynucleotides to known eosinophil serine protease-1-like enzyme polynucleotides under stringent conditions, as is known in the art. For example, using the following wash conditions—2× SSC (0.3 M NaCl, 0.03 M sodium citrate, pH 7.0), 0.1% SDS, room temperature twice, 30 minutes each; then 2× SSC, 0.1% SDS, 50° C. once, 30 minutes; then 2× SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the eosinophil serine protease-1-like enzyme polynucleotides disclosed herein also can be identified by making suitable probes or primers and screening cDNA expression libraries from other species, such as mice, monkeys, or yeast. Human variants of eosinophil serine protease-1-like enzyme polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human eosinophil serine protease-1-like enzyme polynucleotides or eosinophil serine protease-1-like enzyme polynucleotides of other species can therefore be identified by hybridizing a putative homologous eosinophil serine protease-1-like enzyme polynucleotide with a polynucleotide having a nucleotide sequence of SEQ ID NO:1 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences that hybridize to eosinophil serine protease-1-like enzyme polynucleotides or their complements following stringent hybridization and/or wash conditions also are eosinophil serine protease-1-like enzyme polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between an eosinophil serine protease-1-like enzyme polynucleotide having a nucleotide sequence shown in SEQ ID NO:1 or the complement thereof and a polynucleotide sequence which is at least about 73, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\% \ G+C) - 0.63(\% \ formamide) - 600/l),$$

where l=the length of the hybrid in basepairs.

Stringent wash conditions include, for example, 4× SSC at 65° C., or 50% formamide, 4× SSC at 42° C., or 0.5× SSC, 0.1% SDS at 65° C. Highly stringent wash conditions include, for example, 0.2× SSC at 65° C.

Preparation of Polynucleotides

A naturally occurring eosinophil serine protease-1-like enzyme polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated eosinophil serine protease-1-like enzyme polynucleotides.

For example, restriction enzymes and probes can be used to isolate polynucleotide fragments that comprise eosinophil serine protease-1-like nucleotide sequences. Isolated polynucleotides are in preparations that are free or at least 70, 80, or 90% free of other molecules.

Eosinophil serine protease-1-like enzyme cDNA molecules can be made with standard molecular biology techniques, using eosinophil serine protease-1-like mRNA as a template. Eosinophil serine protease-1-like enzyme cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesize eosinophil serine protease-1-like enzyme polynucleotides. The degeneracy; of the genetic code allows alternate nucleotide sequences to be synthesized which will encode an eosinophil serine protease-1-like enzyme polypeptide having, for example, an amino acid sequence shown in SEQ ID NO:2, 56, 57, or 58 or a biologically active variant thereof.

Extending Polynucleotides

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111–119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., *Nucleic Acids Res.* 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA that might be present in limited amounts in a particular sample.

Obtaining Polypeptides

Eosinophil serine protease-1-like enzyme polypeptides can be obtained, for example, by purification from human cells, by expression of eosinophil serine protease-1-like enzyme polynucleotides, or by direct chemical synthesis.

Protein Purification

Eosinophil serine protease-1-like enzyme polypeptides can be purified from any human cell which expresses the enzyme, including host cells that have been transfected with eosinophil serine protease-1-like enzyme expression constructs. A particular good source of esp-1-like protein is pancreatic adenocarcinoma cells. A purified eosinophil serine protease-1-like enzyme polypeptide is separated from other compounds which normally associate with the eosinophil serine protease-1-like enzyme polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. The high salt washes are likely to be enriched for esp-1-like enzyme. A preparation of purified eosinophil serine protease-1-like enzyme polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express an eosinophil serine protease-1-like enzyme polynucleotide, the polynucleotide can be inserted into an expression vector that contains the necessary elements for the transcription and translation of the inserted coding sequence. Methods which are well known to those skilled in the art can be used to construct expression vectors containing sequences encoding eosinophil serine protease-1-like enzyme polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding an eosinophil serine protease-1-like enzyme polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUE-SCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding an eosinophil serine protease-1-like enzyme polypeptide, vectors based on SV40 or EBV can be used with an appropriate selectable marker.

Bacterial and Yeast Expression Systems

In bacterial systems, a number of expression vectors can be selected depending upon the use intended for the eosinophil serine protease-1-like enzyme polypeptide. For example, when a large quantity of an eosinophil serine protease-1-like enzyme polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding the eosinophil serine protease-1-like enzyme polypeptide can be ligated into the vector in frame with sequences for the amino-terminal Met and the subsequent 7 residues of β-galactosidase so that a hybrid protein is produced. pIN vectors (Van Heeke. & Schuster, *J. Biol. Chem.* 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding eosinophil serine protease-1-like enzyme polypeptides can be driven by any of a number of promoters. For example, viral promoters such as the 35S and 19S promoters of CaMV can be used alone or in combination with the omega leader sequence from TMV (Takamatsu, *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (e.g., Hobbs or Murray, in MCGRAW HILL YEARBOOK OF SCIENCE AND TECHNOLOGY, McGraw Hill, New York, N.Y., pp. 191–196, 1992).

An insect system also can be used to express an eosinophil serine protease-1-like enzyme polypeptide. For example, in one such system *Autographa californica* nuclear polyhedrosis virus (AcNPV) is used as a vector to express foreign genes in *Spodoptera frugiperda* cells or in *Trichoplusia* larvae. Sequences encoding eosinophil serine protease-1-like enzyme polypeptides can be cloned into a non-essential region of the virus, such as the polyhedrin gene, and placed under control of the polyhedrin promoter. Successful insertion of eosinophil serine protease-1-like enzyme polypeptides will render the polyhedrin gene inactive and produce recombinant virus lacking coat protein. The recombinant viruses can then be used to infect *S. frugiperda* cells or *Trichoplusia* larvae in which eosinophil serine protease-1-like enzyme polypeptides can be expressed (Engelhard et al., *Proc. Nat. Acad. Sci.* 91, 3224–3227, 1994).

Mammalian Expression Systems

A number of viral-based expression systems can be used to express eosinophil serine protease-1-like enzyme polypeptides in mammalian host cells. For example, if an adenovirus is used as an expression vector, sequences encoding eosinophil serine protease-1-like enzyme polypeptides can be ligated into an adenovirus transcription/translation complex comprising the late promoter and tripartite leader sequence. Insertion in a non-essential E1 or E3 region of the viral genome can be used to obtain a viable virus which is capable of expressing an eosinophil serine protease-1-like enzyme polypeptide in infected host cells (Logan & Shenk, *Proc. Natl. Acad. Sci.* 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding eosinophil serine protease-1-like enzyme polypeptides. Such signals include the ATG initiation codon and adjacent sequences. In cases where sequences encoding an eosinophil serine protease-1-like enzyme polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers that are appropriate for the particular cell system which is used (see Scharf et al., *Results Probl. Cell Differ.* 20, 125–162, 1994).

Host Cells

A host cell strain can be chosen for its ability to modulate the expression of the inserted sequences or to process the expressed eosinophil serine protease-1-like enzyme polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells that have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110–2209) and can be chosen to ensure the correct modification and processing of the foreign protein.

Stable expression is preferred for long-term, high-yield production of recombinant proteins. For example, cell lines which stably express eosinophil serine protease-1-like enzyme polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells that successfully express the introduced eosinophil serine protease-1-like enzyme' sequences. Resistant clones of stably transformed cells can be proliferated using tissue culture techniques appropriate to the cell type. See, for example, ANIMAL CELL CULTURE, R. I. Freshney, ed., 1986.

Any number of selection systems can be used to recover transformed cell lines. These include, but are not limited to, the herpes simplex virus thymidine kinase (Wigler et al., *Cell* 11, 223–32, 1977) and adenine phosphoribosyltransferase (Lowy et al., *Cell* 22, 817–23, 1980) genes that can be employed in tk⁻ or aprt⁻ cells, respectively. Also, antimetabolite, antibiotic, or herbicide resistance can be used as the basis for selection. For example, dhfr confers resistance to methotrexate (Wigler et al., *Proc. Natl. Acad. Sci.* 77, 3567–70, 1980), npt confers resistance to the aminoglycosides, neomycin and G-418 (Colbere-Garapin et al., *J. Mol. Biol.* 150, 1–14, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, *Proc. Natl. Acad. Sci.* 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121–131, 1995).

Detecting Expression

Although the presence of marker gene expression suggests that the eosinophil serine protease-1-like enzyme polynucleotide is also present, its presence and expression may need to be confirmed. For example, if a sequence encoding an eosinophil serine protease-1-like enzyme polypeptide is inserted within a marker gene sequence, transformed cells containing sequences which encode an eosinophil serine protease-1-like enzyme polypeptide can be identified by the absence of marker gene function. Alternatively, a marker gene can be placed in tandem with a sequence encoding an eosinophil serine protease-1-like enzyme polypeptide under the control of a single promoter. Expression of the marker gene in response to induction or selection usually indicates expression of the eosinophil serine protease-1-like enzyme polynucleotide.

Alternatively, host cells which contain an eosinophil serine protease-1-like enzyme polynucleotide and which express an eosinophil serine protease-1-like enzyme polypeptide can be identified by a variety of procedures known to those of skill in the art. These procedures include, but are not limited to, DNA-DNA or DNA-RNA hybridizations and protein bioassay or immunoassay techniques that include membrane, solution, or chip-based technologies for the detection and/or quantification of nucleic acid or protein. For example, the presence of a polynucleotide sequence encoding an eosinophil serine protease-1-like enzyme polypeptide can be detected by DNA-DNA or DNA-RNA hybridization or amplification using probes or fragments or fragments of polynucleotides encoding an eosinophil serine protease-1-like enzyme polypeptide. Nucleic acid amplification-based assays involve the use of oligonucleotides selected from sequences encoding an eosinophil serine protease-1-like enzyme polypeptide to detect transformants that contain an eosinophil serine protease-1-like enzyme polynucleotide.

A variety of protocols for detecting and measuring the expression of an eosinophil serine protease-1-like enzyme polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on an eosinophil serine protease-1-like enzyme polypeptide can be used, or a competitive binding assay can be employed. These and other assays are described in Hampton et al., SEROLOGICAL METHODS: A LABORATORY MANUAL, APS Press, St. Paul, Minn., 1999) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding eosinophil serine protease-1-like enzyme polypeptides include oligolabeling, nick translation, end-labeling, or PCR amplification using a labeled nucleotide. Alternatively, sequences encoding an eosinophil serine protease-1-like enzyme polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding an eosinophil serine protease-1-like enzyme polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode eosinophil serine protease-1-like enzyme polypeptides can be designed to contain signal sequences which direct secretion of soluble eosinophil serine protease-1-like enzyme polypeptides through a prokaryotic or eukaryotic cell membrane or which direct the membrane insertion of membrane-bound eosinophil serine protease-1-like enzyme polypeptide.

As discussed above, other constructions can be used to join a sequence encoding an eosinophil serine protease-1-like enzyme polypeptide to a nucleotide sequence encoding a polypeptide domain that will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the eosinophil serine protease-1-like enzyme polypeptide also can be used to facilitate purification. One such expression vector provides for expression of a fusion protein containing an eosinophil serine protease-1-like enzyme polypeptide and 6 histidine residues preceding a thioredoxin or an enterokinase cleavage site. The histidine residues facilitate purification by IMAC (immobilized metal ion affinity chromatography, as described in Porath et al., *Prot. Exp. Purif.* 3, 263–281, 1992), while the enterokinase cleavage site provides a means for purifying the eosinophil serine protease-1-like enzyme polypeptide from the fusion protein. Vectors that contain fusion proteins are disclosed in Kroll et al., *DNA Cell Biol.* 12, 441–453, 1993.

Chemical Synthesis

Sequences encoding an eosinophil serine protease-1-like enzyme polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, an eosinophil serine protease-1-like enzyme polypeptide itself can be produced using chemical methods to synthesize its amino acid sequence, such as by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of eosinophil serine protease-1-like enzyme polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, W H Freeman and Co., New York, N.Y., 1983). The composition of a synthetic eosinophil serine protease-1-like enzyme polypeptide can be confirmed by amino acid analysis or sequencing (e.g., the Edman degradation procedure; see Creighton, supra). Additionally, any portion of the amino acid sequence of the eosinophil serine protease-1-like enzyme polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce eosinophil serine protease-1-like enzyme polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life that is longer than that of a transcript generated from the naturally occurring sequence.

The nucleotide sequences disclosed herein can be engineered using methods generally known in the art to alter eosinophil serine protease-1-like enzyme polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of an eosinophil serine protease-1-like enzyme polypeptide. "Antibody" as used herein includes intact immunoglobulin molecules, as well as fragments thereof, such as Fab, F(ab=)$_2$, and Fv, which are capable of binding an epitope of an eosinophil serine protease-1-like enzyme polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of an eosinophil serine protease-1-like enzyme polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody that specifically binds to the immunogen.

Typically, an antibody which specifically binds to an eosinophil serine protease-1-like enzyme polypeptide provides a detection signal at least 5-, 10-, or 20-fold higher than a detection signal provided with other proteins when used in an immunochemical assay. Preferably, antibodies which specifically bind to eosinophil serine protease-1-like enzyme polypeptides do not detect other proteins in immunochemical assays and can immunoprecipitate an eosinophil serine protease-1-like enzyme polypeptide from solution.

Eosinophil serine protease-1-like enzyme polypeptides can be used to immunize a mammal, such as a mouse, rat, rabbit, guinea pig, monkey, or human, to produce polyclonal antibodies. If desired, an eosinophil serine protease-1-like enzyme polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies that specifically bind to an eosinophil serine protease-1-like enzyme polypeptide can be prepared using any technique that provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol.* 62, 109–120, 1984).

In addition, techniques developed for the production of chimeric antibodies, the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be humanized, to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies which specifically bind to an eosinophil serine protease-1-like enzyme polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies that specifically bind to eosinophil serine protease-1-like enzyme polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to eosinophil serine protease-1-like enzyme polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which an eosinophil serine protease-1-like enzyme polypeptide is bound. The bound antibodies can then be eluted from the column using a buffer with a high salt concentration.

Antisense Oligonucleotides

Antisense oligonucleotides are nucleotide sequences that are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of eosinophil serine protease-1-like enzyme gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of eosinophil serine protease-1-like enzyme gene expression can be obtained by designing antisense oligonucleotides which will form duplexes to the control, 5', or regulatory regions of the eosinophil serine protease-1-like enzyme gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of an eosinophil serine protease-1-like enzyme polynucleotide. Antisense oligonucleotides which comprise, for example, 2, 3, 4, or 5 or more stretches of contiguous nucleotides which are precisely complementary to an eosinophil serine protease-1-like enzyme polynucleotide, each separated by a stretch of contiguous nucleotides which are not complementary to adjacent eosinophil serine protease-1-like enzyme nucleotides, can provide sufficient targeting specificity for eosinophil serine protease-1-like enzyme mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular eosinophil serine protease-1-like enzyme polynucleotide sequence.

Antisense oligonucleotides can be modified without affecting their ability to hybridize to an eosinophil serine protease-1-like enzyme polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of an eosinophil serine protease-1-like enzyme polynucleotide can be used to generate ribozymes that will specifically bind to mRNA transcribed from the eosinophil serine protease-1-like enzyme polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within an eosinophil serine protease-1-like enzyme RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate eosinophil serine protease-1-like enzyme RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease eosinophil serine protease-1-like enzyme expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors that induce expression of a target gene. Ribozymes also can be engineered to provide an additional level of regulation, so that destruction of mRNA occurs only when both a ribozyme and a target gene are induced in the cells.

Screening Methods

The invention provides assays for screening test compounds which bind to or modulate the activity of an eosinophil serine protease-1-like enzyme polypeptide or an eosinophil serine protease-1-like enzyme polynucleotide. A test compound preferably binds to an eosinophil serine protease-1-like enzyme polypeptide or polynucleotide. More preferably, a test compound decreases or increases the ability of human eosinophil serine protease-1-like enzyme to decreases or increases serine protease-1-like eosinophil or eosinophil serine protease-1-like enzyme activity by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla et al., *Proc. Natl. Acad. Sci.* 97, 6378–6382, 1990, Felici, *J. Mol. Biol.* 222, 301–310, 1991; and Ladner, U.S. Pat. No. 5,223,409).

High Throughput Screening

Test compounds can be screened for the ability to bind to eosinophil serine protease-1-like enzyme polypeptides or polynucleotides or to affect eosinophil serine protease-1-like enzyme activity or eosinophil serine protease-1-like enzyme gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, free format assays, or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614–18 (1994). The cells are placed under agarose in petri dishes, then beads that carry combinatorial compounds are placed on the surface of the agarose. The combinatorial compounds are partially released the compounds from the beads. Active compounds can be. visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57-63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule which binds to and occupies, for example, the ATP/GTP binding site of the enzyme or the active site of the eosinophil serine protease-1-like enzyme polypeptide, such that normal biological activity is prevented. Examples of such small molecules include, but are not limited to, small peptides or peptide-like molecules.

In binding assays, either the test compound or the eosinophil serine protease-1-like enzyme polypeptide can comprise a detectable label, such as a fluorescent, radioisotopic, chemiluminescent, or enzymatic label, such as horseradish peroxidase, alkaline phosphatase, or luciferase. Detection of a test compound which is bound to the eosinophil serine protease-1-like enzyme polypeptide can then be accomplished, for example, by direct counting of radioemmission, by scintillation counting, or by determining conversion of an appropriate substrate to a detectable product.

Alternatively, binding of a test compound to an eosinophil serine protease- 1-like enzyme polypeptide can be determined without labeling either of the interactants. For example, a microphysiometer can be used to detect binding of a test compound with an eosinophil serine protease-1-like enzyme polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and an eosinophil serine protease-1-like enzyme polypeptide (McConnell et al., *Science* 257, 1906–1912, 1992).

Determining the ability of a test compound to bind to an eosinophil serine protease-1-like enzyme polypeptide also can be accomplished using a technology such as real-time Bimolecular Interaction Analysis (BIA) (Sjolander & Urbaniczky, *Anal. Chem.* 63, 2338–2345, 1991, and Szabo et al., *Curr. Opin. Struct. Biol.* 5, 699–705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, an eosinophil serine protease-1-like enzyme polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with the eosinophil serine protease-1-like enzyme polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding an eosinophil serine protease-1-like enzyme polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent, complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein that interacts with the eosinophil serine protease-1-like enzyme polypeptide.

It may be desirable to immobilize either the eosinophil serine protease-1-like enzyme polypeptide (or polynucleotide) or the test compound to facilitate separation of bound from unbound forms of one or both of the interactants, as well as to accommodate automation of the assay. Thus, either the eosinophil serine protease-1-like enzyme polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the eosinophil serine protease-1-like enzyme polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to an eosinophil serine protease-1-like enzyme polypeptide (or polynucleotide) can be accomplished in any vessel suitable for containing the reactants. Examples of such vessels include microtiter plates, test tubes, and microcentrifuge tubes.

In one embodiment, the eosinophil serine protease-1-like enzyme polypeptide is a fusion protein comprising a domain that allows the eosinophil serine protease-1-like enzyme polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed eosinophil serine protease-1-like enzyme polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either an eosinophil serine protease-1-like enzyme polypeptide (or polynucleotide) or a test compound can be immobilized utilizing conjugation of biotin and streptavidin. Biotinylated eosinophil serine protease-1-like enzyme polypeptides (or polynucleotides) or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to an eosinophil serine protease-1-like enzyme polypeptide, polynucleotide, or a test compound, but which do not interfere with a desired binding site, such as the ATP/GTP binding site or the active site of the eosinophil serine protease-1-like enzyme polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the eosinophil serine protease-1-like enzyme polypeptide or test compound, enzyme-linked assays which rely on detecting an activity of the eosinophil serine protease-1-like enzyme polypeptide, and SDS gel electrophoresis under non-reducing conditions.

Screening for test compounds which bind to an eosinophil serine protease-1 like enzyme polypeptide or polynucleotide also can be carried out in an intact cell. Any cell which comprises an eosinophil serine protease-1-like enzyme polypeptide or polynucleotide can be used in a cell-based assay system. An eosinophil serine protease -1-like enzyme polynucleotide can be naturally occurring in the cell or can be introduced using techniques such as those described above. Binding of the test compound to an eosinophil serine protease-1-like enzyme polypeptide or polynucleotide is determined as described above.

Enzyme Assays

Test compounds can be tested for the ability to increase or decrease eosinophil or eosinophil serine protease-1-like activity. Serine protease assays can be carried out as described in U.S. Pat. Nos. 5,695,948 and 5,840,510. The enzymatic activity can also be observed indirectly, by measuring eosinophil activity by methods described in Matsunaga et al., *Arch. Biochem. Biophys.*, 312:67–74 (1994) (serine protease activity typically is purified from eosinophils of patients with asthma in the high salt fraction of a protein; also release of peroxidase from eosinophils of patients with asthma), Schoonbrood et al., *Clin. Chim. Acta*, 15:163–178 (1995)(increased secretion of proteins in eosinophils from patients with COPD), Sayers et al., *J. Immunol.*, 152:2289–2297 (1994), and Okada et al., *Am. J. Respir. Cell Mol. Biol.*, 17: 519–528 (1997) (migration of eosinophils through basement membranes). See also U.S. Pat. No. 6,051,265.

Enzyme assays can be carried out after contacting either a purified eosinophil serine protease-1-like enzyme polypeptide, a cell membrane preparation, or an intact cell with a test compound. A test compound which decreases an eosinophil activity of an eosinophil serine protease-1-like enzyme polypeptide by at least about 10, preferably about 50, more preferably about 75, 90, or 100% is identified as a potential therapeutic agent for decreasing eosinophil serine protease-1-like enzyme activity. A test compound that increases an eosinophil activity of a human eosinophil serine protease-1-like enzyme polypeptide by at least about 10, preferably about 50, more preferably about 75, 90, or 100% is identified as a potential therapeutic agent for increasing human eosinophil serine protease-1-like enzyme activity.

Gene Expression

In another embodiment, test compounds that increase or decrease eosinophil serine protease-1-like enzyme gene expression are identified. An eosinophil serine protease-1-like enzyme polynucleotide is contacted with a test compound, and the expression of an RNA or polypeptide product of the eosinophil serine protease-1-like enzyme polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of eosinophil serine protease-1-like enzyme mRNA or polypeptide expression in the cells can be determined by methods well known in the art for detecting mRNA or polypeptide. Either qualitative or quantitative methods can be used. The presence of polypeptide products of an eosinophil serine protease-1-like enzyme polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into an eosinophil serine protease-1-like enzyme polypeptide.

Such screening can be carried out either in a cell-free assay system or in an intact cell. Any cell that expresses an eosinophil serine protease-1-like enzyme polynucleotide can be used in a cell-based assay system. The eosinophil serine protease-1-like enzyme polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also provides pharmaceutical compositions that can be administered to a patient to achieve a therapeutic effect. Pharmaceutical compositions of the invention can comprise, for example, an eosinophil serine protease-1-like enzyme polypeptide, eosinophil serine protease-1-like enzyme polynucleotide, ribozymes or antisense oligonucleotides, antibodies which specifically bind to an eosinophil serine protease-1-like enzyme polypeptide, or mimetics, agonists, antagonists, or inhibitors of an eosinophil serine protease-1-like enzyme polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated conditions Such labeling would include amount, frequency, and method of administration.

Therapeutic Indications and Methods

Eosinophil cellular activity is higher in respiratory conditions characterized by inflammation. Matsunaga supra, Bettiol et al., *Allergy,* 54:1188–1193 (1999), Ennis et al., *Clin. Exp. Allergy* 29:362–366 (1999). Thus, inhibition of human eosinophil serine protease-1-like enzyme is expected to be useful for treating inflammatory conditions of the immune system, such as COPD. Regulation of the esp-1-like enzyme also can be used to treat asthma, airway allergy, and osteoporosis.

COPD.

Chronic obstructive pulmonary (or airways) disease (COPD) is a condition defined physiologically as airflow obstruction that generally results from a mixture of emphysema and peripheral airway obstruction due to chronic bronchitis (Senior & Shapiro, *Pulmonary Diseases and Disorders,* 3d ed., New York, McGraw-Hill, 1998, pp. 659–681, 1998; Barnes, *Chest* 117, 10S–14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and $CD8^+$ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

COPD is characterized by damage to the lung extracellular matrix and emphysema can be viewed as the pathologic process that affects the lung parenchyma. This process eventually leads to the destruction of the airway walls resulting in permanent airspace enlargement (Senior and Shapiro, in PULMONARY DISEASES AND DISORDERS, 3rd ed., New York, McGraw-Hill, 1998, pp. 659–681, 1998). The observation that inherited deficiency of a1-antitrypsin (a1-AT), the primary inhibitor of neutrophil elastase, predisposes individuals to early onset emphysema, and that intrapulmonary instillation of elastolytic enzymes in experimental animals causes emphysema, led to the elastase:antielastase hypothesis for the pathogenesis of emphysema (Eriksson, *Acta Med. Scand.* 177(*Suppl.*), 432, 1965, Gross, *J. Occup. Med.* 6, 481–84, 1964). This in turn led to the concept that destruction of elastin in the lung parenchyma is the basis of the development of emphysema.

A broad range of immune and inflammatory cells including neutrophils, macrophages, T lymphocytes and eosinophils contain proteolytic enzymes that could contribute to the destruction of lung extracellular matrix (Shapiro, 1999). In addition, a number of different classes of proteases have been identified that have the potential to contribute to lung matrix destruction. These include serine proteases, matrix metalloproteinases and cysteine proteases. Of these classes of enzymes, a number can hydrolyze elastin and have been shown to be elevated in COPD patients (neutrophil elastase, MMP-2, 9, 12) (Culpitt et al., *Am. J. Respir. Crit. Care Med.* 160, 1635–39, 1999, Shapiro, *Am. J. Crit. Care Med.* 160 (5), S29–S32,1999).

It is expected that in the future novel members of the existing classes of proteases and new classes of proteases will be identified that play a significant role in the damage of the extracellular lung matrix including elastin proteolysis. Novel protease targets therefore remain very attractive therapeutic targets.

Allergies and Asthma.

Allergy is a complex process in which environmental antigens induce clinically adverse reactions. The inducing antigens, called allergens, typically elicit a specific IgE response and, although in most cases the allergens themselves have little or no intrinsic toxicity, they induce pathology when the IgE response in turn elicits an IgE-dependent or T cell-dependent hypersensitivity reaction. Hypersensitivity reactions can be local or systemic and typically occur within minutes of allergen exposure in individuals who have previously been sensitized to an allergen. The hypersensitivity reaction of allergy develops when the allergen is recognized by IgE antibodies bound to specific receptors on the surface of effector cells, such as mast cells, basophils, or eosinophils, which causes the activation of the effector cells and the release of mediators that produce the acute signs and symptoms of the reactions. Allergic diseases include asthma, allergic rhinitis (hay fever), atopic dermatitis, and anaphylaxis.

Asthma is though to arise as a result of interactions between multiple genetic and environmental factors and is characterized by three major features: 1) intermittent and reversible airway obstruction caused by bronchoconstriction, increased mucus production, and thickening of the walls of the airways that leads to a narrowing of the airways, 2) airway hyperresponsiveness caused by a decreased control of airway caliber, and 3) airway inflammation. Certain cells are critical to the inflammatory reaction of asthma and they include T cells and antigen presenting cells, B cells that produce IgE, and mast cells, basophils, eosinophils, and other cells that bind IgE. These effector cells accumulate at the site of allergic reaction in the airways and release toxic products that contribute to the acute pathology and eventually to the tissue destruction related to the disorder. Other resident cells, such as smooth muscle cells, lung epithelial cells, mucus-producing cells, and nerve cells may also be abnormal in individuals with asthma and may contribute to the pathology. While the airway obstruction of asthma, presenting clinically as an intermittent wheeze and shortness of breath, is generally the most pressing symptom of the disease requiring immediate treatment, the inflammation and tissue destruction associated with the disease can lead to irreversible changes that eventually make asthma a chronic disabling disorder requiring long-term management.

Despite recent important advances in our understanding of the pathophysiology of asthma, the disease appears to be increasing in prevalence and severity (Gergen and Weiss, *Am. Rev. Respir. Dis.* 146, 823–24, 1992). It is estimated that 30–40% of the population suffer with atopic allergy, and 15% of children and 5% of adults in the population suffer from asthma (Gergen and Weiss, 1992). Thus, an enormous burden is placed on our health care resources. However, both diagnosis and treatment of asthma are difficult. The severity of lung tissue inflammation is not easy to measure and the symptoms of the disease are often indistinguishable from those of respiratory infections, chronic respiratory inflammatory disorders, allergic rhinitis, or other respiratory disorders. Often, the inciting allergen cannot be determined, making removal of the causative environmental agent difficult. Current pharmacological treatments suffer their own set of disadvantages. Commonly used therapeutic agents, such as beta agonists, can act as symptom relievers to transiently improve pulmonary function, but do not affect the underlying inflammation. Agents that can reduce the underlying inflammation, such as anti-inflammatory steroids, can have major drawbacks that range from immunosuppression to bone loss (Goodman and Gilman's THE PHARMACOLOGIC BASIS OF THERAPEUTICS, Seventh Edition, MacMillan Publishing Company, NY, USA, 1985). In addition, many of the present therapies, such as inhaled corticosteroids, are short-lasting, inconvenient to use, and must be used often on a regular basis, in some cases for life, making failure of patients to comply with the treatment a major problem and thereby reducing their effectiveness as a treatment.

Because of the problems associated with conventional therapies, alternative treatment strategies have been evaluated. Glycophorin A (Chu and Sharom, *Cell. Immunol.* 145, 223–39, 1992), cyclosporin (Alexander et al., *Lancet* 339, 324–28, 1992), and a nonapeptide fragment of IL-2 (Zav'yalov et al., *Immunol. Lett.* 31, 285–88, 1992) all inhibit interleukin-2 dependent T lymphocyte proliferation; however, they are known to have many other effects. For example, cyclosporin is used as a immunosuppressant after organ transplantation. While these agents may represent alternatives to steroids in the treatment of asthmatics, they inhibit interleukin-2 dependent T lymphocyte proliferation and potentially critical immune functions associated with homeostasis. Other treatments that block the release or activity of mediators of bronchochonstriction, such as cromones or anti-leukotrienes, have recently been introduced for the treatment of mild asthma, but they are expensive and not effective in all patients and it is unclear whether they have any effect on the chronic changes associated with asthmatic inflammation. What is needed in the art is the identification of a treatment that can act in pathways critical to the development of asthma_that both blocks the episodic attacks of the disorder and preferentially dampens the hyperactive allergic immune response without immunocompromising the patient.

Osteoporosis. Osteoporosis is a disease characterized by low bone mass and microarchitectural deterioration of bone tissue, leading to enhanced bone fragility and a consequent increase in fracture risk. It is the most common human metabolic bone disorder. Established osteoporosis includes the presence of fractures. Bone turnover occurs by the action of two major effector cell types within bone: the osteoclast, which is responsible for bone resorption, and the osteoblast, which synthesizes and mineralizes bone matrix. The actions of osteoclasts and osteoblasts are highly coordinated. Osteoclast precursors are recruited to the site of turnover; they differentiate and fuse to form mature osteoclasts, which then resorb bone. Attached to the bone surface, osteoclasts produce an acidic microenvironment in a tightly defined junction between the specialized osteoclast border membrane and the bone matrix, thus allowing the localized solubilization of bone matrix. This, in turn, facilitates the proteolysis of demineralized bone collagen. Matrix degradation is thought to release matrix-associated growth factor and cytokines, which recruit osteoblasts in a temporally and spatially controlled fashion. Osteoblasts synthesize and secrete new bone matrix proteins, and subsequently mineralize this new matrix. In the normal skeleton this is a physiological process which does not result in a net change in bone mass. In pathological states, such as osteoporosis, the balance between resorption and formation is altered such that bone loss occurs. See WO 99/45923.

The osteoclast itself is the direct or indirect target of all currently available osteoporosis agents with the possible exception of fluoride. Antiresorptive therapy prevents further bone loss in treated individuals. Osteoblasts are derived from multipotent stem cells that reside in bone marrow and also gives rise to adipocytes, chondrocytes, fibroblasts and muscle cells. Selective enhancement of osteoblast activity is a highly desirable goal for osteoporosis therapy since it would result in an increase in bone mass, rather than a prevention of further bone loss. An effective anabolic therapy would be expected to lead to a significantly greater reduction in fracture risk than currently available treatments.

The agonists or antagonists to the newly discovered polypeptides may act as antiresorptive by directly altering the osteoclast differentiation, osteoclast adhesion to the bone matrix or osteoclast function of degrading the bone matrix. The agonists or antagonists could indirectly alter the osteoclast function by interfering in the synthesis and/or modification of effector molecules of osteoclast differentiation or function such as cytokines, peptide or steroid hormones, proteases, etc.

The agonists or antagonists to the newly discovered polypeptides may act as anabolics by directly enhancing the osteoblast differentiation and /or its bone matrix forming function. The agonists or antagonists could also indirectly alter the osteoblast function by enhancing the synthesis of growth factors, peptide or steroid hormones or decreasing the synthesis of inhibitory molecules.

The agonists and antagonists may be used to mimic, augment or inhibit the action of the newly discovered polypeptides that may be useful to treat osteoporosis, Paget's disease, degradation of bone implants particularly dental implants.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or an eosinophil serine protease-1-like enzyme polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent that affects eosinophil serine protease-1-like enzyme activity can be administered to a human cell, either in vitro or in vivo, to reduce eosinophil serine protease-1-like enzyme activity. The reagent preferably binds to an expression product of a human eosinophil serine protease-1-like enzyme gene. If the expression product is a protein, the reagent is preferably an antibody. For treatment of human cells ex vivo, an antibody can be added to a preparation of stem cells that have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 μg of DNA per 16 nmole of liposome delivered to about $10^6$ cells, more preferably about 1.0 μg of DNA per 16 nmole of liposome delivered to about $10^6$ cells, and even more preferably about 2.0 μg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated. to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 μg to about 10 μg of polynucleotide is combined with about 8 nmol of liposomes, more preferably from about 0.5 μg to about 5 μg of polynucleotides are combined with about 8 nmol liposomes, and even more preferably about 1.0 μg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

Determination of a Therapeutically Effective Dose

The determination of a therapeutically effective dose is well within the capability of those skilled in the art. A therapeutically effective dose refers to that amount of active ingredient that increases or decreases eosinophil serine protease- 1-like enzyme activity relative to the eosinophil serine protease-1-like enzyme activity that occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, gene gun, and DEAE- or calcium phosphate-mediated transfection.

Effective in vivo dosages of an antibody are in the range of about 5 µg to about 50 µg /kg, about 50 µg to about 5 mg/kg, about 100 µg to about 500 µg /kg of patient body weight, and about 200 to about 250 µg /kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides that express antisense oligonucleotides or ribozymes can be introduced into cells by a variety of methods, as described above.

Preferably, a reagent reduces expression of an eosinophil serine protease-1-like enzyme gene or the activity of an eosinophil serine protease-1-like enzyme polypeptide by at least about 10, preferably about 50, more preferably about 75, 90, or 100% relative to the absence of the reagent. The effectiveness of the mechanism chosen to decrease the level of expression of an eosinophil serine protease-1-like enzyme gene or the activity of an eosinophil serine protease-1-like enzyme polypeptide can be assessed using methods well known in the art, such as hybridization of nucleotide probes to eosinophil serine protease-1-like enzyme-specific mRNA, quantitative RT-PCR, immunologic detection of an eosinophil serine protease-1-like enzyme polypeptide, or measurement of eosinophil serine protease-1-like enzyme activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human eosinophil serine protease-1-like enzyme also can be used in diagnostic assays for detecting diseases and abnormalities or susceptibility to diseases and abnormalities related to the presence of mutations in the nucleic acid sequences which encode the enzyme. For example, differences can be determined between the cDNA or genomic sequence encoding eosinophil serine protease-1-like enzyme in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., Science 230, 1242, 1985). Sequence changes at specific locations can also be revealed by nuclease protection assays, such as RNase and S 1 protection or the chemical cleavage method (e.g., Cotton et al., Proc. Natl. Acad. Sci. USA 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of an eosinophil serine protease-1-like enzyme also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents and patent applications cited in this disclosure are expressly incorporated herein by reference. The above disclosure generally describes the present invention. A more complete understanding can be obtained by reference to. the following specific examples which are provided for purposes of illustration only and are not intended to limit the scope of the invention.

EXAMPLE 1

Detection of Esp-1-like Enzyme Activity

The polynucleotide of SEQ ID NO: 1 is inserted into pGEX vector and expressed as a fusion protein with glutathione S-transferase. The fusion. protein is purified from lysed cells by adsorption by glutathion-agarose-beads followed by elution in the presence of free glutathione. The activity of the fusion protein (esp-1-like enzyme polypeptide of SEQ ID NO: 2) is assessed by the hydrolysis of various peptide thiobenzyl ester substrates. The substrates are chosen to represent the different SP types (chymase, trypase, aspase, etc.). Assays are performed at room temperature (~25° C.) and contain an aliquot of the fusion protein and the appropriate substrate in HEPES buffer, pH 7.5, containing 0.01M CaCl2 and 8% dimethylsulfoxide. The reaction also contains 0.34 mM dithiopyridine, which reacts with the thiobenzyl group that is released during hydrolysis and converts it to thiopyridone. The reaction is carried out in an optical cuvette, and the generation of thiopyridone is measured in a spectrophotometer by the absorption produced at 324 nm. The amount of thiopyridone produced in the reaction is proportional to the activity of the fusion protein. It is shown that the polypeptide of SEQ ID NO: 2 has esp-1-like enzyme activity.

EXAMPLE 2

Expression of Recombinant Human Eosinophil Serine Protease-1-like Enzyme

To produce large quantities of human eosinophil serine protease-1-like enzyme polypeptides in yeast, the *Pichia pastoris* expression vector pPICZB (Invitrogen, San Diego, Calif.) is used. The human eosinophil serine protease-1-like enzyme encoding DNA sequence is the nucleotide sequence shown in SEQ ID NO: 1. Before insertion into vector pPICZB, the DNA sequence is modified by well known methods in such a way that it contains at its 5'-end an initiation codon and at its 3'-end an enterokinase cleavage site, a His6 reporter tag, and a termination codon. Restriction enzyme recognition sequences for cleavage by restriction endonucleases are added at both termini. After digestion of the multiple cloning site of pPICZ B with the. corresponding restriction enzymes, the modified human eosinophil serine protease-1-like enzyme polypeptide-encoding DNA sequence is ligated into pPICZB. This expression vector is designed for inducible expression in *Pichia pastoris*, and expression is driven by a yeast promoter. The resulting pPICZ/md-His6 vector is used to transform the yeast.

The yeast is cultivated under usual conditions in shake flasks, and the recombinantly produced protein is isolated from the culture by affinity chromatography (Ni-NTA-Resin) in the presence of 8 M urea. The bound polypeptide is eluted with buffer, pH 3.5, and neutralized. Separation of the human eosinophil serine protease-1-like enzyme polypeptide from the His6 reporter tag is accomplished by site-specific proteolysis using enterokinase (Invitrogen, San Diego, Calif.) according to manufacturer's instructions. Purified human eosinophil serine protease-l-like enzyme polypeptide is obtained.

EXAMPLE 3

Identification of Test Compounds that Bind to Eosinophil Serine Protease-1-like Enzyme Polypeptides Purified eosinophil serine protease-1-like enzyme polypeptides comprising a glutathione-S-transferase protein and absorbed onto glutathione-derivatized wells of 96-well microtiter plates are contacted with test compounds from a small molecule library at pH 7.0 in a physiological buffer solution. Eosinophil serine protease-1-like enzyme polypeptides comprise the amino acid sequence shown in SEQ ID NO:2, 56, 57, or 58. The test compounds comprise a fluorescent tag. The samples are incubated for 5 minutes to one hour. Control samples are incubated in the absence of a test compound. The buffer solution containing the test compounds is washed from the wells. Binding of a test compound to an eosinophil serine protease-1-like enzyme polypeptide is detected by fluorescence measurements of the contents of the wells. A test compound that increases the fluorescence in a well by at least 15% relative to fluorescence of a well in which a test compound is not incubated is identified as a compound which binds to an eosinophil serine protease-1-like enzyme polypeptide.

EXAMPLE 4

Identification of a Test Compound which Decreases Eosinophil Serine Protease-1-like Enzyme Gene Expression A test compound is administered to a culture of human cells transfected with an eosinophil serine protease-1-like enzyme expression construct and incubated at 37° C. for 10 to 45 minutes. A culture of the same type of cells that have not been transfected is incubated for the same time without the test compound to provide a negative control. RNA is isolated from the two cultures as described in Chirgwin et al., *Biochem.* 18, 5294–99 (1979). Northern blots are prepared using 20 to 30 µg total RNA and hybridized with a $^{32}$P-labeled eosinophil serine protease-1-like enzyme-specific probe at 65° C. in Express-hyb (CLONTECH). The probe comprises at least 11 contiguous nucleotides selected from the complement of SEQ ID NO: 1. A test compound that decreases the eosinophil serine protease-1-like enzyme-specific signal relative to the signal obtained in the absence of the test compound is identified as an inhibitor of eosinophil serine protease-1-like enzyme gene expression.

EXAMPLE 5

Identification of a Test Compound that Regulates Human Esp-1-like Activity

A human cell not initially expressing esp-1-like protein is transfected by standard methods with the coding region of the esp-1-like enzyme (SEQ ID NO: 1) engineered for expression in the cell. The successful transfection and expression of esp-1-like are monitored by methods described above.

The ability to migrate through basement membrane components is measured in vitro by the methods of Okada, supra. Briefly, a Matrigel-coated chemotaxis chamber and the eosinophil is added to the upper chamber. Matrigel degradation and migration of the eosinophil are monitored in the presence and absence of the test compound and compared to controls.

Classes of compounds that alter Matrigel degradation are known. For example, platelet activating factor and interleukin 5, together promote Matrigel degradation activity. These compounds and classes of compounds and random small molecule libraries can each be tested to observe the effect of the compound on activities related to expression of the esp-1-like enzyme.

Other assays can be set up to monitor eosinophil serine protease activity, secretion of proteins, or peroxidase release. Glucocorticosteroids are known to affect local secretion of proteins; chemostatin can inhibit protease activity and peroxidase release. Further, protease activity can be assayed directly, by methods known in the art. See also U.S. Pat. Nos. 5,695,948 and 5,840,510 and references therein.

EXAMPLE 6

Treatment of a Patient Suffering from COPD with a Reagent Which Specifically Binds to an Esp-1-like Human Gene mRNA Synthesis of an antisense eosinophil oligonucleotide comprising at least 11 contiguous nucleotides selected from the complement of SEQ ID NO:1 is performed on a Pharmacia Gene Assembler series synthesizer using the phosphoramidite procedure (Uhlmann et al., *Chem. Rev.* 90, 534–83, 1990). Following assembly and deprotection, the oligonucleotide is twice ethanol-precipitated, dried, and suspended in phosphate-buffered saline (PBS) at the desired concentration. Purity of the oligonucleotide is tested by capillary gel electrophoreses and ion exchange HPLC. The endotoxin level in the oligonucleotide preparation is determined using the Limulus Amebocyte Assay (Bang, *Biol. Bull.* (*Woods Hole, Mass.*) 105, 361–362, 1953). An aqueous composition containing the antisense oligonucleotides at a concentration of 0.1–100 µM is administered directly to a patient having chronic obstructive pulmonary disease (COPD) by injection. The severity of the patient's COPD is decreased.

EXAMPLE 7

Tissue-specific Expression of Eosinophil Serine Protease 1-Like Enzyme

The qualitative expression pattern of eosinophil serine protease 1-like enzyme in various tissues is determined by Reverse Transcription-Polymerase Chain Reaction (RT-PCR).

To demonstrate that eosinophil serine protease 1-like enzyme is involved in the disease process of COPD, the initial expression panel consists of RNA samples from respiratory tissues and inflammatory cells relevant to COPD: lung (adult and fetal), trachea, freshly isolated alveolar type II cells, cultured human bronchial epithelial cells, cultured small airway epithelial cells, cultured bronchial sooth muscle cells, cultured H441 cells (Clara-like), freshly isolated neutrophils and monocytes, and cultured monocytes (macrophage-like). Body map profiling also is carried out, using total RNA panels purchased from Clontech. The tissues are adrenal gland, bone marrow, brain, colon, heart, kidney, liver, lung, mammary gland, pancreas, prostate, salivary gland, skeletal muscle, small intestine, spleen, stomach, testis, thymus, trachea, thyroid, and uterus.

Quantitative Expression Profiling. Quantitative expression profiling is performed by the form of quantitative PCR analysis called "kinetic analysis" firstly described in Higuchi et al., *BioTechnology* 10, 413–17, 1992, and Higuchi et al., *BioTechnology* 11, 1026–30, 1993. The principle is that at any given cycle within the exponential phase of PCR, the amount of product is proportional to the initial number of template copies.

If the amplification is performed in the presence of an internally quenched fluorescent oligonucleotide (TaqMan probe) complementary to the target sequence, the probe is cleaved by the 5'–3' endonuclease activity of Taq DNA polymerase and a fluorescent dye released in the medium (Holland et al., *Proc. Natl. Acad. Sci. U.S.A.* 88, 7276–80, 1991). Because the fluorescence emission will increase in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6, 995–1001, 1996).

The amplification of an endogenous control can be performed to standardize the amount of sample RNA added to a reaction. In this kind of experiment, the control of choice is the 18S ribosomal RNA. Because reporter dyes with differing emission spectra are available, the target and the endogenous control can be independently quantified in the same tube if probes labeled with different dyes are used.

All "real time PCR" measurements of fluorescence are made in the ABI Prism 7700.

RNA Extraction and cDNA Preparation. Total RNA from the tissues listed above are used for expression quantification. RNAs labeled "from autopsy" were extracted from autoptic tissues with the TRIzol reagent (Life Technologies, MD) according to the manufacturer's protocol.

Fifty µg of each RNA were treated with DNase I for 1 hour at 37°C. in the following reaction mix: 0.2 U/µl RNase-free DNase I (Roche Diagnostics, Germany); 0.4 U/µl RNase inhibitor (PE Applied Biosystems, Calif.); 10 mM Tris-HCl pH 7.9; 10 mM $MgCl_2$; 50 mM NaCl; and 1 mM DTT.

After incubation, RNA is extracted once with 1 volume of phenol:chloroform:isoamyl alcohol (24:24:1) and once with chloroform, and precipitated with 1/10 volume of 3 M NaAcetate, pH5.2, and 2 volumes of ethanol.

Fifty µg of each RNA from the autoptic tissues are DNase treated with the DNA-free kit purchased from Ambion (Ambion, Tex.). After resuspension and spectrophotometric quantification, each sample is reverse transcribed with the TaqMan Reverse Transcription Reagents (PE Applied Biosystems, Calif.) according to the manufacturer's protocol. The final concentration of RNA in the reaction mix is 200 ng/µL. Reverse transcription is carried out with 2.5 µM of random hexamer primers.

TaqMan Quantitative Analysis. Specific primers and probe are designed according to the recommendations of PE Applied Biosystems; the probe can be labeled at the 5' end FAM (6-carboxy-fluorescein) and at the 3' end with TAMRA (6-carboxy-tetramethyl-rhodamine). Quantification experiments are performed on 10 ng of reverse transcribed RNA from each sample. Each determination is done in triplicate.

Total cDNA content is normalized with the simultaneous quantification (multiplex PCR) of the 18S ribosomal RNA using the Pre-Developed TaqMan Assay Reagents (PDAR) Control Kit (PE Applied Biosystems, Calif.).

The assay reaction mix is as follows: 1× final TaqMan Universal PCR Master Mix (from 2× stock) (PE Applied Biosystems, Calif.); 1× PDAR control—18S RNA (from 20× stock); 300 nM forward primer; 900 nM reverse primer; 200 nM probe; 10 ng cDNA; and water to 25 µl.

Each of the following steps are carried out once: pre PCR, 2 minutes at 50° C., and 10 minutes at 95° C. The following steps are carried out 40 times: denaturation, 15 seconds at 95° C., annealing/extension, 1 minute at 60° C.

The experiment is performed on an ABI Prism 7700 Sequence Detector (PE Applied Biosystems, Calif.). At the end of the run, fluorescence data acquired during PCR are processed as described in the ABI Prism 7700 user's manual in order to achieve better background subtraction as well as signal linearity with the starting target quantity.

EXAMPLE 8

Identification of Test Compound Efficacy in a COPD Animal Model

Guinea pigs are exposed on a single occasion to tobacco smoke for 50 minutes. Animals are sacrificed between 10 minutes and 24 hour following the end of the exposure and their lungs placed in RNAlater™. The lung tissue is homogenized, and total RNA was extracted using a Qiagens RNeasy™ Maxi kit. Molecular Probes RiboGreen™ RNA quantitation method is used to quantify the amount of RNA in each sample.

Total RNA is reverse transcribed, and the resultant cDNA is used in a real-time polymerase chain reaction (PCR). The cDNA is added to a solution containing the sense and anti-sense primers and the 6-carboxy-tetramethyl-rhodamine labeled probe of the eosinophil serine protease 1-like enzyme gene. Cyclophilin is used as the housekeeping gene. The expression of the eosinophil serine protease 1-like enzyme gene is measured using the TaqMan real-time PCR system that generates an amplification curve for each sample. From this curve a threshold cycle value is calculated: the fractional cycle number at which the amount of amplified target reaches a fixed threshold. A sample containing many copies of the eosinophil serine protease 1-like enzyme gene will reach this threshold earlier than a sample containing fewer copies. The threshold is set at 0.2, and the threshold cycle $C_T$ is calculated from the amplification curve. The $C_T$ value for the eosinophil serine protease 1-like enzyme gene is normalized using the $C_T$ value for the housekeeping gene.

Expression of the eosinophil serine protease 1-like enzyme gene is increased by at least 3-fold between 10 minutes and 3 hours post tobacco smoke exposure compared to air exposed control animals.

Test compounds are evaluated as follows. Animals are pre-treated with a test compound between 5 minutes and 1 hour prior to the tobacco smoke exposure and they are then sacrificed up to 3 hours after the tobacco smoke exposure has been completed. Control animals are pre-treated with the vehicle of the test compound via the route of administration chosen for the test compound. A test compound that reduces the tobacco smoke induced upregulation of eosinophil serine protease 1-like enzyme gene relative to the expression seen in vehicle treated tobacco smoke exposed animals is identified as an inhibitor of eosinophil serine protease 1-like enzyme gene expression.

EXAMPLE 9

Eosinophil Serine Protease 1-like Enzyme and its Function in Inflammation Pathology Materials and Methods Cells. Primary NHBE (normal human bronchial epithelial cells), BSMC (bronchial smooth muscle cells), SAEC (small airway endothelial cells) and NHLF (normal human lung fibroblast cells) were purchased from Clonetics. Cells were cultured according to the instruction from the manufacture. For activation, IL-4 (10 ng/ml)/anti-CD40 antibody (0.5 µg/ml, and TNF-α (25 ng/ml) were used. CD4+ T cells were purified from PBMC by negative selection with cocktail antibodies of CD8, CD14, CD16, CD19, CD56 and glycophorin A. CD4+ cells were activated by incubation with CD3 and CD28 antibodies for 20 hours. Pollen cider and mite dust polarization of CD4+ T cells was obtained by culturing CD4+ T cells and feeder cells with anti-IL-12 antibodies, anti-INF-γ antibodies, and IL-4 with pollen or mite dust antigens for 3 weeks. Eosinophils (purity >99%) were isolated with Mono-Poly resolving medium (Dainippon Pharmaceutical Co. Ltd.) followed with lysis of erythrocytes and negative selection with CD16, CD4, CD8, CD19 using autoMACS. Dendritic cells were prepared from PBMC. Briefly, PBMCs were isolated with Ficoll-paque (Pharmacia) and then cultured in RPMI1640 with 10% FBS.

After 2 hours incubation, adhered monocytes were isolated by removing the non-adhesion cells from dishes. Thereafter, monocytes were cultured in a medium containing GM-CSF (25 ng/ml) and IL-4 (10 ng/ml) and immature dendritic cells were harvest after one week. Mature dendritic cells were obtained by adding TNF-α (10 ng/ml) and culturing for one more week. Purity was checked by FACS analysis. CD4+ cells are >95% pure, eosinophils has >99% purity, and DC has >97% purity. BL2 B cells, Jurkat T cells and A549 lung epithelial cells were culture with standard methods. BL2 cells were stimulated with IL-4 (10 ng/ml) and anti-CD40 antibody (0.5 µg/ml). Jurkat T cells were activated with ionomycin ((25 nM) and PMA (2.5 nM). A549 cells were stimulated with TNF-α (25ng/ml).

RNA isolation and RT-PCR. Total RNAs were prepared using TRJzol™ Reagent (GJBCO BRL) or purchased from Clontech. First-strand cDNA synthesis was carried out with SuperScript™ first-strand synthesis system (GIBCO BRL). PCR reactions were performed with either GeneAmp PCR system 9700 or LightCycler (Roche). The following primers are used:

```
ESP-3b R:
5'-ATTGCGTAAAACCCCAAGTGCGTC-3'    (SEQ ID NO:22)

ESP-3c L:
5'-TGAGCTCGGGGCGCTACAGGC-3'       (SEQ ID NO:23)

ESP-3d L:
5'-AAGCCGGAGTCGCAGGAGGAGGAG-3'    (SEQ ID NO:24)

ESP-3e L:
5'-GCGGGGCGCTGGCCATGGCA-3'        (SEQ ID NO:25)

IL-4L:
5'-CCCAACTGCTTCCCCCTCTGTTCT-3'    (SEQ ID NO:26)

IL-4R:
5'-GGCAGCGAGTGTCCTTCTCATGGT-3'    (SEQ ID NO:27)

IL-6L:
5'-CCACCGGGAACGAAAGAGAAGCTC-3'    (SEQ ID NO:28)

IL-6R:
5'-GGCTGAGATGCCGTCGAGGATGTA-3'    (SEQ ID NO:29)

IL-8L:
5'-AAATTGAGGCCAAGGGCCAAGAGA-3'    (SEQ ID NO:30)

IL-8R:
5'-GGAGAAACCAAGGCACAGTGGAACA-3'   (SEQ ID NO:31)

IL-9L:
5'-GATCCAGCTTCCAAGTGCCACTGC-3'    (SEQ ID NO:32)

IL-9R:
5'-GTGGTTTGGTTGCATGGCTGTTCA-3'    (SEQ ID NO:33)

IL-10L:
5'-GAAACCAGGGAGCCCCTTTGATGA-3'    (SEQ ID NO:34)

IL-10R:
5'-ACGGGGTTTCACCATGTTGACCAG-3'    (SEQ ID NO:35)

RANTES-L:
5'-CCATATTCCTCGGACACCACAC-3'      (SEQ ID NO:36)

RANTES-R:
5'-AACTCCTGACCTCAAGTGATCCAC-3'    (SEQ ID NO:37)

GM-CSF-L:
5'-ACACAGCCCTGGGAGCATGTGAAT-3'    (SEQ ID NO:38)

GM-CSF-R:
5'-CACAGGAAGTTTCCGGGGTTGGAG-3'    (SEQ ID NO:39)

TNFRP75-L:
5'-GTTTGTTTCTCCCCCTGGGCTCTG-3'    (SEQ ID NO:40)
```

```
-continued
TNFRP75-R:
5'-CACCTGGCCTGAGGTGATGCTTTC-3'     (SEQ ID NO:41)

IL-9R-L:
5'-AGCAGCAGCAGCAGCAACAACAAC-3'    (SEQ ID NO:42)

IL-9R-R:
5'-CCTTGCTGAGGACAGAAGGGAGCA-3'    (SEQ ID NO:43)

IL-13R-L:
5'-GATTGAGGCTGGGAGACAGCCGTA-3'    (SEQ ID NO:44)

IL-13R-R:
5'-CACTTCCCCACTCCCAGACTGCAT-3'    (SEQ ID NO:45)

CCR3-L:
5'-TTGGAAATGACTGTGAGCGGAGCA-3'    (SEQ ID NO:46)

CCR3-R:
5'-AGAGTTCCGGCTCTGCTGTGGATG-3'    (SEQ ID NO:47)

CCR4-L:
5'-TGATCTTTGCCGTGGTGGTCCTCT-3'    (SEQ ID NO:48)

CCR4-R:
5'-ACAAAAAGGCCCCTGCAGGTTTTG-3'    (SEQ ID NO:49)

CD40-L:
5'-CCCCATCATCTTCGGGATCCTGTT-3'    (SEQ ID NO:50)

CD40-R:
5'-GGTGGGTGCAGCCTCACTGTCTCT-3'    (SEQ ID NO:51)

CD45-L:
5'-TTGGGAGTCCAGGAGAGCCTCAGA-3'    (SEQ ID NO:52)

CD45-R:
5'-TGCAGCACTTCCATTACGTTGCAC-3'    (SEQ ID NO:53)
```

Results are shown in FIGS. 10 and 17–19.

Cloning of Eosinophil Serine Protease 1-Like Enzyme ORF. PCR amplification of eosinophil serine protease 1-like enzyme ORF was performed with Advantage™-GC 2 (Clontech) and primers with sequences of 5'-ATGGGCGCGCGCGGGGCGCTG (SEQ ID NO:54) and 3'-GGGAGCCCACAGCAGGGCAAGG (SEQ ID NO:55).

Figure 15:
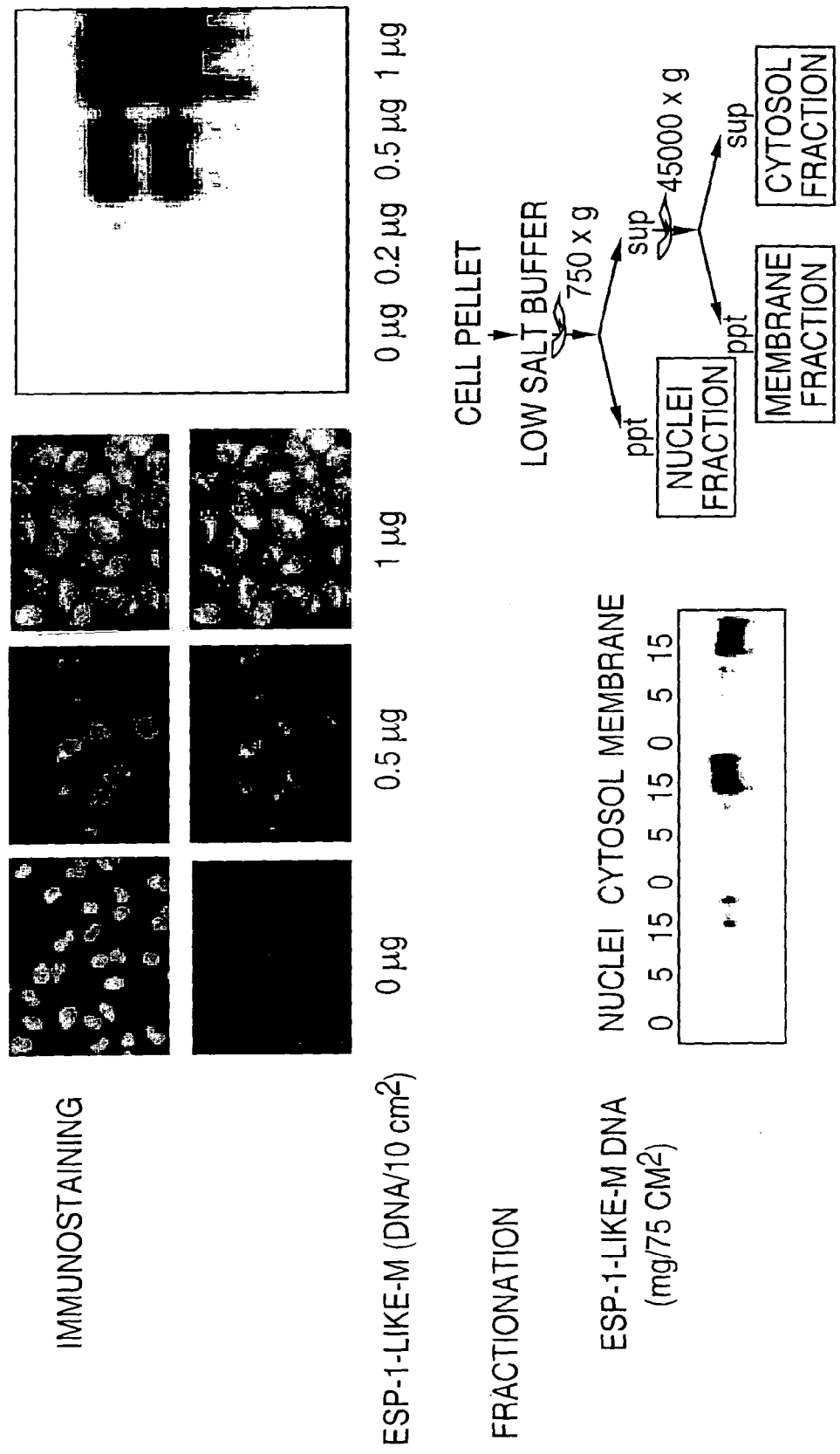
FIG. 15. Data demonstrating that ESP-1-like-M is expressed as a membrane protein.
Figure 16A:
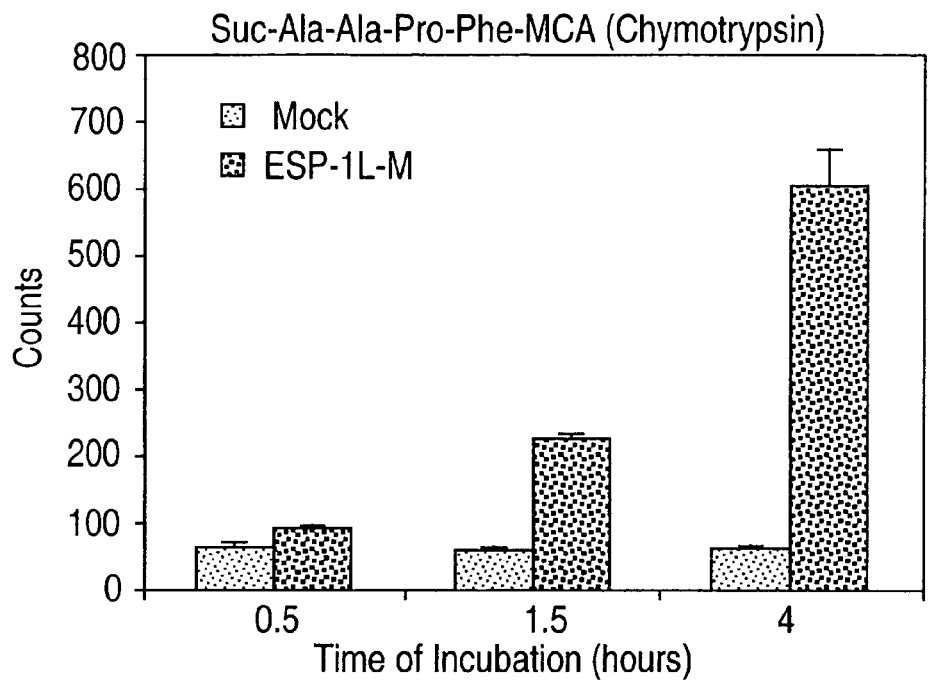
FIG. 16. Data demonstrating protease activity in the membrane fraction of ESP-1-L-M expressing cells.
Figure 16B:
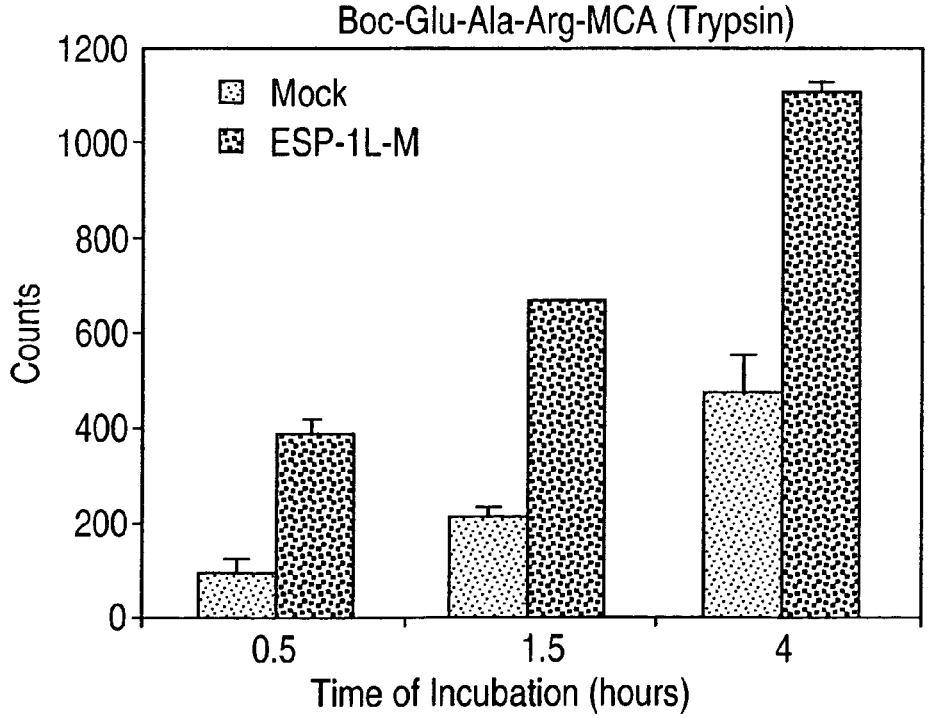
Figure 16C:
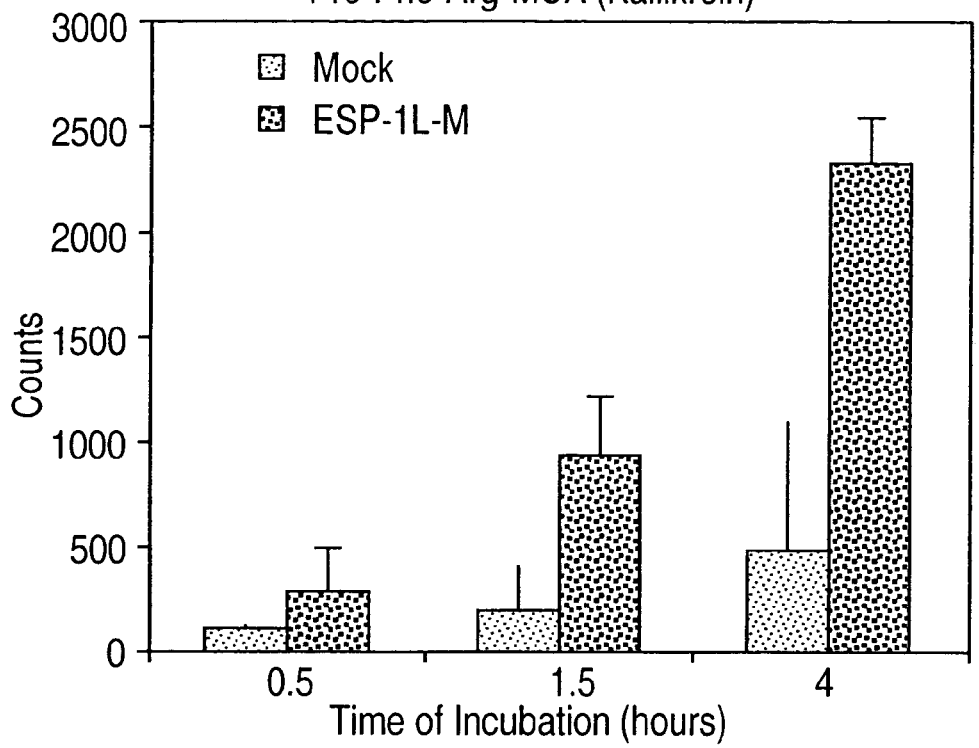
Figure 16D:
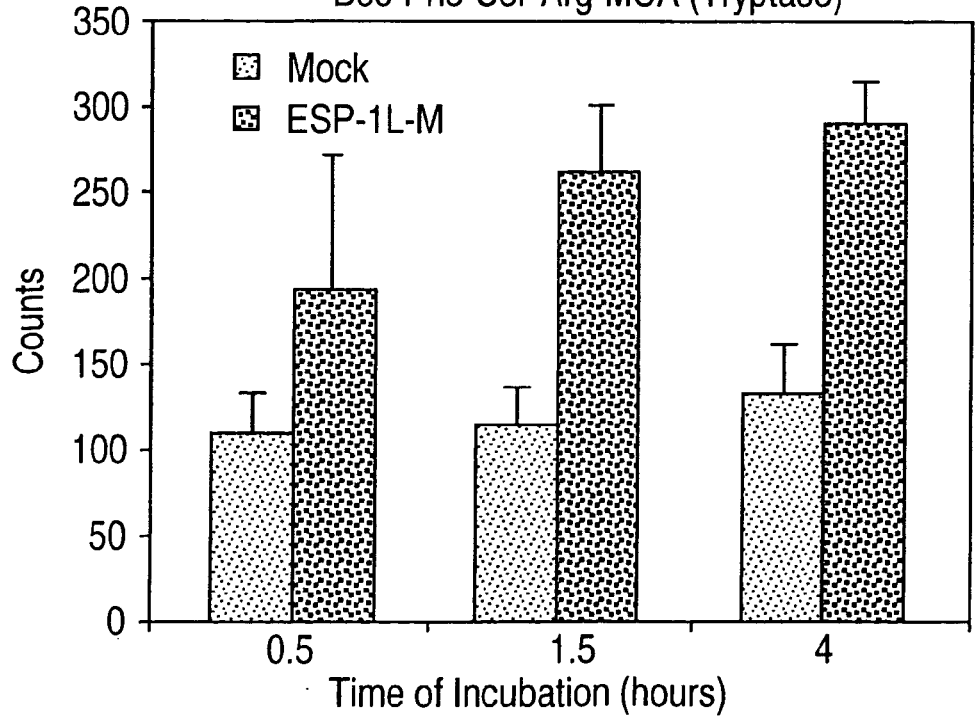

Expression of eosinophil serine protease 1-like enzyme in A549 cells and investigation of eosinophil serine protease 1-like enzyme-induced phenotype (FIG. 15).

Expression of eosinophil serine protease 1-like enzyme in A549 cells and investigation of eosinophil serine protease 1-like enzyme-induced phenotype (FIG. 15).

A549 cells were transfected with Lipofectamine Plus™ Reagent (GIBCO BRL) as described in the instruction. Forty hours after transfection, total RNA isolation, or cell lysate preparation, or immunostaining were carried out. RNA isolation and cDNA synthesis were described as above. Quantitative analysis of eosinophil serine protease 1-like enzyme-induced genes was performed with the gene primers of cytokines, chemokines, receptors, et al., listed above using LightCycler system. The comparison of the gene expression between the cells transfected with eosinophil serine protease 1-like enzyme or mock vectors was normalized with house keeping gene GAPDH.

For membrane fraction preparation, cell pellets were suspended in cold hypotonic buffer (50 mM Tris-HCl pH 7.5), and homogenized with Polytron (Cat.#PT10-35, Kinematica AG, Switzerland). Thereafter, cells were centrifuged at 500×g for 5 minutes at 4° C. to remove the nuclear fraction, and supernatants were centrifuged at 45,000×g, 4° C. for 15 minutes to precipitate membrane fraction. Then the sup ematant was removed, precipitated membrane fraction was suspended in a buffer containing 50 mM Tris-HCl pH 7.5, 10% Glycerol, and 0.5% bovine serum albumin (Cat#A-3059, Sigma). Membrane fraction was either used freshly or stored at −80° C. until use. Results are shown in FIG. 16.

Protease activities were assayed with peptidyl fluorogenic substrates at room temperature. Buffers with different pH, such as, pH6.0 PIPES buffer (12.5 mM PIPES, 110 mM NaCl and 5 mM KCl), pH7.0 PIPES buffer (12.5 mM PIPES, 110 mM NaCl and 5 mM KCl), and pH8.0 HEPES buffer (10 mM HEPES, 110 mM NaCl and 5 mM KCl) were used. The enzyme activity was determined by measuring the change of the concentration of the released products at $\lambda_{ex}$380 nm and $\lambda_{em}$460 nm on a multi-label counter (Amersham Pharmacia Biotech).

Immunofluorescence staining of eosinophil serine protease 1-like enzyme transfected cells. Cells were cultured on cover glasses overnight and reach 50% confluence. Different amount of expression vectors (eosinophil serine protease 1-like enzyme and Mock) were transfected into cells as described above. Forty hours after transfection, the medium was removed and cells were washed twice with PBS. Then, cells were fixed with cold acetone for 2 min and followed with 3 times washing with TBS. Thereafter, blocking solution (PBS with 10% FBS) was added and incubated for 20 min. For staining, cells were incubated with FITC-anti-V5 antibodies for 1 hour at room in the dark. Finally, cells were washed with PBS and observed with a fluorescence microscope equipped with a FITC filter.

Western blotting was carried out with anti-V5 antibody using standard methods.

Expression Profiling of Eosinophil Serine Protease 1-Like Enzyme. Quantitative RT-PCR analysis of RNA from different human tissues was performed to investigate the tissue distribution of ESP-1-like enzyme mRNA. In most cases, 25 μg of total RNA from various tissues (including Human Total RNA Panel I-V, Clontech Laboratories, Palo Alto, Calif., U.S.A.) was used as a template to synthesize first-strand cDNA using the SUPERSCRIPT™ First-Strand Synthesis System for RT-PCR (Life Technologies, Rockville, Md., U.S.A.). First-strand cDNA synthesis was carried out according to the manufacturer's protocol using oligo (dT) to hybridize to the 3' poly A tails of mRNA and prime the synthesis reaction. 10 ng of the first-strand cDNA was then used as template in a polymerase chain reaction. In other cases, 10 ng of commercially available cDNAs (Human Immune System MTC Panel and Human Blood Fractions MTC Panel, Clontech Laboratories, Palo Alto, Calif., U.S.A.) were used as template in a polymerase chain reaction. The polymerase chain reaction was performed in a LightCycler (Roche Molecular Biochemicals, Indianapolis, Ind., U.S.A.), in the presence of the DNA-binding fluorescent dye SYBR Green I which binds to the minor groove of the DNA double helix, produced only when double-stranded DNA is successfully synthesized in the reaction (Morrison et al., 1998). Upon binding to double-stranded DNA, SYBR Green I emits light that can be quantitatively measured by the LightCycler machine. The polymerase chain reaction was carried out using oligonucleotide primers The results are given in FIG. 19.

Discussion. Expression profiling of human eosinophil serine protease 1-like enzyme gene in 26 human tissues suggests that it is specifically expressed in trachea and testis (FIG. 7).

PCR amplification of eosinophil serine protease 1-like enzyme gene from human trachea cDNA library results in 3 PCR products (FIG. 8). Cloning and sequence analysis of the three PCR products indicate that eosinophil serine protease 1-like enzyme gene has three splicing variants with the sequences slightly different from previously predicted by GeneScan (FIG. 9). The existence of the splicing variants was confirmed by using primers covering the sequences of splicing junction (FIG. 10). eosinophil serine protease 1-like enzyme and its variants, namely ESP-1-L-L, ESP-1-L-M, and ESP-1-L-S, encode polypeptides containing 334, 305 and 259 amino acids respectively (FIG. 11). All these splicing form contain the triad catalytic domains (FIG. 12). However the hydrophobic region of the N-terminal signal sequence in ESP-1-L-S is partially deleted, indicating that ESP-1-L-S has a cytoplasmic localization (FIG. 12).

Eosinophil seine protease 1-like enzyme genes have >50% identity with ESP-1, a serine protease identified from eosinophils (FIG. 13). High homologies were observed in N-terminal signal sequence, three serine protease catalytic domains and a hydrophobic tails, suggesting that eosinophil serine protease 1-like enzyme gene may expressed as membrane seine protease. Based on database searches and computer-assisted multiple sequence alignments and phylogenetic comparisons, in addition to the similarity with ESP-1, eosinophil serine protease 1-like enzyme amino acid sequences are most similar to the well-characterized tryptases, such as mouse tryptase 4, human tryptase γ, α, β and protasin (FIG. 13). Eosinophil serine protease 1-like enzyme has the particularly tryptic-like serine protease structure features, e.g., the "catalytic triad" residues His (94 for ESP-1-L-L), Asp (163 for ESP-1-L-L) and Ser (265 for ESP-1-L-L). Features shared with tryptase γ, prostasin and ESP-1 include $Cy^{62}$ and $Cys^{183}$ those may form a disulfide linkage between propeptide and catalytic domain. However, the ending Arg of a propeptide is not existed in eosinophil serine protease 1-like enzyme. In addition, LPPPY motif for oligomerization identified in tryptase β is conserved in eosinophil serine protease 1-like enzyme. Therefore both mechanisms (FIG. 9) involved in activation of tryptase-like serine proteases are possibly employed by eosinophil serine protease 1-like enzyme.

Eosinophil serine protease 1-like enzyme is expressed as a membrane protease and expression of eosinophil serine protease 1-like enzyme induces protease activity in membrane fraction. Recombinant eosinophil serine protease 1-like enzyme-V5-His (with the tag at C-terminal) was expressed in A549 cells. Immunostaining of A549 cells (FIG. 15) and immunoblotting of fractionated cell lysates (FIG. 15) with anti-V5 antibodies indicate that eosinophil serine protease 1-like enzyme is expressed as a membrane protein. When the membrane fractions from eosinophil serine protease 1-like enzyme expressing A549 cells were subjected to protease assay with a panel of peptide substrates, cleavages were observe with the following peptides: Suc-Ala-Ala-Pro-Phe-MCA (chymotrypsin), Pro-Phe-Arg-MCA (Kallikrein), Boc-Glu-Ala-Arg-MCA (Trypsin) and Boc-Phe-Ser-Arg-MCA (Tryptase) (FIG. 16). These substrates were not active with the membrane fractions prepared from A549 cells transfected with mock vectors. Therefore, the protease activities in the membrane fraction of eosinophil serine protease 1-like enzyme expressing A549 cells were contributed either directly. by eosinophil seine protease 1-like enzyme itself or by eosinophil serine protease 1-like enzyme-activated proteases. If the later hypothesis is true, the function of eosinophil serine protease 1-like enzyme in inflammatory pathology may be amplifies by its activation of other crucial proteases, such as chymase, kallikrein, MMPs and so on.

Eosinophil serine protease 1-like enzyme can be secreted from cells when the hydrophobic tail was deleted. An expression construct with 15 amino acid deletion at C-terminal (predicted transmembrane domain), namely pESP-1-L-delC-V5-His, was expressed in A549 cells. Forty hours after transfection, culture medium was collected and followed with immunoprecipitation using anti-V5 antibodies. As shown in FIG. 12, ESP-1-L-delC could be detected in culture medium, indicating that eosinophil serine protease 1-like enzyme is expressed as extracellular membrane protein and the deletion of the C-terminal transmembrane domain leads to the secretion of eosinophil serine protease 1-like enzyme. This result also suggested that it is possible that eosinophil serine protease 1-like enzyme is secreted from cells after proteolysis in the inflamed tissue and may function as inflammatory mediators involving in airway damage and remodeling.

Asthma pathological features are characterized as over inflated lung, plasma exudation, epithelial damage, infiltration of leukocytes into the airway wall, greater thickness of the epithelium, smooth muscle, and airway wall. Since eosinophil serine protease 1-like enzyme showed specific expression in trachea, to elucidate whether eosinophil serine protease 1-like enzyme plays roles in the development of airway inflammation, detailed expression analysis of eosinophil serine protease 1-like enzyme in primary airway cells was conducted. As depicted in FIG. 18, ESP-1-L-M was induced in bronchial endothelial cells, bronchial epithelial cells and smooth muscle cells in response to IL-4/CD40 and/or TNF-α stimulation.

Activation of bronchial endothelial cells is an early event of airway inflammation including, expression of adhesion molecule and stimulation of leukocyte migration to the inflamed tissue. Great increased expression of eosinophil serine protease 1-like enzyme in bronchial endothelial cells by IL-4, CD40 and TNF-α stimulation strongly suggests the possibility that eosinophil serine protease 1-like enzyme serine protease may play pivotal roles in inflammation-induced endothelium leakage, plasma exudation, mucus production, tissue swelling, and infiltration of leukocytes.

The induced expression was also observed in bronchial epithelial cells, indicating that eosinophil serine protease 1-like enzyme may involve in damaging and shedding of epithelium. Functional damage to epithelium impairs its ability to protect the airway from the external environment, prevent the epithelium from modulating airway caliber, mucus transport, and fluid balance in the airway, and stimulate production of factors that upregulate the initial inflammation and allow such inflammation to become more established and more chronic.

Figure 19B:
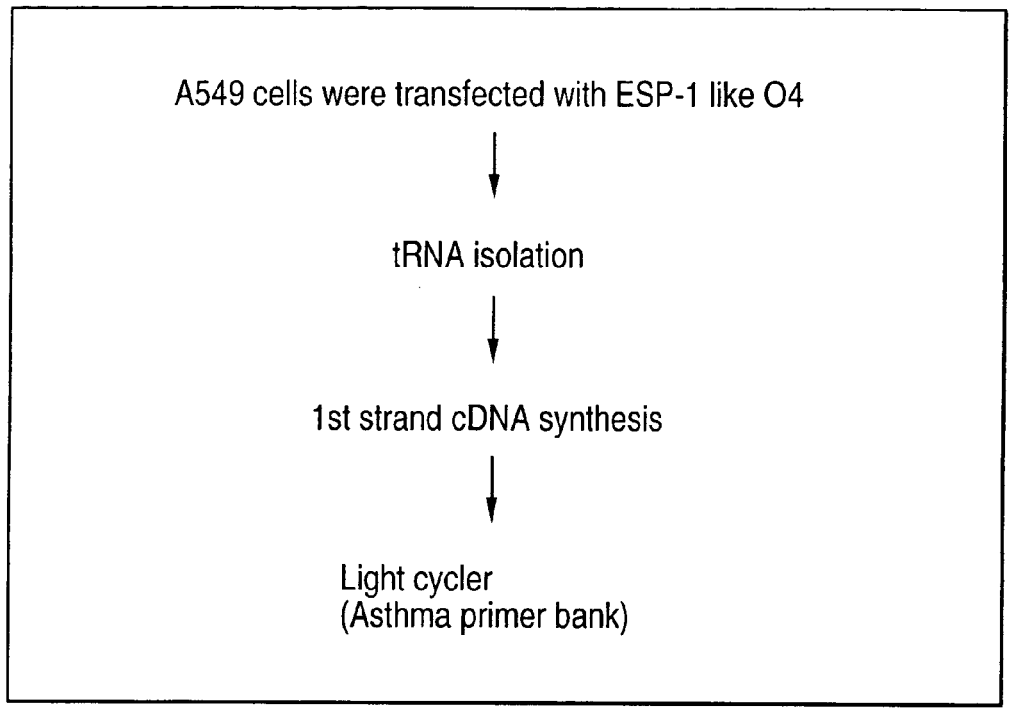
FIG. 19. Analysis of ESP-1 like dependent gene expression.
Figure 19C:
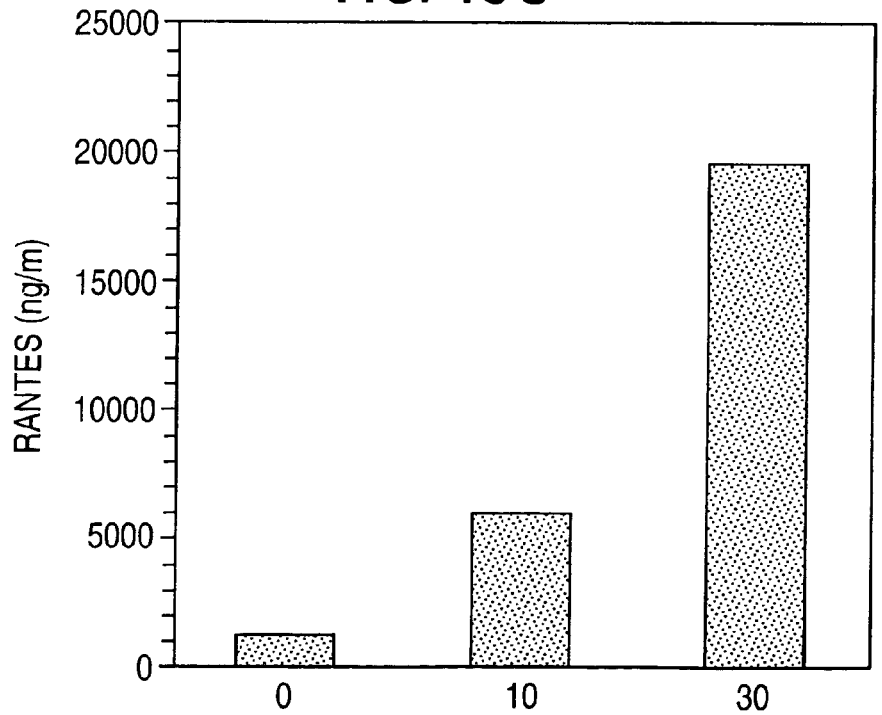

Although the level of eosinophil serine protease 1-like enzyme expression in spleen and thymus was much lower than that in trachea, expression analysis of eosinophil serine protease 1-like enzyme in immune cells showed the significant high expression of eosinophil serine protease 1-like enzyme in eosinophils and monocytes (FIG. 19).

Eosinophils manufacture several toxic mediators capable of producing many of the pathological features of asthma and are present in large numbers in the airways of asthmatic patients. Eosinophils produce an array of cytokines and inflammatory mediators, such as IL-1, 3,5,6,8, TNF-α, GM-CSF, major basic protein, leukotriene C4, platelet-activating factors, eosinophil cationic protein, eosinophil-derived neurotoxin, eosinophil peroxidase and so on. When inflammation is triggered by antigen-induced activation of mast cells, T cells, macrophage, dendritic cells and endothelial cells, circulating eosinophils are captured by the activated endothelium and migrate into the inflamed tissue. A plausible biological mechanism of eosinophil serine protease 1-like enzyme membrane serine protease is to promote the recruitment process through degradation of endothelial basement membrane by its protease activity or via activation of other proteases. Infiltrated eosinophils become activated and release their mediators and cytokines at the site of inflammation, and result in creating the abnormality associated with asthma, such as chronic inflammation.

Another interesting finding is that although the expression of eosinophil serine protease 1-like enzyme could not be detected in resting T cells, B cells and immature DC cells, the induced transcription was observed in activated CD4+T cells, IL-4 and CD40-stimulated BL2 B cell line and mature DCs (FIG. 19). This expression pattern suggested that eosinophil serine protease 1-like enzyme might selectively promote a subset of leukocytes, activated and functioning T cells, B cells and dendritic cells, to migrate into inflamed tissue. The expression specificity and its membrane localization may confer the protease activity of eosinophil serine protease 1-like enzyme being limited in inflammatory cells and inflammatory area. This unique property gives eosinophil serine protease 1-like enzyme a high impact as a drug target for the treatment of inflammatory disease, such as asthma.

Figure 20:
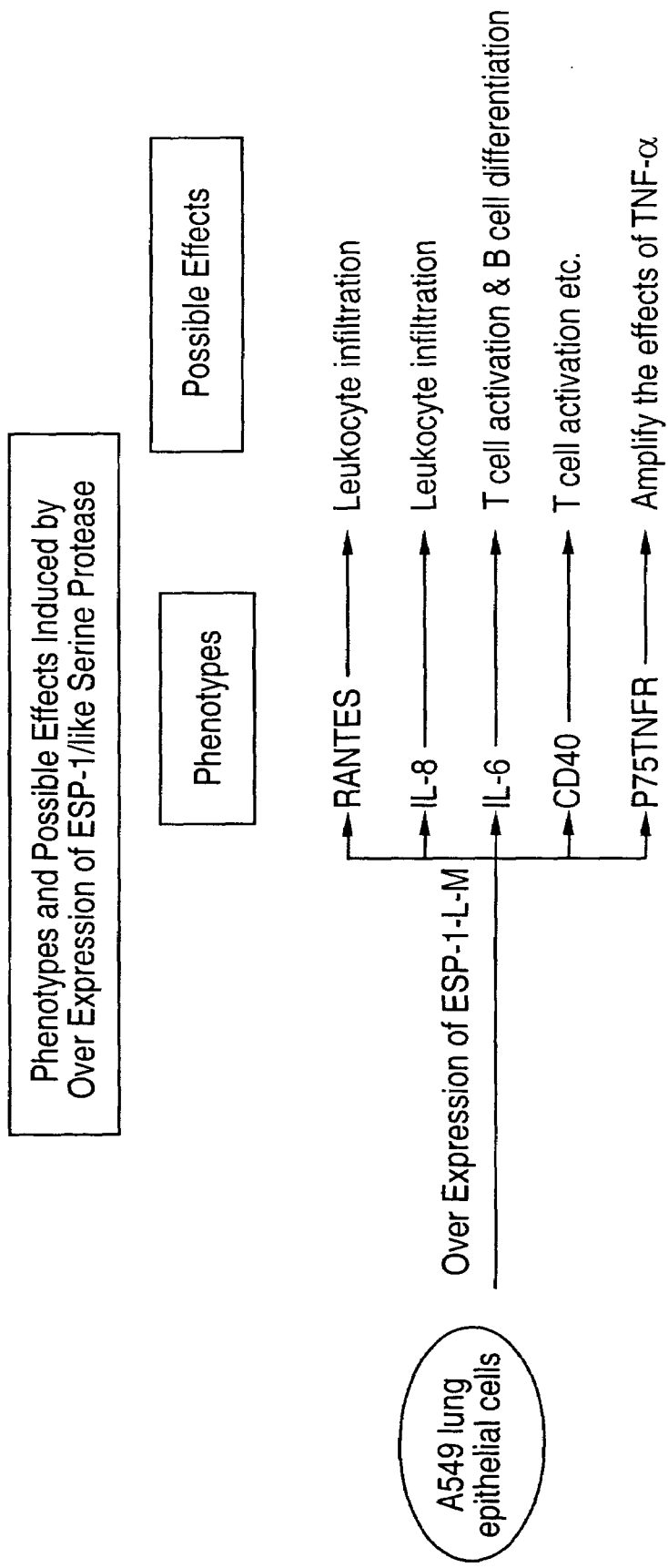
FIG. 20. Phenotypes and possible effects induced by over-expression of ESP-1-like enzyme.

Over expression of eosinophil serine protease 1-like enzyme induces phenotype changes of A549 lung epithelial cells. Since eosinophil serine protease 1-like enzyme is an inflammatory stimuli-inducible gene, to understand its biological function, eosinophil serine protease 1-like enzyme was expressed in A549 cells by transient transfection. Forty hours after transfection, total RNA was isolated. Over expression of eosinophil serine protease 1-like enzyme-induced phenotype was screened with a primer panel containing cytokines, chemokines, receptors, transcription factors, enzymes, et al. by LightCycler. FIG. 20 clearly demonstrated that the expression of eosinophil serine protease 1-like enzyme could induce the expression of chemokine RANTES, IL-8, cytokine IL-6, cell surface receptor CD40, and p75TNFR. The production of RANTES could also be confirmed at protein levels with ELISA. eosinophil serine protease 1-like enzyme-induced RANTES and IL-8 production suggested that eosinophil serine protease 1-like enzyme might contribute to leukocyte infiltration. Increased CD40 expression may contribute to T cell activation and p75 TNFR may amplify the effects of TNF-α.

Taken these data together, plausible models (FIG. 21) of eosinophil serine protease 1-like enzyme genes in asthma pathology would be:
1. Promote degradation of endothelium basal membrane and result in inflammation-induced endothelium leakage, plasma exudation, mucus production, tissue swelling, and infiltration of leukocytes.
2. Induce epithelium damage, shedding, and release of inflammation factors.
3. Facilitate the recruitment of eosinophils, monocytes, mature DC, activated T cells and B cells to the inflamed tissue
4. Regulation of cytokine and chemokine production
5. Regulation of receptor expression Activation of other protease or protease activated receptors and lead to induction of cellular signaling, airway remodeling, smooth muscle contraction and so on.

What is claimed is:

1. A polynucleotide encoding a protease comprising an amino acid sequence selected from the group consisting of
   (i) the amino acid sequence set forth in SEQ ID NO:2,
   (ii) the amino acid sequence set forth in SEQ ID NO:56,
   (iii) the amino acid sequence set forth in SEQ ID NO:58,
   (iv) an amino acid sequence that shares at least 98% amino acid sequence identity with the amino acid sequence set forth in SEQ ID NO:2, and
   (v) an amino acid sequence that shares at least 96% amino acid sequence identity with the amino acid sequence set forth in SEQ ID NO:56,
   wherein the encoded protease is capable of inducing the expression of one or more polypeptides selected from the group consisting of chemokines RANTES, IL-8, cytokine 1L-6, cell surface receptor CD40, and p75TNFR when the encoding polynucleotide is expressed in A549 lung epithelial cells.

2. The polynucleotide of claim 1 which comprises the nucleotide sequence shown in SEQ ID NO:1.

3. The polynucleotide of claim 1 which consists of the nucleotide sequence shown in SEQ ID NO:1.

4. An expression vector comprising the polynucleotide of claim 1.

5. The expression vector of claim 4 wherein the polynucleotide comprises the nucleotide sequence shown in SEQ ID NO:1.

6. The expression vector of claim 4 wherein the polynucleotide consists of the nucleotide sequence shown in SEQ ID NO:1.

7. A host cell comprising an expression vector which comprises the polynucleotide of claim 1.

8. The host cell of claim 7 wherein the polynucleotide comprises the nucleotide sequence shown in SEQ ID NO:1.

9. The host cell of claim 7 wherein the polynucleotide consists of the nucleotide sequence shown in SEQ ID NO:1.

10. An isolated polynucleotide encoding a protein that comprises an amino acid sequence selected from the group consisting of:
    (i) the amino acid sequence set forth in SEQ ID NO:2,
    (ii) the amino acid sequence set forth in SEQ ID NO:56, and
    (iii) the amino acid sequence set forth in SEQ ID NO:58.

11. An expression vector comprising the polynucleotide of claim 10.

12. A host cell comprising the expression vector of claim 11.

13. A method of producing a protease comprising an amino acid sequence selected from the group consisting of
    (i) the amino acid sequence set forth in SEQ ID NO:2,
    (ii) the amino acid sequence set forth in SEQ ID NO:56,
    (iii) the amino acid sequence set forth in SEQ ID NO:58,
    (iv) an amino acid sequence that shares at least 98% amino acid sequence identity with the amino acid sequence set forth in SEQ ID NO:2, and
    (v) an amino acid sequence that shares at least 96% amino acid sequence identity with the amino acid sequence set forth in SEQ ID NO:56,
    wherein the protease is capable of inducing the expression of one or more polypeptides selected from the group consisting of chemokines RANTES, IL-8, cytokine 1L-6, cell surface receptor CD40, and p75TNFR when the encoding polynucleotide is expressed in A549 lung epithelial cells, said method comprising the steps of:
    culturing a host cell comprising an expression vector of claim 4 that encodes the polypeptide under conditions whereby the polypeptide is expressed; and
    isolating the polypeptide.

14. The method of claim 13 wherein the expression vector comprises the nucleotide sequence shown in SEQ ID NO:1.

15. A method of detecting a coding sequence for a protease comprising an amino acid sequence selected from the group consisting of
    (i) the amino acid sequence set forth in SEQ ID NO:2,
    (ii) the amino acid sequence set forth in SEQ ID NO:56,
    (iii) the amino acid sequence set forth in SEQ ID NO:58,
    (iv) an amino acid sequence that shares at least 98% amino acid sequence identity with the amino acid sequence set forth in SEQ ID NO:2, and
    (v) an amino acid sequence that shares at least 96% amino acid sequence identity with the amino acid sequence set forth in SEQ ID NO:56,
    wherein the encoded protease is capable of inducing the expression of one or more polypeptides selected from the group consisting of chemokines RANTES, IL-8, cytokine 1L-6, cell surface receptor CD40, and p75TNFR when the encoding polynucleotide is expressed in A549 lung epithelial cells, said method comprising the steps of:
    hybridizing a polynucleotide comprising the complement of the nucleotide sequence set forth in SEQ ID NO:1 to nucleic acid material of a biological sample to form a hybridization complex under stringent conditions comprising wash conditions of 0.5×SSC, 0.1% SDS at 65° C.; and
    detecting the hybridization complex.

16. The method of claim 15 further comprising the step of amplifying the nucleic acid material before the step of hybridizing.

17. A kit for detecting a coding sequence for a protease comprising an amino acid sequence selected from the group consisting of
    (i) the amino acid sequence set forth in SEQ ID NO:2,
    (ii) the amino acid sequence set forth in SEQ ID NO:56,
    (iii) the amino acid set forth in SEQ ID NO:58,
    (iv) an amino acid sequence that shares at least 98% amino acid sequence identity with the amino acid sequence set forth in SEQ ID NO:2, and
    (v) an amino acid sequence that shares at least 96% amino acid sequence identity with the amino acid sequence set forth in SEQ ID NO:56,
    wherein the encoded protease is capable of inducing the expression of one or more polypeptides selected from the group consisting of chemokines RANTES, IL-8, cytokine 1L-6, cell surface receptor CD40, and p75TNFR when the encoding polynucleotide is expressed in A549 lung epithelial cells, said kit comprising:
    a polynucleotide comprising the complement of the nucleotide sequence set forth in SEQ ID NO:1; and
    instructions for the method of claim 15.

* * * * *